US008097733B2

(12) United States Patent
Alvira et al.

(10) Patent No.: US 8,097,733 B2
(45) Date of Patent: Jan. 17, 2012

(54) PYRAZOLE DERIVATIVES AS 5-LO-INHIBITORS

(75) Inventors: Edgardo Alvira, O'Fallon, MO (US); Matthew J. Graneto, Chesterfield, MO (US); Margaret Lanahan Grapperhaus, Troy, IL (US); Kaliappan Iyanar, Ballwin, MO (US); Todd Michael Maddux, Portage, MI (US); Matthew William Mahoney, St. Peters, MO (US); Mark Alan Massa, Chesterfield, MO (US); Kirby Ray Sample, St. Louis, MO (US); Michelle Ann Schmidt, Millstadt, IL (US); Ronald Edward Seidel, Creve Coeur, MO (US); Jon Gordon Selbo, Wentzville, MO (US); Michael Brent Tollefson, Dardenne Prairie, MO (US); Richard Alan Vonder Embse, St. Louis, MO (US); Grace Mary Wagner, Webster Groves, MO (US); Scott Santford Woodard, Manchester, MO (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/276,779

(22) Filed: Nov. 24, 2008

(65) Prior Publication Data

US 2009/0227634 A1 Sep. 10, 2009

Related U.S. Application Data

(60) Provisional application No. 61/004,261, filed on Nov. 26, 2007, provisional application No. 61/004,236, filed on Nov. 26, 2007, provisional application No. 61/055,497, filed on May 23, 2008.

(51) Int. Cl.
*C07D 231/10* (2006.01)
(52) U.S. Cl. .................................................. 548/377.1
(58) Field of Classification Search ................ 548/377.1
See application file for complete search history.

(56) References Cited

U.S. PATENT DOCUMENTS

| 5,225,438 | A | 7/1993 | Dowell et al. | 514/459 |
| 5,254,581 | A | 10/1993 | Bruneau et al. | 514/460 |
| 5,272,173 | A | 12/1993 | Dowell et al. | 514/459 |
| 5,276,037 | A | 1/1994 | Dowell et al. | 514/252.01 |
| 5,332,757 | A | 7/1994 | Bird et al. | 514/459 |
| 5,407,945 | A | 4/1995 | Bruneau et al. | 514/312 |
| 5,883,106 | A | 3/1999 | Stevens et al. | 514/277 |
| 6,063,928 | A | 5/2000 | Stevens et al. | 546/269.7 |
| 6,239,285 | B1 | 5/2001 | Norris et al. | 548/304.7 |
| 7,772,269 | B2 * | 8/2010 | Graneto et al. | 514/406 |
| 2007/0173508 | A1 | 7/2007 | Hutchinson et al. | 514/250 |
| 2008/0021080 | A1 | 1/2008 | Verma et al. | 514/384 |

FOREIGN PATENT DOCUMENTS

| WO | WO 9611911 | 4/1996 |
| WO | WO 2008 065493 | 6/2008 |

OTHER PUBLICATIONS

Tietz, NW, "Progress in the development of a recommended method for alkaline phosphatase activity measurements", Alkaline Phosphatase Study Group. Committee on Standards of the AACC, Subcommittee on Enzymes, Clinical Chemistry, vol. 26, No. 7, 1980, p. 1023.
Bowles, DK et al., "Hypercholesterolemia inhibits L-type calcium current in coronary macro-, not microcirculation", J Appl Physiol 96: 2240-2248, 2004.
Chai, S., et al. "Overexpression of hyaluronan in the tunica media promotes the development of atherosclerosis", Circ Res. 2005;96:583-591.
Cramer, CT, et al., "Effects of a novel dual lipid synthesis inhibitor and its potential utility in treating dyslipidemia and metabolic syndrome", J. Lipid Res. 2004. 45:1289-1301.
Dupont, NC, et al. "Validation and comparison of luminex multiplex cytokine analysis kits with ELISA: Determinations of a panel of nine cytokines in clinical sample culture supernatants", J. of Reporductive Immunology, 66(2005) 175-191.
Lutgens, E. et al. "Atherosclerosis in ApoE*3-Leiden transgenic mice: From proliferative to atheromatous stage" Circulation, 99(2), Jan. 19, 1999, 276-283.
Nishina, PM. et al. "Atherosclerosis and plasma and liver lipids in nine inbred strains of mice" Lipids, 28, 599-605 (1993).
Nachtigal et al. "The application of stereological methods for the quantitative analysis of the atherosclerotic lesions in rabbits", Image Anal Stereol 2002;21:165-174.
Rubio, CA, et al. "Quantitation of Fibrosis in Liver Biopsies", Anal Quant Cytol Histol 10(2):107-109, 1988.
Temel, et al. "Intestinal cholesterol absorption is substantially reduced in mice deficient in both ABCA1 and ACAT2", J. Llpd Res. 2005 46: 2423-2431.
Tietz, NW, Clinical Guide to Laboratory Tests, $3^{rd}$ Edition, WB Saunders Company, Philadelphia, PA pp. 20-21 1995.
Tietz, NW, Clinical Guide to Laboratory Tests, $3^{rd}$ Edition, WB Saunders Company, Philadelphia, PA pp. 30-33 1995.
Mano et al "5-lipoxygenase inhibitor: convenient synthesis of 4-[3-(4-heterocyclylphenylthio)phenyl]- 3,4,5,6-tetrahydro-2H-pyran-4-carboxamide analogues" Biorganic and Medicinal chemistry letters, Pergamon, Elsevier science, GB, vol. 15, No. 10 (2005) pp. 2611-2615.

* cited by examiner

*Primary Examiner* — Rebecca Anderson
*Assistant Examiner* — Samantha Shterengarts
(74) *Attorney, Agent, or Firm* — Robert T. Ronau; Gregg C. Benson

(57) ABSTRACT

The invention relates to compounds of formula (I)

(I)

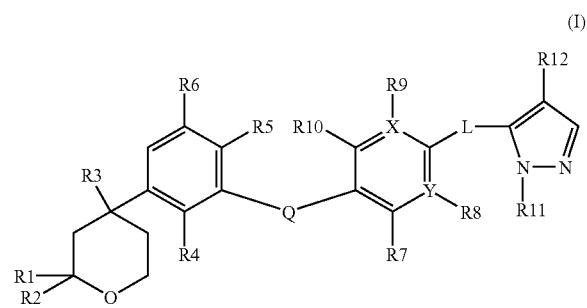

processes for their preparation, their use as 5-lipoxygenase inhibitors and pharmaceutical compositions containing the same.

5 Claims, 2 Drawing Sheets

PYRAZOLE DERIVATIVES AS 5-LO-INHIBITORS

FIELD OF THE INVENTION

This invention relates to compounds of general formula (I):

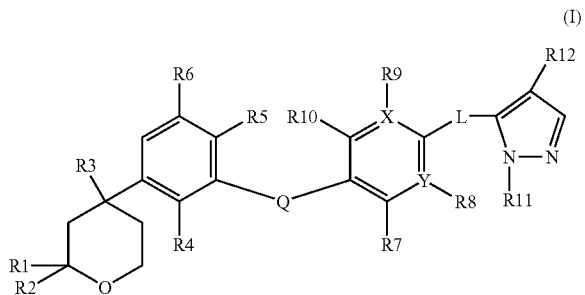

wherein Q, X, Y, L, $R^1$-$R^{12}$ have the meanings indicated below, provided that the compound is not (a) 4-(3-{[3-fluoro-4-(1-methyl-1H-pyrazol-5-yl)phenyl]thio}phenyl)tetrahydro-2H-pyran-4-carboxamide; or (b) 4-(3-{[4-(1-methyl-1H-pyrazol-5-yl)phenyl]thio}phenyl)tetrahydro-2H-pyran-4-carboxamide; as well as to processes and intermediates for the preparation of, compositions containing and the uses of such derivatives.

BACKGROUND OF THE INVENTION

The leukotrienes (LT) are a group of highly potent lipid mediators that play critical roles in numerous diseases, including inflammatory diseases and allergic disease states (Samuelsson, B., 1983, Leukotrienes: Science 220, 568-575). The enzyme 5-lipoxygenase (5-LO) converts arachidonic acid into the leukotriene A4 (LTA4) which may then be hydrolyzed into leukotriene B4 (LTB4) by the enzyme LTA4 hydrolase, or may react to form leukotriene C4 (LTC4) by a catalytic reaction mediated by LTC4 synthase.

Leukotrienes B4, C4, D4, and E4 have been shown experimentally to play a role in the inflammation involved in asthma. In addition, inhaled LTC4 and leukotriene D4 (LTD4) have been reported to be the most potent bronchoconstrictors yet studied in human subjects. LTC4 and LTD4 have also been reported to possibly cause migration of inflammatory cells into asthmatic airways (O'Byrne, Chest, Vol 111, (2):27).

Activation of the 5-lipoxygenase (5-LO) pathway leads to the biosynthesis of a number of proinflammatory leukotriene lipid mediators. The critical role of leukotrienes in allergic and respiratory diseases has been demonstrated using several animal models of LT deficiency, particularly 5-LO knock-out mice (Leuchron Contract No. QLG1-CT-2001-01521, Review, The Leukotrienes: Signaling Molecules in Chronic and Degenerative Diseases: Byrum, R. S., Goulet, J. L., Snouwaert, J. N., Griffiths, R. J. & Koller, B. H. (1999), J Immunol 163, 6810-6819. Bailie, M. B., Standiford, T. J., Laichalk, L. L., Coffey, M. J., Strieter, R. & Peters-olden, M. (1996), J. Immunol. 157, 5221-5224). In addition, drugs that interfere with the biosynthesis and action of LTs have been marketed as novel medications against asthma and allergic rhinitis (Drazen, J. F., Israel, E. & O'Byrne, P. (1999), N. Engl. J. Med. 340, 197-206). For a review article on lipoxygenase inhibitors, see H. Masamune and L. S. Melvin, Sr.: Annual Reports in Medicinal Chemistry, 1989, 24, pp 71-80 (Adademic).

In particular, 4-(3-(4-(2-methyl-1H-imidazol-1-yl)phenylthio)phenyl)-tetrahydro-2H-pyran-4-carboxamide was previously tested in human clinical trials (U.S. Pat. No. 5,883,106 and EP 0787127).

Accordingly, there is still a need for alternative and possibly improved 5-LO receptor antagonists, wherein improvement would desirably reside in better physicochemical properties in terms of e.g. solubility, and/or a better pharmacological profile in terms of e.g. in vivo activity, potency, side effects or pharmacokinetics. In this context, the present invention relates to novel 5-LO receptor antagonists.

SUMMARY OF THE INVENTION

In one aspect, the invention relates to a compound of formula (I)

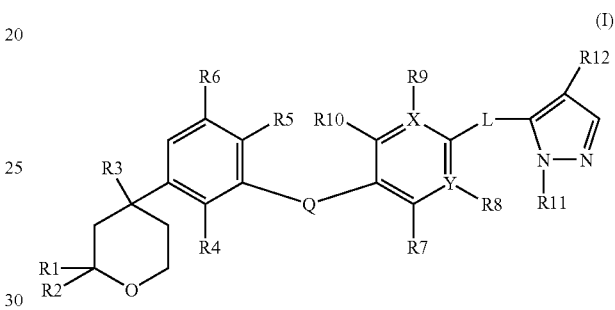

or a pharmaceutically acceptable salt or solvate thereof, wherein,

Q is —S— or —S(O)—;

X and Y are each independently selected from the group consisting of C and N;

L is selected from the group consisting of
(a) bond
(b) —(CH$_2$)—
(c) —O—
(d) —C(O)—

$R^1$ and $R^2$ are each independently selected from the group consisting of
(a) H
(b) methyl
(c) ethyl $R^3$ is selected from the group consisting of
(a) ←CN
(b) ←C(O)NH$_2$
(c) ←C(O)NH(CH$_3$)
(d) ←C(O)N(CH$_3$)$_2$ $R^4$ is H or halo $R^5$ is selected from the group consisting of
(a) H
(b) halo
(c) ←CN
(d) ←OCH$_3$ $R^5$ is selected from the group consisting of
(a) H
(b) halo
(c) ←CN $R^7$ is selected from the group consisting of
(a) H
(b) halo
(c) ←CN
(d) methyl
(e) ←OCH$_3$ R[8] is absent when Y is N, or R[8] is selected from the group consisting of
(a) H
(b) halo
(c) ←CN
(d) methyl
(e) ←OCH$_3$ R[9] is absent when X is N, or R[9] is selected from the group consisting of
(a) H
(b) halo
(c) ←CN
(d) methyl
(e) ←CF$_3$
(f) ←OCH$_3$ R[10] is selected from the group consisting of
(a) H
(b) halo
(c) ←CN R[11] is H or (C$_1$-C$_7$)alkyl, R[12] is H or halo provided that the compound of formula (I) is not:
(a) 4-(3-{[3-fluoro-4-(1-methyl-1H-pyrazol-5-yl)phenyl]thio}phenyl)tetrahydro-2H-pyran-4-carboxamide, or a pharmaceutically acceptable salt or solvate thereof, or
(b) 4-(3-{[4-(1-methyl-1H-pyrazol-5-yl)phenyl]thio}phenyl)tetrahydro-2H-pyran-4-carboxamide or a pharmaceutically acceptable salt or solvate thereof.

In another aspect, the present invention relates to a pharmaceutical composition comprising a compound of formula (I) as defined above, or a pharmaceutically acceptable salt or solvate thereof, and one or more pharmaceutically acceptable excipients.

In another aspect, the present invention relates to a combination particularly for treating a 5-LO-mediated disease, disorder or condition, said combination comprising a compound of formula (I) as defined above, or a pharmaceutically acceptable salt or solvate thereof, and one or more additional therapeutic agents.

In another aspect, the present invention relates to a compound of formula (I) as defined above, or a pharmaceutically acceptable salt or solvate thereof, as defined above, for use as a medicament.

In another aspect, the present invention is directed to a method of treating a 5-LO-mediated disease, disorder or condition in a subject in need of such treatment, by administering a therapeutically effective amount of a compound of formula (I) as defined above, or a pharmaceutically acceptable salt or solvate thereof to said subject.

In another aspect, the present invention is directed to a compound of formula (I) as defined above, or a pharmaceutically acceptable salt or solvate thereof, for use in treating a 5-LO mediated disease, disorder or condition.

In another aspect, the present invention is directed to the use of a compound of formula (I) as defined above, or a pharmaceutically acceptable salt or solvate thereof, for the manufacture of a medicament for treating a 5-LO mediated disease, disorder or condition.

In another aspect, the present invention is directed to a method for the manufacture of a compound of formula (I) said method comprising (i) contacting in a suitable solvent a compound of formula 1

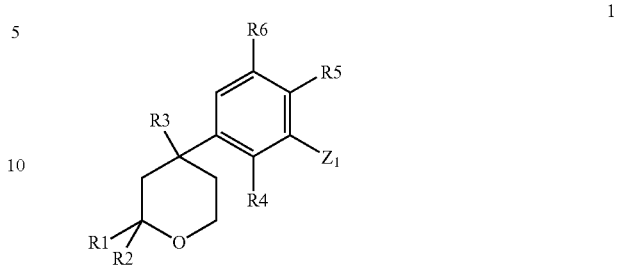

wherein R[1] to R[6] are as defined above and Z$_1$ is a leaving group or coupling partner, with a compound of formula 2

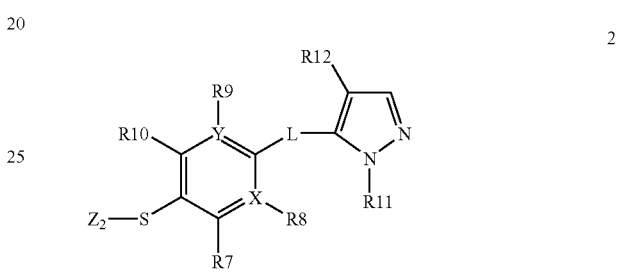

wherein X, Y, L and R[7] to R[12] are as defined above and Z$_2$ is hydrogen or a protecting group;

or, in alternative to (i)

(ii) contacting a compound of formula 4

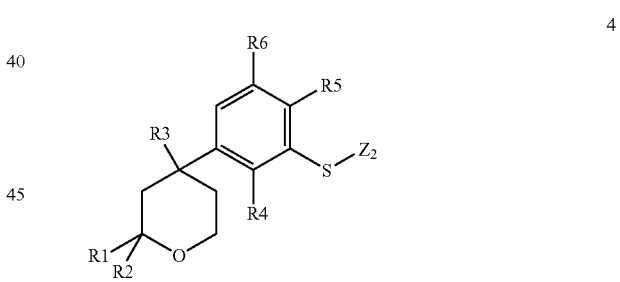

wherein R[1] to R[6] are as defined above and Z$_2$ is as defined in (i), with a compound of formula 6

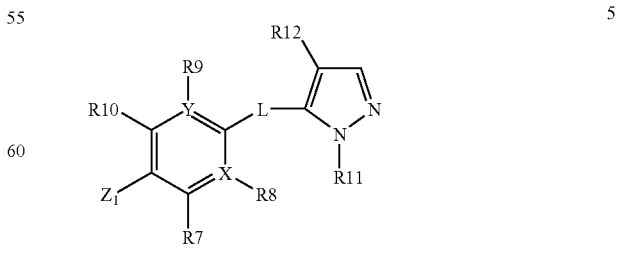

wherein X, Y, L and R[7] to R[12] are as defined above and Z$_1$ is as defined in (i) so as to obtain a compound of formula 3

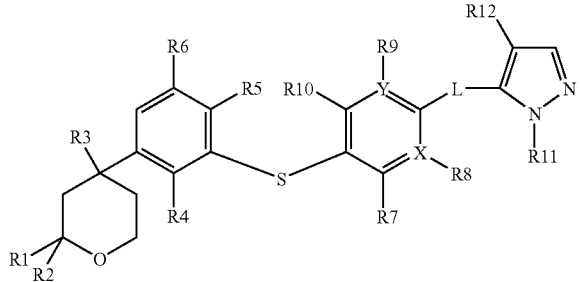

(iii) optionally, contacting said compound of formula 3 with an oxiding agent in a suitable solvent so as to obtain the corresponding sulfoxide of formula 18

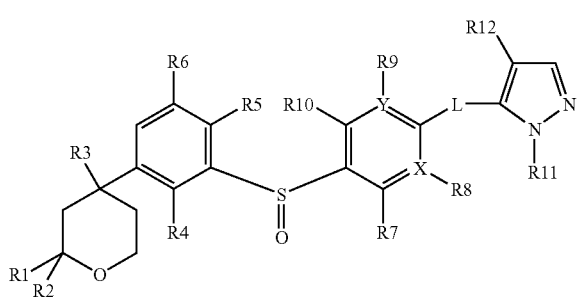

DETAILED DESCRIPTION OF THE INVENTION

Figure 1:
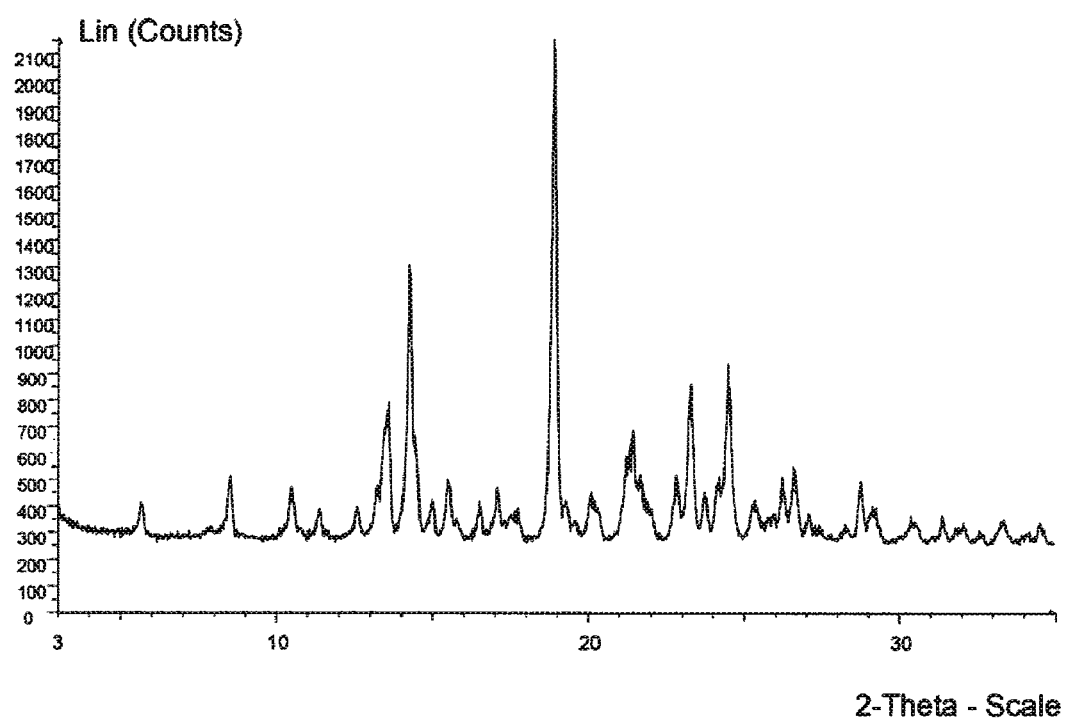
FIG. 1: measured PXRD pattern of a crystalline 1:1 molar ratio salt of (2S,4R)-4-(2-fluoro-3-{[4-(1-methyl-1H-pyrazol-5-yl)phenyl]thio}phenyl)-2-methyltetrahydro-2H-pyran-4-carbonitrile and para-toluenesulfonic acid (2 theta angles±0.1 degrees)

Even if not explicitly indicated, it must be understood that none of the aspects of the present invention encompasses the following compounds:

(a) 4-(3-{[3-fluoro-4-(1-methyl-1H-pyrazol-5-yl)phenyl]thio}phenyl)tetrahydro-2H-pyran-4-carboxamide, or a pharmaceutically acceptable salt or solvate thereof, and (b) 4-(3-{[4-(1-methyl-1H-pyrazol-5-yl)phenyl]thio}phenyl)tetrahydro-2H-pyran-4-carboxamide or a pharmaceutically acceptable salt or solvate thereof.

Unless otherwise indicated, in the present invention the language "a compound of formula (I)" means compounds of formula (I) or formula (Ia) or formula (Ib) or formula (Ic), wherein formulas (Ia), (Ib) and (Ic) are as defined below.

Unless otherwise indicated, in the present invention the language "a compound of formula (I) or a pharmaceutically acceptable salt or solvate thereof" is intended to identify a compound of formula (I), a pharmaceutically acceptable salt of a compound of formula (I), a pharmaceutically acceptable solvate of a compound of formula (I), a pharmaceutically acceptable solvate of a pharmaceutically acceptable salt of a compound of formula (I). It is also understood that the language "a compound of formula (I)" includes the compounds of formula (I) as hereinbefore defined, all polymorphs and crystal habits thereof, prodrugs and isomers thereof (including optical, geometric and tautomeric isomers), as well as isotopically-labeled compounds of formula (I).

In the above general formula (I):
alkyl means a cyclic, straight-chained or branched fully saturated hydrocarbon group or a combination of cyclic, straight-chained or branched fully saturated hydrocarbon groups. The language ($C_1$-$C_7$)alkyl means an alkyl group as defined above containing 1, 2, 3, 4, 5, 6 or 7 carbon atoms. The language ($C_1$-$C_6$)alkyl means an alkyl as defined above, containing 1, 2, 3, 4, 5, or 6 carbon atoms Examples of suitable ($C_1$-$C_7$)alkyl or ($C_1$-$C_6$)alkyl radicals include methyl, ethyl, n-propyl, iso-propyl, n-butyl, iso-butyl, sec-butyl, tert-butyl, n-pentyl, iso-pentyl, n-hexyl, iso-hexyl, cyclopropyl, cyclobutyl, cyclopentyl, cyclohexyl, cycloheptyl, ←-($CH_2$)-cyclopropyl, ←-($CH_2$)-cyclopentyl;

halo means a halogen atom selected from the group consisting of fluoro, chloro, bromo and iodo. Unless otherwise indicated, halo is preferably chloro or fluoro;

the arrows clarify the side of the radicals that are linked to the chemical core of formula (I).

In the present invention, the phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition. Non-limiting examples include reduction in pain, discomfort, swelling or fever.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Non-limiting examples include administration of the compound or combination to a subject simultaneously with, prior to, or subsequent to surgery; and administration of the compound or combination with a further combination of drugs or agents. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, inhibition of progressive nerve destruction, reduction of biomarkers associated and correlated with diseases or disorders, and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

As used herein, the term "5-LO mediated disease", or "5-LO-mediated disorder" or "5-LO-mediated condition" refers to any disease, disorder, or condition (particularly any pathological conditions), respectively, in which 5-LO plays a role, either by control of 5-LO itself, or by 5-LO causing leukotrienes to be released, or other like compounds whose production or action is exacerbated or secreted in response to 5-LO.

In one embodiment, the compound of formula (I) has formula (Ia):

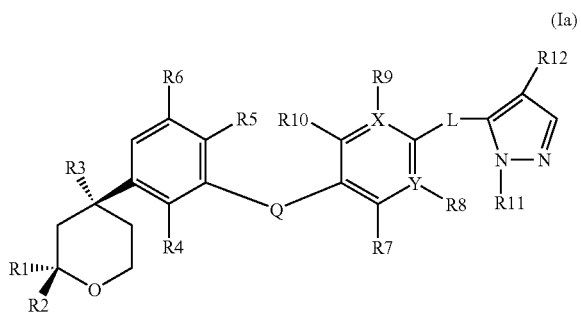

(Ia)

or a pharmaceutically acceptable salt or solvate thereof, wherein Q, X, Y, L and $R^1$-$R^{12}$ are as defined above In one embodiment, the compound of formula (I) has formula (Ib)

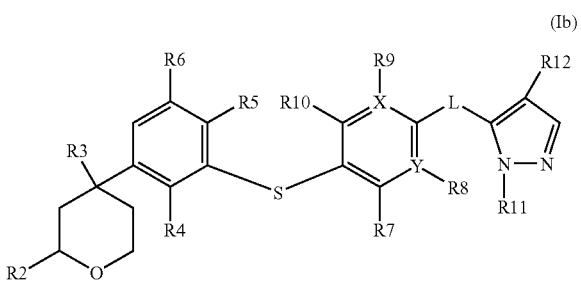

(Ib)

or a pharmaceutically acceptable salt or solvate thereof, wherein

L is selected from the group consisting of
(a) bond
(b) —($CH_2$)—
(c) —O—
(d) —C(O)—

X and Y are each independently selected from the group consisting of C and N $R^2$ is selected from the group consisting of
(a) H
(b) methyl
(c) ethyl $R^3$ is selected from the group consisting of
(a) ←CN
(b) ←C(O)$NH_2$
(c) ←C(O)NH($CH_3$)

$R^4$ is H or halo $R^5$ is selected from the group consisting of
(a) H
(b) halo
(c) ←$OCH_3$ $R^6$ is H or halo $R^7$ is selected from the group consisting of
(a) H
(b) halo
(c) ←CN
(d) methyl
(e) ←$OCH_3$ $R^8$ is absent when Y is N, or $R^8$ is selected from the group consisting of
(a) H
(b) halo
(c) ←CN $R^9$ is absent when X is N, or $R^9$ is selected from the group consisting of
(a) H
(b) halo
(c) ←CN
(d) methyl
(e) $CF_3$ $R^{10}$ is selected from the group consisting of
(a) H
(b) halo
(c) ←CN $R^{11}$ is H or ($C_1$-$C_7$)alkyl $R^{12}$ is H or halo.

In one embodiment, the compound of formula (I) has formula (Ic)

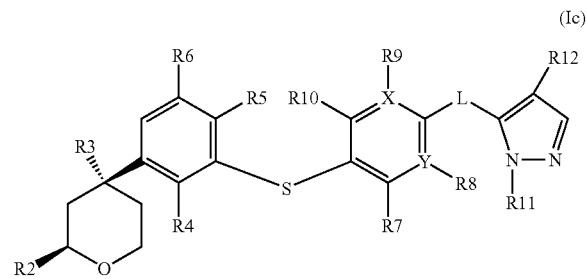

(Ic)

or a pharmaceutically acceptable salt or solvate thereof, wherein X, Y and $R^2$-$R^{12}$ are as defined for formula (Ib).

In one embodiment, the compounds of the invention have formula (I) or (Ia), wherein Q is S.

In one embodiment, the compounds of the invention have formula (I), (Ia), (Ib) or (Ic), wherein L is selected from the group consisting of a bond, —O— and —C(O)—, preferably L is a bond or —O—, more preferably L is a bond.

In one embodiment, the compounds of the invention have formula (I), (Ia), (Ib) or (Ic), wherein X and Y are either both C or one is C and the other one is N. Preferably both X and Y are C.

In one embodiment, the compounds of the invention have formula (I) or (Ia), wherein $R^1$ is selected from the group consisting of H and methyl, preferably $R^1$ is H.

In one embodiment, the compounds of the invention have formula (I), (Ia), (Ib) or (Ic), preferably formula (Ic), wherein $R^2$ is H or methyl, preferably $R^2$ is methyl.

In one embodiment, the compounds of the invention have formula (I), (Ia), (Ib) or (Ic), preferably formula (Ic), wherein $R^3$ is selected from the group consisting of ←CN, ←C(O)$NH_2$ and ←C(O)NH$CH_3$, preferably $R^3$ is ←CN, or ←C(O)$NH_2$.

In one embodiment, the compounds of the invention have formula (I), (Ia), (Ib) or (Ic), preferably formula (Ic), wherein $R^4$ is selected from the group consisting of H, Cl and F, preferably $R^4$ is F.

In one embodiment, the compounds of the invention have formula (I), (Ia), (Ib) or (Ic), preferably formula (Ic), wherein $R^5$ is selected from the group consisting of H, ←OCH$_3$, Cl and F. More preferably, $R^5$ is H or F, even more preferably $R^5$ is H.

In one embodiment, the compounds of the invention have formula (I), (Ia), (Ib) or (Ic), preferably formula (Ic), wherein $R^6$ is H or F, preferably $R^6$ is H.

In one embodiment, the compounds of the invention have formula (I), (Ia), (Ib) or (Ic), preferably formula (Ic), wherein $R^7$ is selected from the group consisting of H, Cl and F. Preferably $R^7$ is H.

In one embodiment, the compounds of the invention have formula (I), (Ia), (Ib) or (Ic), preferably formula (Ic), wherein $R^8$, if present, is selected from the group consisting of H, ←CN, F and Cl. Preferably $R^8$, if present, is H.

In one embodiment, the compounds of the invention have formula (I), (Ia), (Ib) or (Ic), preferably formula (Ic), wherein $R^9$, if present, is selected from the group consisting of H, ←CN, methyl, CF$_3$, F and Cl. Preferably $R^9$, if present, is selected from the group consisting of H, F and Cl. More preferably $R^9$, if present, is H.

In one embodiment, the compounds of the invention have formula (I), (Ia), (Ib) or (Ic), preferably formula (Ic), wherein $R^{10}$ is H or F, preferably $R^{10}$ is H.

In one embodiment, the compounds of the invention have formula (I), (Ia), (Ib) or (Ic), preferably formula (Ic), wherein $R^{11}$ is H or (C$_1$-C$_6$)alkyl. Preferably $R^{11}$ is selected from the group consisting of H, methyl, ethyl, iso-propyl, cyclopentyl, cyclohexyl, cycloheptyl, ←methyleneyclopropyl and ←methyleneyclopentyl. More preferably, $R^{11}$ is methyl.

In one embodiment, the compounds of the invention have formula (I), (Ia), (Ib) or (Ic), preferably formula (Ic), wherein $R^{12}$ is H.

In one embodiment, the compounds of the invention have formula (I), (Ia), (Ib) or (Ic), preferably formula (Ic), wherein at least one among $R^4$, $R^5$, $R^6$ and $R^9$, preferably at least one among $R^4$, $R^6$ and $R^9$, more preferably at least $R^4$, is halo, preferably F.

In one embodiment, the compounds of the invention have formula (I), (Ia), (Ib) or (Ic), preferably formula (Ic), wherein L is selected from the group consisting of a bond, —O— and —C(O)—, preferably L is —O—; and one of X and Y is C and the other is N, preferably X is C and Y is N.

In one embodiment, the compounds of the invention have formula (I), (Ia), (Ib) or (Ic), preferably formula (Ic), wherein L is selected from the group consisting of a bond, —O— and —C(O)—, preferably L is —O—; one of X and Y is C and the other is N, preferably X is C and Y is N; $R^8$ is absent if Y is N, or $R^8$ is Cl, and $R^9$ is absent if X is N, or $R^9$ is Cl.

In one embodiment, the compounds of the invention have formula (I), (Ia), (Ib) or (Ic), preferably formula (Ic), wherein L is selected from the group consisting of a bond, —O— and —C(O)—, preferably L is —O—; one of X and Y is C and the other is N, preferably X is C and Y is N; $R^1$, $R^7$, $R^{10}$ and $R^{12}$ are each H; $R^2$ is methyl; $R^3$ is ←CN or ←C(O)NH$_2$; $R^4$ is H or F, preferably $R^4$ is F; $R^5$, $R^6$ are each independently H or F, preferably $R^5$ and $R^6$ are both H; $R^8$ is absent if Y is N, or $R^8$ is Cl; $R^9$ is absent if X is N, or $R^9$ is Cl; and $R^{11}$ is methyl.

In one embodiment, the compounds of the invention have formula (I), (Ia), (Ib) or (Ic), preferably formula (Ic), wherein L is selected from the group consisting of a bond, —O— and —C(O)—, preferably L is a bond; and X and Y are each C.

In one embodiment, the compounds of the invention have formula (I), (Ia), (Ib) or (Ic), preferably formula (Ic), wherein L is selected from the group consisting of a bond, —O— and —C(O)—, preferably L is a bond; X and Y are each C; $R^8$ is selected from the group consisting of H, F and ←CN, preferably $R^8$ is H or F, more preferably $R^8$ is H; and $R^9$ is selected from the group consisting of H, F, Cl, ←CN, preferably $R^9$ is selected form the group consisting of H, Cl and F, more preferably $R^9$ is H.

In one embodiment, the compounds of the invention have formula (I), (Ia), (Ib) or (Ic), preferably formula (Ic), wherein L is a bond; X and Y are each C; $R^1$ is H; $R^2$ is H or methyl, preferably $R^2$ is methyl; $R^3$ is selected from the group consisting of ←CN, ←C(O)NH$_2$ and ←C(O)NHCH$_3$, preferably $R^3$ is selected from the group consisting of ←CN and ←C(O)NH$_2$; $R^4$ is H or F, preferably $R^4$ is F; $R^5$ and $R^6$ are each independently H or F, preferably $R^5$ and $R^6$ are both H; $R^{10}$ is H or F, preferably $R^{10}$ is H; $R^7$ is selected from the group consisting of H, F and Cl, preferably $R^7$ is H; $R^8$ is selected from the group consisting of H, F and ←CN, preferably $R^8$ is H or F, more preferably $R^8$ is H; $R^9$ is selected from the group consisting of H, F, Cl and ←CN, preferably $R^9$ is H, Cl or F, more preferably $R^9$ is H; $R^{11}$ is methyl; and $R^{12}$ is H.

Preferred compounds of the invention are:

4-(3-{[3-fluoro-4-(1-methyl-1H-pyrazol-5-yl)phenyl]thio}phenyl)tetrahydro-2H-pyran-4-carboxamide 4-(2-fluoro-3-{[4-(1-methyl-1H-pyrazol-5-yl)phenyl]thio}phenyl)-N-methyltetrahydro-2H-pyran-4-carboxamide 4-(2,5-difluoro-3-{[4-(1-methyl-1H-pyrazol-5-yl)phenyl]thio}phenyl)-N-methyltetrahydro-2H-pyran-4-carboxamide 4-(2,4-difluoro-3-{[4-(1-methyl-1H-pyrazol-5-yl)phenyl]thio}phenyl)tetrahydro-2H-pyran-4-carboxamide 4-(4-fluoro-3-{[4-(1-methyl-1H-pyrazol-5-yl)phenyl]thio}phenyl)tetrahydro-2H-pyran-4-carboxamide (2S,4R)-2-methyl-4-(3-{[4-(1-methyl-1H-pyrazol-5-yl)phenyl]thio}phenyl)tetrahydro-2H-pyran-4-carboxamide (2S,4R)-4-(2-fluoro-3-{[4-(1-methyl-1H-pyrazol-5-yl)phenyl]thio}phenyl)-2-methyltetrahydro-2H-pyran-4-carboxamide (2S,4R)-4-(4-fluoro-3-{[4-(1-methyl-1H-pyrazol-5-yl)phenyl]thio}phenyl)-2-methyltetrahydro-2H-pyran-4-carboxamide (2S,4R)-4-(3-fluoro-5-{[4-(1-methyl-1H-pyrazol-5-yl)phenyl]thio}phenyl)-2-methyltetrahydro-2H-pyran-4-carboxamide (2S,4R)-4-(2,4-difluoro-3-{[4-(1-methyl-1H-pyrazol-5-yl)phenyl]thio}phenyl)-2-methyltetrahydro-2H-pyran-4-carboxamide (2S,4R)-4-(3-fluoro-5-{[4-(1-methyl-1H-pyrazol-5-yl)phenyl]thio}phenyl)-2-methyltetrahydro-2H-pyran-4-carbonitrile (2S,4R)-4-(2-fluoro-3-{[4-(1-methyl-1H-pyrazol-5-yl)phenyl]thio}phenyl)-2-methyltetrahydro-2H-pyran-4-carbonitrile (2S,4R)-4-(3-{[3-fluoro-4-(1-methyl-1H-pyrazol-5-yl)phenyl]thio}phenyl)-2-methyltetrahydro-2H-pyran-4-carbonitrile (2S,4R)-4-(2-fluoro-3-{[3-fluoro-4-(1-methyl-1H-pyrazol-5-yl)phenyl]thio}phenyl)-2-methyltetrahydro-2H-pyran-4-carbonitrile (2S,4R)-4-(3-fluoro-5-{[3-fluoro-4-(1-methyl-1H-pyrazol-5-yl)phenyl]thio}phenyl)-2-methyltetrahydro-2H-pyran-4-carbonitrile 4-[3-({3-fluoro-4-[(1-methyl-1H-pyrazol-5-yl)methyl]phenyl}thio)phenyl]tetrahydro-2H-pyran-4-carboxamide 4-[3-({(4-[(1-methyl-1H-pyrazol-5-yl)carbonyl]phenyl}thio)phenyl]tetrahydro-2H-pyran-4-carboxamide 4-[3-({3-cyano-4-[(1-methyl-1H-pyrazol-5-yl)oxy]phenyl}thio)phenyl]tetrahydro-2H-pyran-4-carboxamide (2S,4R)-4-[2-fluoro-3-({4-[(1-methyl-1H-pyrazol-5-yl)carbonyl]phenyl}thio)phenyl]-2-methyltetrahydro-2H-pyran-4-carboxamide
(2S,4R)-4-[2-fluoro-3-({4-[(1-methyl-1H-pyrazol-5-yl)carbonyl]phenyl}thio)phenyl]-2-methyltetrahydro-2H-pyran-4-carbonitrile
4-[3-({5-chloro-6-[(1-methyl-1H-pyrazol-5-yl)oxy]pyridin-3-yl}thio)phenyl]tetrahydro-2H-pyran-4-carboxamide
(2S,4R)-4-[3-({5-chloro-6-[(1-methyl-1H-pyrazol-5-yl)oxy]pyridin-3-yl}thio)-2-fluorophenyl]-2-methyltetrahydro-2H-pyran-4-carbonitrile
(2S,4R)-4-[3-({5-chloro-6-[(1-methyl-1H-pyrazol-5-yl)oxy]pyridin-3-yl}thio)-2-fluorophenyl]-2-methyltetrahydro-2H-pyran-4-carboxamide or a pharmaceutically acceptable salt or solvate thereof.

In one embodiment, the compound (2S,4R)-4-(2-fluoro-3-{[4-(1-methyl-1H-pyrazol-5-yl)phenyl]thio}phenyl)-2-methyltetrahydro-2H-pyran-4-carboxamide or a pharmaceutically acceptable salt or solvate thereof, is preferred.

In one embodiment, the compound (2S,4R)-4-(2-fluoro-3-{[4-(1-methyl-1H-pyrazol-5-yl)phenyl]thio}phenyl)-2-methyltetrahydro-2H-pyran-4-carbonitrile, or a pharmaceutically acceptable salt or solvate thereof, is preferred. This compound has the following formula:

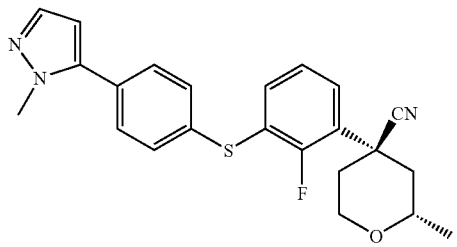

In one embodiment, the compound (2S,4R)-4-(2-fluoro-3-{[4-(1-methyl-1H-pyrazol-5-yl)phenyl]thio}phenyl)-2-methyltetrahydro-2H-pyran-4-carbonitrile tosylate salt, or a pharmaceutically acceptable solvate thereof, is preferred.

More preferably, the compound of the invention is a 1:1 molar ratio salt of (2S,4R)-4-(2-fluoro-3-{[4-(1-methyl-1H-pyrazol-5-yl)phenyl]thio}phenyl)-2-methyltetrahydro-2H-pyran-4-carbonitrile and para-toluenesulfonic acid. Said compound has the following formula:

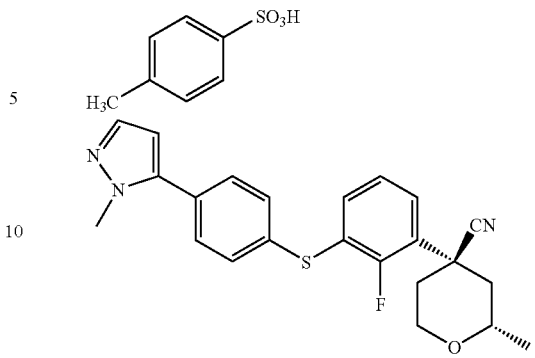

The compounds of formula (I) may be prepared by employing reactions as shown in the schemes below, in addition to other standard manipulations as are known in the literature, exemplified in the experimental procedures, or using methods known in the art in combination with methods described herein. These schemes, therefore, are not limited by the compounds listed nor by any particular substituents employed for illustrative purposes. In addition, solvents, temperatures, and other reaction conditions presented herein may vary according to those of skill in the art. In addition to methods used to make final targets, the starting materials used herein are commercially available or were prepared by methods known to those of ordinary skill in the art and can be found in standard reference books such as the Compendium of Organic Synthetic Methods, Vol. I-VI (Wiley); March, Advanced Organic Chemistry 5th Ed. (Wiley 2001); Carey and Sundberg, Advanced Organic Chemistry 4th Ed Vols. A and B (2000, 2001); Green and Wuts, Protective Groups in Organic Synthesis 3rd Ed. (Wiley 1999); Metal-Catalyzed Cross-Coupling Reactions, Wiley, 2nd Ed., 2004; Handbook of Heterocyclic Chemistry by A. R. Katritzky and A. F. Pozharskii, 2nd edition, (Pergamon, 2000) and references cited therein.

Unless otherwise indicated, all the schemes below disclose the preparation of compounds of formula (I) wherein Q is —S—. To obtain the corresponding compounds wherein Q is —S(O)— (see also compound 18, above) an oxidation step can be carried out for example by contacting the thio derivatives 3 with a conventional oxidizing agent (e.g. hydrogen peroxide) in a suitable solvent.

Scheme 1.0

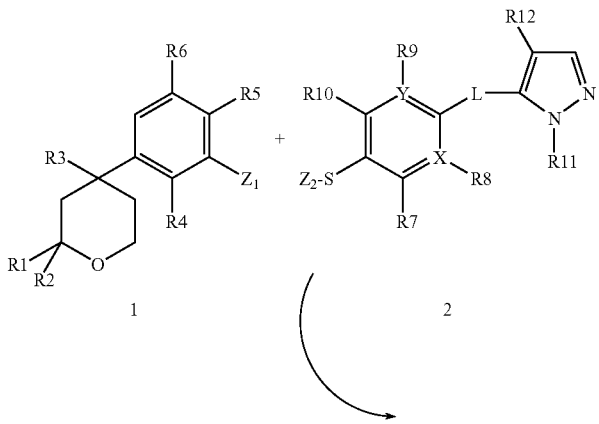

-continued

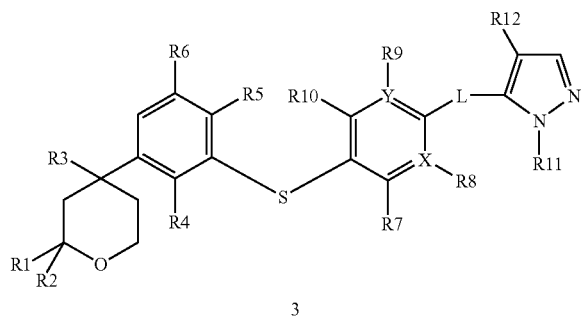

3

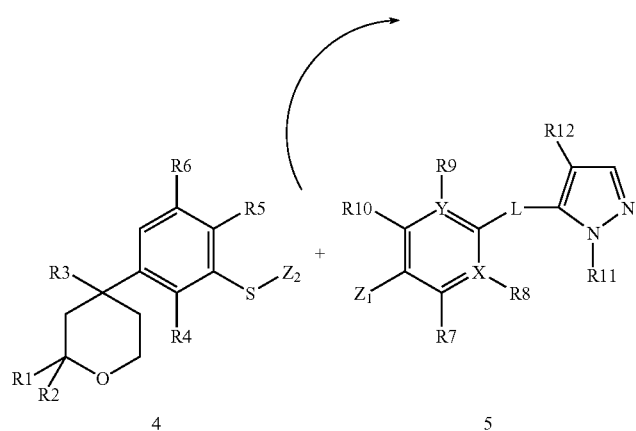

In scheme 1.0 an appropriately substituted compound 1 or 5 wherein $Z_1$ is a leaving group or coupling partner such as halo or triflate is reacted with a compound 2 or 4 wherein $Z_2$ is hydrogen or a protecting group such as acetyl or triisopropylsilyl as described in the literature and examples enclosed in the instant application. Reaction conditions typically employ a base such as sodium tert-butoxide, sodium bis(trimethylsilyl)amide, cesium carbonate, or potassium carbonate in a solvent such as dioxane, tetrahydrofuran, or N,N'-dimethylformamide. A palladium, copper, or other metal catalyst and additional reagents and optional excipients may be added such as palladium acetate, 1,1-bis(diisopropylphosphino)ferrocene, 1,1'-bis(diphenylphosphino)ferrocene palladium dichloride dichloromethane adduct, tetrakis(triphenylphosphine)palladium, bis[(2-diphenylphosphino)]phenyl ether, tetraethylammonium chloride monohydrate, cesium fluoride, tetrabutylammonium fluoride. Elevated temperatures in the range of 25-120° C. may be required. Additional conditions and reagents are described in Metal-Catalyzed Cross-Coupling Reactions, Wiley, 2nd Ed., 2004; Chemistry—A European Journal, 12(30), 7782-7796, 2006; Chem. Pharm. Bull., 2005, 53, p 965-973; Bioorg. Med. Chem. Lett., 2005, 15, p 2611-2615 and references cited therein.

Scheme 1.1

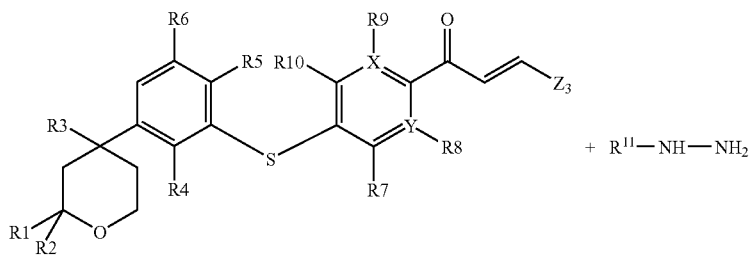

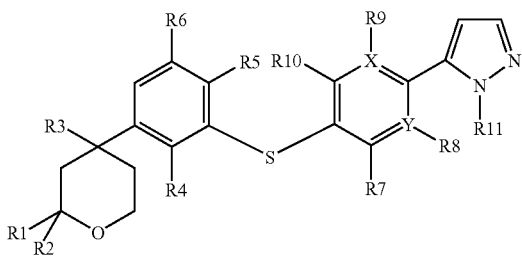

Scheme 1.1 is suitable to manufacture compounds of formula (I) wherein $R^{12}$ is H. In scheme 1.1, compounds of the invention are produced from intermediates such as 6 and 7 wherein $Z_3$ is dimethylamino or alkoxy. Reaction conditions may employ a solvent such as DMF or THF and elevated temperatures may be required. Other pyrazole forming conditions known in the literature such as those in 'Handbook of Heterocyclic Chemistry' by A. R. Katritzky and A. F. Pozharskii, 2nd edition, (Pergamon, 2000) may be used starting from the appropriate starting materials in addition to those shown in 6 and 7 and the enclosed examples. Intermediates such as 7 are commercially available or may be prepared according to methods known in the literature.

typically employ a solvent such as N-methylpyrollidine or DMF with the addition of a base such as Potassium t-butoxide, sodium hydride, or cesium carbonate. Elevated temperatures may be required. Further examples of nucleophyllic displacement conditions are known in the literature.

Intermediates such as 1 wherein $R^3$ is CN may be produced by the following procedures.

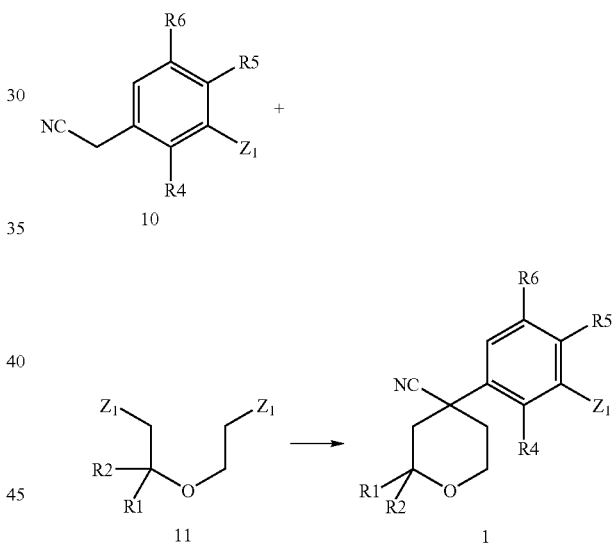

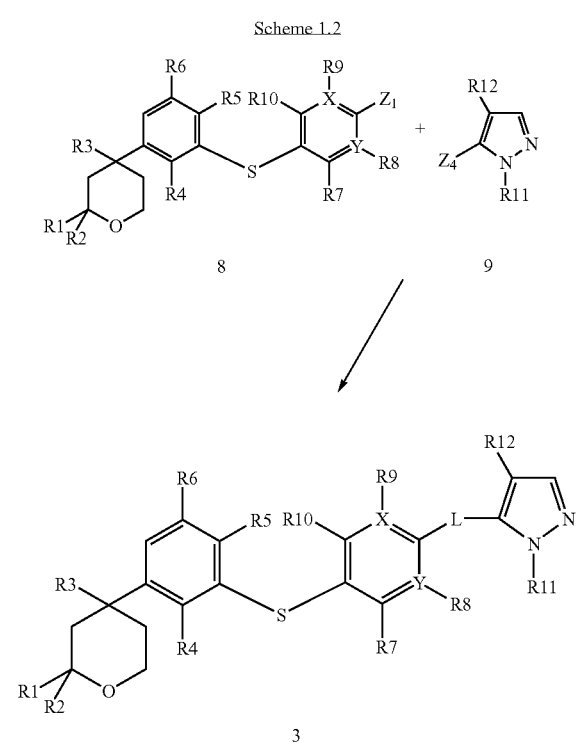

In scheme 1.2, compounds of the invention are produced from intermediates such as 8 and 9 wherein $Z_1$ is a leaving group suitable for a nucleophyllic displacement reaction as defined above. Examples of $Z_1$ are a halogen, mesylate, or triflate. $Z_4$ is a nucleophyllic group. An example of $Z_4$ is hydroxyl in which case L will be —O—. Reaction conditions Hydrolysis of CN radical to obtain the corresponding amides is well within the normal knowledge of a skilled person. In scheme 1.3 compounds such as 10 wherein $Z_1$ is a leaving group suitable for nucleophyllic displacement as defined above (e.g. a halogen, tosylate, mesylate, or triflate) are reacted with compounds such as 11 using a solvent such as DMSO, DMF, or THF and a base such as sodium hydride, potassium carbonate, or cesium carbonate. Reactions may be carried out at a range of temperatures from 0-110° C. Additional procedures and conditions may be found in Chemical & Pharmaceutical Bulletin, 53(8), 965-973, 2005; Jpn. Kokai Tokkyo Koho, 2000191654, 11 Jul. 2000; Bioorganic & Medicinal Chemistry Letters, 15(10), 2611-2615, 2005; 1977 Journal of Organic Chemistry, 60(13), 4264-7, 1995 Journal of Medicinal Chemistry, 36(2), 295-6, 1993 and references cited therein.

Intermediates such as 2 may be produced by the following procedures.

Scheme 1.4

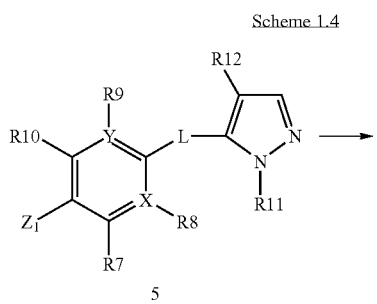

5

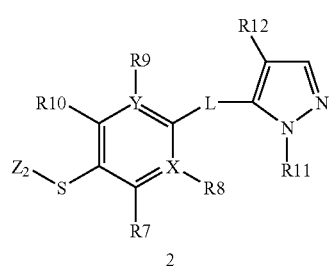

2

In Scheme 1.4 compounds such as 5 wherein $Z_1$ is a coupling partner as defined above, such as a halogen or triflate, is reacted with a thiol source such as triisopropylsilane thiol in a solvent such as dioxane, THF, toluene, or ether. A base, catalyst or other excipient may be added. Examples include 1,1-bis(diisopropylphosphino)ferrocene, 1,1'-bis(diphenylphosphino)ferrocene palladium dichloride dichloromethane adduct, tetrakis(triphenylphosphine) palladium, PdCl2(diphenyl-phosphino ferrocene), sodium t-butoxide or sodium hydride. Anhydrous conditions and elevated temperatures may also be employed in the reaction. Additional examples may be found in Organic Letters, 9(20), 4081-4083, 2007; Journal of Medicinal Chemistry, 50 (16) 3954-3963, 2007; Advanced Synthesis & Catalysis, 347 (2+3), 313-319, 2005; Tetrahedron Letters, 47(16), 2675-2678, 2006; Journal of the American Chemical Society, 128(7), 2180-2181, 2006; European Journal of Organic Chemistry, (16), 2630-2642, 2007; Tetrahedron Letters, 48(17), 3033-3037, 2007; Tetrahedron Letters, 44(35), 6699-6702, 2003 and references cited therein.

Intermediates such as 5 wherein L is —C(O)— may be produced by the following procedures.

Scheme 1.5

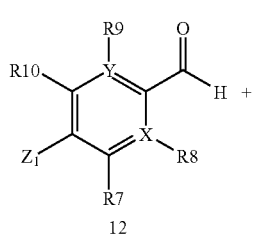

In scheme 1.5 compounds such as 5 wherein $Z_1$ is a leaving group as defined above such as a halogen may be prepared by reacting an appropriately compound such as 12 with an appropriately substituted compound such as 9 in a suitable solvent for organolithium chemistry such as THF or ether. In particular, an organolithium base such as butyl lithium is added to the pyrazole at reduced temperature in an inert atmosphere at reduced temperature followed by addition of an aldehyde such as 12. The resulting product is further oxidized to the ketone by oxidation conditions known in the literature such as pyridine chlorochromate in acetonitrile. Other conditions to effect this transformation are known in the literature such as Synlett, (6), 765-767, 1999; Journal of Organic Chemistry, 49(24), 4687-95, 1984; Journal of Heterocyclic Chemistry, 12(1), 49-57, 1975 and references cited therein.

Intermediates such as 5 wherein L is —(CH$_2$)— may be produced by the following procedures Scheme 1.6

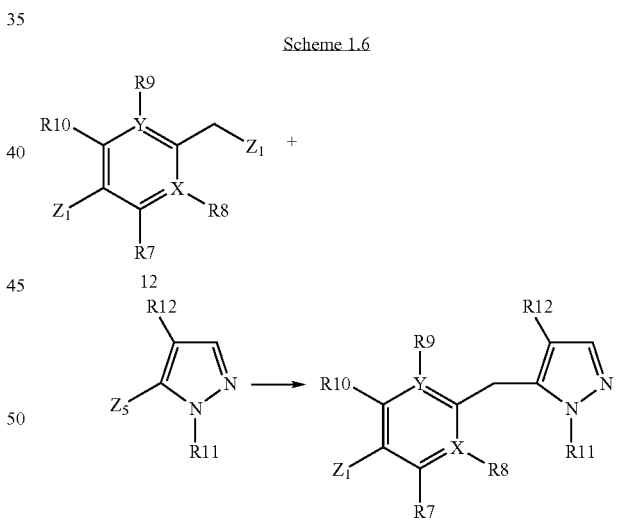

In Scheme 1.6 compounds such as 6 wherein $Z_5$ is a boronic acid, and $Z_1$ is a leaving group or coupling partner as defined above such as a halogen or triflate may be prepared by reacting a compound such as 12 with a compound such as 9 under palladium mediated coupling conditions known in the literature and described previously. Other conditions to effect this transformation are known in the literature such as Journal of Heterocyclic Chemistry, 24(6), 1669-75, 1987 and Tetrahedron Letters, 46(9), 1501-1504, 2005 and references cited therein.

Intermediates such as 6 L is a bond may be produced by the following procedures.

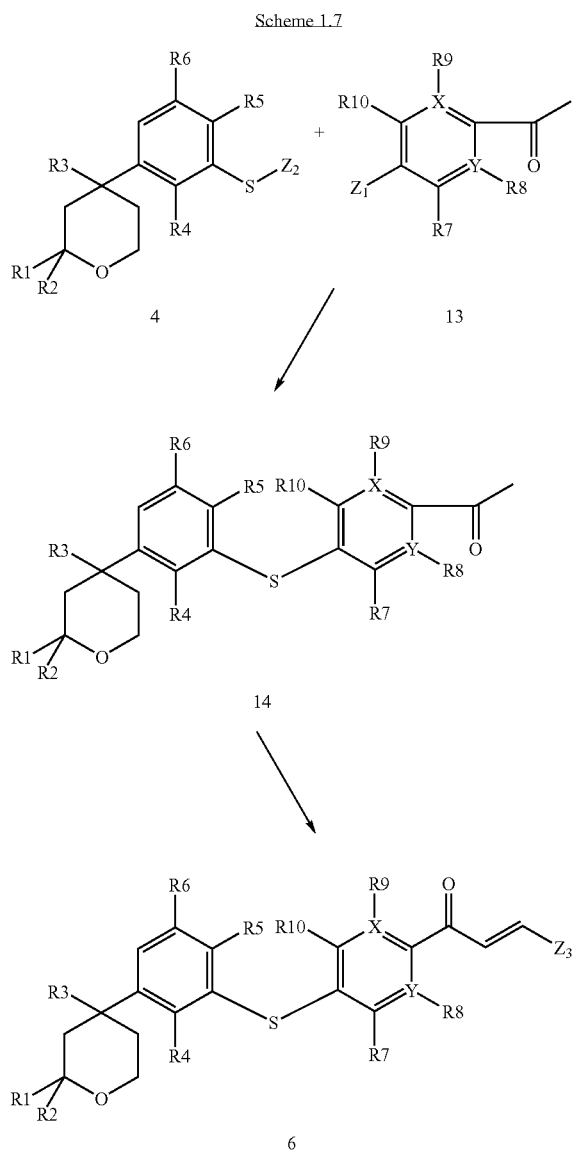

In Scheme 1.7 compounds such as 4 wherein $Z_2$ is a protecting group as defined above, such as triisopropylsilyl, are reacted with compounds such as 13 wherein $Z_1$ is a leaving group as defined above, such as halo, in a solvent such as toluene, THF or DMF with the addition of a base such as potassium t-butoxide, sodium hydride, or sodium bis(trimethylsilyl)amide. Additional excipients such as tetraethylammonium chloride may also be added. Reactions may be carried out at a range of temperatures from 25-110° C. to produce compounds such as 14. Compounds such as 14 may be further elaborated to compounds such as 6 wherein $Z_3$ is a leaving group as defined above, such as dimethylamino or alkoxy, in a solvent such as DMF or THF with the addition of N,N-dimethyl dimethyl acetal or trialkoxy orthoformate. Reactions may be carried out at a range of temperatures from 25-110° C.

Intermediates such as 5 L is a bond may be produced by the following procedures

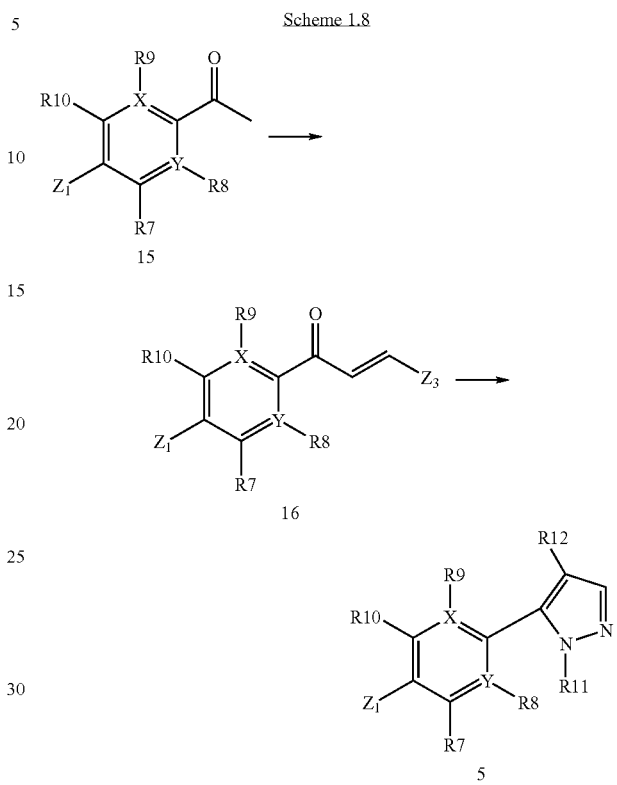

In scheme 1.8 compounds such as 5 wherein $Z_1$ is a leaving group or coupling partner as defined above such as a halogen or triflate may be prepared using procedures described for the preparation of intermediates 6 and products of 6 and 7.

Intermediates such as 4 may be produced by the following procedures.

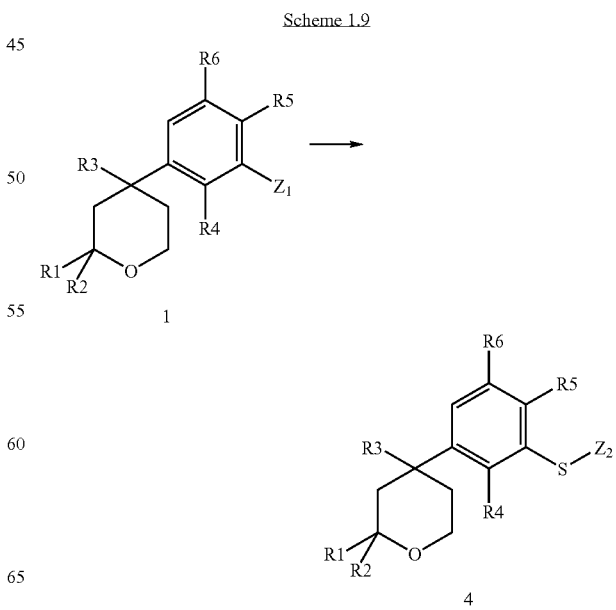

In Scheme 1.9 Compounds such as 1 wherein $Z_1$ is a coupling partner as defined above such as a halogen or triflate and $Z_2$ is a protecting group as defined above such as triisopropylsilyl, is reacted with a thiol source such as triisopropylsilane thiol in a solvent such as dioxane, THF, toluene, or ether. A base, catalyst or other excipient may be added. Examples include 1,1-bis(diisopropylphosphino)ferrocene, 1,1'-bis(diphenylphosphino)ferrocene palladium dichloride dichloromethane adduct, tetrakis(triphenylphosphine) palladium, PdCl2(diphenyl-phosphino ferrocene), sodium t-butoxide or sodium hydride. Anhydrous conditions and elevated temperatures may also be employed in the reaction. Additional examples may be found in Organic Letters, 9(20), 4081-4083, 2007; Journal of Medicinal Chemistry, 50 (16) 3954-3963, 2007; Advanced Synthesis & Catalysis, 347 (2+3), 313-319, 2005; Tetrahedron Letters, 47(16), 2675-2678, 2006; Journal of the American Chemical Society, 128(7), 2180-2181, 2006; European Journal of Organic Chemistry, (16), 2630-2642, 2007; Tetrahedron Letters, 48(17), 3033-3037, 2007; Tetrahedron Letters, 44(35), 6699-6702, 2003 and references cited therein.

Intermediates such as 8 may be produced by the following procedures.

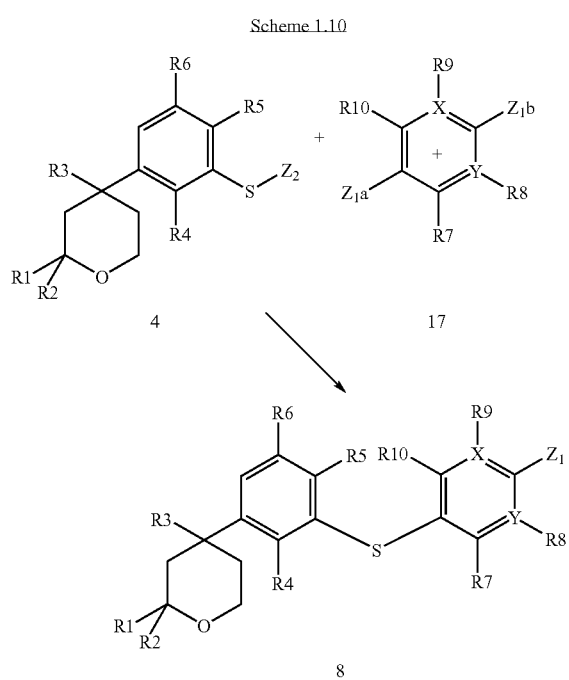

Scheme 1.10

In Scheme 1.10 compounds such as 4 wherein $Z_2$ is a protecting group as defined above such as triisopropylsilyl are reacted with compounds such as 17 wherein $Z_1a$ is a leaving group or coupling partner such as halo or triflate and $Z_1b$ is a leaving group or coupling partner such as halo or triflate such that $Z_1a$ is more reactive than $Z_1b$ to produce compounds such as 8 using a nucleophyllic displacement reaction or a palladium meditated coupling reaction as appropriate for the desired substitution pattern. Additional examples of this synthetic strategy may be found in the literature such as Angewandte Chemie, International Edition, 44(39), 6348-6354, 2005; Journal of Medicinal Chemistry, 49(10), 3012-3018, 2006; Chemistry—A European Journal, 13(28), 8051-8060, 2007; Chemistry—A European Journal, 13(18), 5100-5105, 2007; Tetrahedron Letters, 47(50), 8973-8976, 2006 and references cited therein.

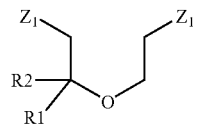

In addition to the methods shown in the examples, intermediates such as 11 wherein $Z_1$ is a leaving group as defined above such as halo, mesyl, or tosyl and may be produced by procedures known in the literature such as Journal fuer Praktische Chemie (Leipzig), 328 (5-6), 797-804, 1986; Journal of Organic Chemistry, 50(19), 3453-7, 1985; Journal fuer Praktische Chemie (Leipzig), 325(5), 719-28, 1983; Journal of Organic Chemistry, 48(20), 3412-22, 1983; Journal of Physical Organic Chemistry, 16(3), 175-182, 2003 and references cited therein.

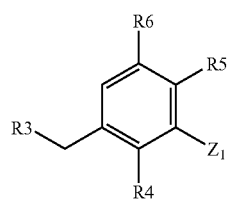

In addition to the methods shown in the examples, intermediates such as 10 may be produced by procedures known in the literature such as Tetrahedron Letters, 44(14), 2903-2905, 2003; U.S., 487-4764, 17 Oct. 1989; Journal of Combinatorial Chemistry, 4(4), 329-344, 2002; Heterocycles, 51(4), 737-750, 1999; Journal of Medicinal Chemistry, 31(5), 1005-9, 1988 and references cited therein.

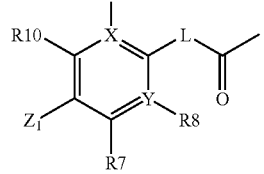

Intermediates such as 13 wherein $Z_1$ is a coupling partner as defined above such as halo or triflate are commercially available or may be produced by procedures known in the literature.

Schemes 1.0 to 1.10 as well as the preparation of all the intermediates involved are implemented in the examples enclosed with the present application.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Tosylate salt is preferred.

In a preferred embodiment of the invention, the compound is a 1:1 molar ratio salt of (2S,4R)-4-(2-fluoro-3-{[4-(1-methyl-1H-pyrazol-5-yl)phenyl]thio}phenyl)-2-methyltetrahydro-2H-pyran-4-carbonitrile and para-toluenesulfonic acid Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
  (i) by reacting the compound of formula (I) with the desired acid or base;
  (ii) by removing an acid- or base-labile protecting group from a suitable precursor of the compound of formula (I) or by ring-opening a suitable cyclic precursor, for example, a lactone or lactam, using the desired acid or base; or
  (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

A preferred compound of the invention is a crystalline form of a 1:1 molar ratio salt of (2S,4R)-4-(2-fluoro-3-{[4-(1-methyl-1H-pyrazol-5-yl)phenyl]thio}phenyl)-2-methyltetrahydro-2H-pyran-4-carbonitrile and para-toluenesulfonic acid, or a pharmaceutically acceptable solvate thereof.

Preferably, such crystalline form has an X-ray diffraction pattern with the following principal x-ray diffraction pattern peaks expressed in terms of 2-theta angle (±0.1 degrees) when measured using Cu Kα$_1$ radiation. (Wavelength=1.5406 Å)

| Angle 2-Theta ° |
| --- |
| 13.5 |
| 14.2 |
| 18.9 |
| 23.3 |
| 24.5 |

More preferably, such crystalline form has an X-ray diffraction pattern with the following principal x-ray diffraction pattern peaks expressed in terms of 2-theta angle when measured using Cu Kα$_1$ radiation (Wavelength=1.5406 Å):

| Angle 2-Theta ° |
| --- |
| 8.5 |
| 13.5 |
| 14.2 |
| 18.9 |
| 23.3 |
| 24.5 |
| 26.6 |

A preferred compound of the invention is a crystalline form of a 1:1 molar ratio salt of (2S,4R)-4-(2-fluoro-3-{[4-(1-methyl-1H-pyrazol-5-yl)phenyl]thio}phenyl)-2-methyltetrahydro-2H-pyran-4-carbonitrile and para-toluenesulfonic acid, having any one of the two X-ray diffraction patterns above and a melting point endotherm peak at about 132.7° C. in a TGA/SDTA trace, or a pharmaceutically acceptable solvate thereof, The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include, where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by (C$_1$-C$_{10}$)alkanoyl.

Further examples of replacement groups in accordance with the foregoing examples and examples of other prodrug types may be found in the aforementioned references.

Moreover, certain compounds of formula (I) may themselves act as prodrugs of other compounds of formula 1.

Also included within the scope of the invention are metabolites of compounds of formula (I), that is, compounds formed in vivo upon administration of the drug. Some examples of metabolites in accordance with the invention include (i) where the compound of formula (I) contains a methyl group, an hydroxymethyl derivative thereof (—CH$_3$—> —CH$_2$OH):

(ii) where the compound of formula (I) contains an alkoxy group, an hydroxy derivative thereof (—OR—>—OH);

(iii) where the compound of formula (I) contains a tertiary amino group, a secondary amino derivative thereof (—NR$^1$R$^2$—>—NHR$^1$ or —NHR$^2$);

(iv) where the compound of formula (I) contains a secondary amino group, a primary derivative thereof (—NHR$^1$—>—NH$_2$); and (v) where the compound of formula (I) contains an amide group, a carboxylic acid derivative thereof (—CONH$_2$—>COOH).

Compounds of formula (I) containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture, see, for example, *Chromatography and Separation Science* by Satinder Ahuja (Academic Press, 2003); *Chiral Separation Techniques: A Practical Approach*, 3$^{rd}$ by Ganaphthy Subramanian (Wiley, 2007).

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F., $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) can be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention such as for example diluents, carriers and adjuvants. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula 1, a film-forming polymer, a binder, a solvent, a humectant, a plasticizer, a stabilizer or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from the group consisting of natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurized container, pump, spray, atomizer (preferably an atomizer using electro hydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electro hydrodynamics to produce a fine mist may contain from 1 μg to 20 mg of the compound of the invention per actuation and the actuation volume may vary from 1 μl to 100 μl. A typical formulation may comprise a compound of formula I, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (I). The overall daily dose will typically be in the range 0.001 mg to 40 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of a compound of the invention is typically in the range of 0.01 mg to 2000 mg depending, of course, on the mode of administration. In another embodiment of the present invention, the total daily dose of a compound of the invention is typically in the range of 0.1 mg to 500 mg. In yet another embodiment of the present invention, the total daily dose of a compound of the invention is typically in the range of 1 mg to 300 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

It has now been found that a compound of formula (I) or a pharmaceutically acceptable salt or solvate thereof, either alone or in combination with one or more active agents, is particularly useful for the treatment of a 5-LO mediated disease, disorder, or condition.

According to a preferred embodiment, the 5-LO mediated disease, disorder, or condition refers to allergic and non-allergic airway diseases, disorders, or conditions.

Examples of allergic and non-allergic airway diseases, disorders, or conditions include the diseases, disorders and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

According to another embodiment, 5-LO mediated diseases further include those listed in Table I:

TABLE I (a) inflammation, including but not limited to smoke-induced airway inflammation and inflammation enhanced cough;
(b) arthritis, such as rheumatoid arthritis, spondyloarthropathies, systemic lupus erythematosus arthritis, juvenile arthritis, osteoarthritis, and gouty arthritis;
(c) neuroinflammation;
(d) pain (i.e., use of the compounds as analgesics), such as nociceptive or neuropathic pain;
(e) fever (i.e., use of the compounds as antipyretics);
(f) pulmonary sarcoisosis, and silicosis;
(g) cardiovascular diseases, such as atherosclerosis, myocardial infarction (such as post-myocardial infarction indication) thrombosis, congestive heart failure, cardiac reperfusion injury, and complications associated with hypertension and/or heart failure such as vascular organ damage;
(h) cardiomyopathy;
(i) stroke, such as ischemic and hemorrhagic stroke;
(j) ischemia, such as brain ischemia and ischemia resulting from cardiac/coronary bypass or ischemia induced myocardial injury;
(k) reperfusion injury including post-ischemic reperfusion injury;
(l) renal reperfusion injury;
(m) brain edema or brain injury;
(n) neurotrauma and brain trauma, such as closed head injury;
(o) neurodegenerative disorders;
(p) central nervous system disorders (these include, for example, disorders having an inflammatory or apoptotic component), such as Alzheimer's disease, Parkinson's disease, Huntington's Disease, amyotrophic lateral sclerosis, myasthenia gravis, spinal cord injury, and peripheral neuropathy;
(q) liver disease;
(r) hypercholesterolemia and dyslipidemias;
(s) gastrointestinal conditions including gastritis, gastric varices, inflammatory bowel disease, Crohn's disease, gastritis, irritable bowel syndrome, and ulcerative diseases including ulcerative colitis and gastric ulcer;
(t) nephritis;
(u) ophthalmic diseases, such as retinitis, retinopathies (such as diabetic retinopathy), uveitis, ocular photophobia, nonglaucomatous optic nerve atrophy, and age-related macular degeneration (ARMD) (such as ARMD-atrophic form);
(v) ophthalmological conditions, such as corneal graft rejection, ocular neovascularization, retinal neovascularization (such as neovascularization following injury or infection) and retrolental fibroplasia;
(w) glaucoma, such as primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation, and corticosteroid-induced glaucoma;
(x) acute injury to the eye tissue and ocular traumas, such as post-traumatic glaucoma, traumatic optic neuropathy, and central retinal artery occlusion (CRAO);
(y) diabetes including type I diabetes and type II diabetes;
(z) diabetic nephropathy;
(aa) skin-related conditions, such as psoriasis, eczema, burns, dermatitis, keloid formation, scar tissue formation, scleroderma and angiogenic disorders;
(bb) viral and bacterial infections, such as sepsis, septic shock, gram negative sepsis, malaria, meningitis, opportunistic infections, cachexia secondary to infection or malignancy, cachexia secondary to acquired immune deficiency syndrome (AIDS), AIDS, ARC (AIDS related complex), pneumonia, herpes simplex infections, rhinovirus infections, and herpes virus;
(cc) myalgias due to infection;
(dd) influenza;

TABLE I-continued (ee) endotoxic shock;
(ff) toxic shock syndrome;
(gg) autoimmune disease, such as graft vs. host reaction and allograft rejections;
(hh) bone resorption diseases, such as osteoporosis;
(ii) multiple sclerosis;
(jj) disorders of the female reproductive system, such as endometriosis, menstrual cramps, vaginitis and candidiasis;
(kk) pathological, but non-malignant, conditions, such as haemangiomas (such as infantile haemangiomas), angiofibroma of the nasopharynx, and avascular necrosis of bone;
(mm) benign and malignant tumors/neoplasia including cancer of any kind, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer, skin cancer such as squamus cell and basal cell cancers, prostate cancer, renal cell carcinoma, Hodgkin's disease, and other known cancers that affect epithelial cells throughout the body;
(nn) systemic lupus erthrematosis (SLE);
(oo) angiogenesis including neoplasia;
(pp) metastasis;
(qq) a fibrotic disease;
(rr) hemorrhage;
(ss) coagulation;
(tt) acute phase responses like those seen with infections and sepsis and during shock (e.g.,
(uu) septic shock, hemodynamic shock, etc.);
(vv) anorexia;
(ww) mycobacterial infection;
(xx) pseudorabies;
(yy) rhinotracheitis;
(zz) HIV;
(aaa) sarcoidosis;
(bbb) herpes virus, including herpes simplex virus type-1 (HSV-1), herpes simplex virus type-2 (HSV-2);
(ccc) cytomegalovirus (CMV);
(ddd) varicella-zoster virus (VZV);
(eee) Epstein-Barr virus;
(fff) human herpesvirus-6 (HHV-6);
(ggg) human herpesvirus-7 (HHV-7), human herpesvirus-8 (HHV-8);
(hhh) myogenesis;
(iii) mucin overproduction, and/or mucus hypersecretion;
(jjj) allergy, including allergic rhinitis;
(kkk) tissue destruction;
(lll) signs and symptoms such as breathless cough;
(mmm) disorders of the blood including aplastic anemia;
(nnn) spondyloarthopathies including lumbar spondylanhrosis and lumbar spondylarthrosis;
(ooo) disorders of the male reproductive system;
(ppp) headache pain including migraine headache pain, sinus headache pain, and tension headache pain;
(qqq) dental pain;
(rrr) rheumatic fever;
(sss) connective tissue injuries or disorders;
(ttt) obesity;
(uuu) pulmonary disorders and diseases (e.g., hyperoxic alveolar injury);
(vvv) a kidney stone;
(www) wound healing;
(xxx) a minor injury;
(yyy) radiation damage;
(zzz) bursitis;
(aaaa) vascular diseases;
(bbbb) pulmonary edema;
(cccc) conjunctivitis;
(dddd) tendinitis;
(eeee) cortical dementias;
(ffff) gingivitis;
(gggg) swelling occurring after injury;
(hhhh) periarteritis nodosa;
(iiii) thyroiditis;
(kkkk) polymyositis;
(llll) Behcet's syndrome;
(mmmm) nephritic syndrome;
(nnnn) hypersensitivity, and
(oooo) cognitive disorders, including mild cognitive impairment and cognitive deficits of schizophrenia, bipolar disorder, and ADHD.

In another preferred embodiment, the 5-LO mediated disease, disorder, or condition refers to pain. Pain may include nociceptive or neuropathic pain. In this embodiment, the additional active agent(s) may include a GABA analog such as gabapentin or pregabalin, an opiod such as morphine, a non-steroidal anti-inflammatory (NSAID), a COX-2 inhibitor, a steroid or a modulator of the eicosanoid pathway.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

In another preferred embodiment, the 5-LO mediated disease, disorder, or condition refers to pathological hepatic conditions. Hepatic conditions may include, for example, cirrhosis of the liver, fatty liver, hepatitis, nonalcoholic steatohepatitis (NASH), liver fibrosis, benign hepatic tumors and the like. In this embodiment, the additional active agent(s) may be antivirals, peroxisome proliferator-activated receptor (PPAR)-γ ligands such as thiazolidinediones, transforming growth factor β inhibitors and the like.

In another preferred embodiment, the 5-LO mediated disease, disorder, or condition refers to osteoporosis.

In another preferred embodiment, the 5-LO mediated disease, disorder, or condition refers to a metabolic syndrome.

In another preferred embodiment, the 5-LO mediated disease, disorder, or condition refers to pathologically high cholesterol. In this embodiment, the additional active agent(s) may be cholesterol modifying or modulating agents. Examples of cholesterol modifying or modulating agents include but are not limited to, HMG-CoA reductase inhibitors (or "statins") such as lovastatin (Mevacor), atorvastatin (Lipitor), pravastatin (Pravachol), and simvastatin (Zocor); squalene monooxygenase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; and LDL (low density lipoprotein) receptor inducers.

In another preferred embodiment, the 5-LO mediated disease, disorder, or condition refers to a cardiovascular condition. In this embodiment, the additional active agent(s) may be mineralcorticoid receptor modulators, such as eplerenone or spironolactone, an angiotensin converting enzyme (ACE) inhibitor such as quinapril (Accupril) or fosinopril (Monopril); an angiotensin receptor antagonist; vitamin B-6 (also known as pyridoxine) and the pharmaceutically acceptable salts thereof such as the HCl salt; vitamin B-12 (also known as cyanocobalamin); β-adrenergic receptor blockers; folic acid or a pharmaceutically acceptable salt or ester thereof such as the sodium salt and the methylglucamine salt; and anti-oxidant vitamins such as vitamin C and E and beta carotene.

In another preferred embodiment, the 5-LO mediated disease, disorder, or condition refers to a neoplasia. In this embodiment, the additional active agent(s) may be lpha-difluoromethylomithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B.

Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkeli APD, aphidicolin glycinate, asparaginase, Avarol, baccharin, batracylin, benfluoron, benzotript, Ipsen-Beaufour BIM-23015, bisantrene, Bristo-Myers BMY40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin 1, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastne, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid may be administered with the compounds of the present invention.

In another preferred embodiment, the 5-LO mediated disease, disorder, or condition refers to a neurodegenerative disease, in particular Alzheimers disease.

Besides being useful for human treatment, compounds of the present invention are also useful for veterinary treatment of companion animals, exotic animals and farm animals, including mammals for the treatment of a 5-LO mediated disease, disorder or condition disclosed in the present disclosure. As a matter of example, the compounds of the present invention are useful for the treatment of a 5-LO mediated disease, disorder, or condition in a horse, dog, or cat.

In another aspect, the present invention relates to a combination particularly for treating a 5-LO-mediated disease, disorder or condition, said combination comprising a compound of formula (I), or a pharmaceutically acceptable salt or solvate thereof, and one or more additional therapeutic agents. The combinations of the invention may further contain one or more pharmaceutically acceptable excipients.

The therapeutic agents of a combination of the invention can be co-administered to a patient to obtain some particularly desired therapeutic end result such as the treatment of any one or more of the diseases, disorders, or conditions mentioned above, e.g. those listed in Table I.

As used herein, the terms "co-administration", "co-administered" and "in combination with", referring to the compounds of the invention and one or more other therapeutic agents, is intended to mean, and does refer to and include the following:

simultaneous administration of such combination of compound(s) of the invention) and therapeutic agent(s) to a patient in need of treatment, when such components are formulated together into a single dosage form which releases said components at substantially the same time to said patient, substantially simultaneous administration of such combination of compound(s) of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of the invention and therapeutic agent(s) to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

Suitable examples of therapeutic agents which may be used in combination with a compound of the invention, or a pharmaceutically acceptable salt, solvate or composition thereof, include those of Table II below. Among the numerous therapeutic agents that may be co-administered with the compounds of this invention, are one or more 5-LO inhibitors known in the art.

TABLE II (a) 5-lipoxygenase activating protein (FLAP) antagonists;
(b) Leukotriene antagonists (LTRAs) including antagonists of $LTB_4$, $LTC_4$, $LTD_4$, and $LTE_4$;
(c) Histamine receptor antagonists including H1 and H3 antagonists;
(d) $\alpha_1$- and $\alpha_2$-adrenoceptor agonist vasoconstrictor sympathomimetic agents for decongestant use;
(e) muscarinic M3 receptor antagonists or anticholinergic agents;
(f) PDE inhibitors, e.g. PDE3, PDE4 and PDE5 inhibitors, such as theophylline;
(g) Sodium cromoglycate;
(h) COX inhibitors both non-selective and selective COX-1 or COX-2 inhibitors (such as NSAIDs);
(i) glucocorticosteroids or DAGR (dissociated agonists of the corticoid receptor);
(j) Monoclonal antibodies active against endogenous inflammatory entities;
(k) β2 agonists, including long-acting β2 agonists;
(l) Integrin antagonists;
(m) Adhesion molecule inhibitors including VLA-4 antagonists;
(n) Kinin-$B_1$- and $B_2$-receptor antagonists;
(o) Immunosuppressive agents, including inhibitors of the IgE pathway, and cyclosporin;
(p) Inhibitors of matrix metalloproteases (MMPs), e.g., MMP9, and MMP12;
(q) Tachykinin $NK_1$, $NK_2$ and $NK_3$ receptor antagonists;
(r) Protease inhibitors, e.g., elastase;
(s) Adenosine A2a receptor agonists and A2b antagonists;
(t) Inhibitors of urokinase;
(u) Compounds that act on dopamine receptors, e.g. D2 agonists;
(v) Modulators of the NFκB pathway, e.g. IKK inhibitors;
(w) modulators of cytokine signaling pathways such as syk kinase, JAK kinase inhibitors, p38 kinase, EGF-R or MK-2;
(x) Agents that can be classed as mucolytics or anti-tussive, and mucokinetics;
(y) Antibiotics;
(z) Antivirals;
(aa) Vaccines;
(bb) Chemokines;
(cc) Epithelial sodium channel (ENaC) blockers or Epithelial sodium channel (ENaC) inhibitors;
(dd) P2Y2 Agonists and other Nucleotide receptor agonists;
(ee) Inhibitors of thromboxane;
(ff) Niacin;
(gg) Inhibitors of $PGD_2$ synthesis and $PGD_2$ receptors (DP1 and DP2/CRTH2);
(hh) Adhesion factors including VLAM, ICAM, and ELAM;
(ii) Statins or other treatments for hypercholesterolemia; cholesterol and lipid absorption inhibitors (e.g., nicotinic acid, niacin, cholesterol transporters)
(jj) Diuretics;
(kk) Calcium channel blockers.

In one embodiment, the combination of the invention comprises a compound of formula (I) or a pharmaceutically acceptable salt or solvate thereof, and any one of the compounds listed in Table II for the treatment of a 5-LO mediated disease, disorder, or condition. According to another embodiment of the invention, said 5-LO mediated diseases, disorder or condition is selected from those listed in Table I.

In a highly preferred embodiment, a combination of the invention comprises a compound of formula (I) or a pharmaceutically acceptable salt or solvate thereof, and a glucocorticosteroid or a DAGR (dissociated agonist of the glucocorticoid receptor). Examples of Glucocorticosteroids include, but are not limited to, prednisone, prednisolone, flunisolide, triamcinolone acetonide, bechlometasone dipropionate, budesonide, fluticasone propionate, ciclesonide and mometasone furoate. Examples of DAGR compounds useful in combination with compounds of the present invention include, but are not limited to, those described in international patent application publications WO/2000/06522 and WO/2004/005229.

In a highly preferred embodiment, a combination of the invention comprises a compound of formula (I) or a pharmaceutically acceptable salt or solvate thereof, and a COX inhibitor, either non-selective or selective COX-1 or COX-2 inhibitors (NSAIDs) such as ibuprofen or celecoxib, or a pharmaceutically acceptable salt thereof.

In a highly preferred embodiment, a combination of the invention comprises a compound of formula (I) or a pharmaceutically acceptable salt or solvate thereof, and a β2 agonist. Examples of β2 agonists include, but are not limited to, salmeterol, formeterol, QAB-149 and carmoterol.

In a highly preferred embodiment, a combination of the invention comprises a compound of formula (I) or a pharmaceutically acceptable salt or solvate thereof, and a muscarinic M3 receptor antagonist or an anticholinergic agent. Examples of M3 receptor antagonists include, but are not limited to, tiotropium, ipatropium, oxitropium, perenzepine, tiospium, aclidinium and telenzepine.

In a highly preferred embodiment, a combination of the invention comprises a compound of formula (I) or a pharmaceutically acceptable salt or solvate thereof, and a histamine receptor antagonist, a examples of which includes an H1, H3 or H4 antagonist.

In a different embodiment, a combination of the invention comprises a compound of formula (I) or a pharmaceutically acceptable salt or solvate thereof, and a diuretic. The diuretic may be selected from several known classes, such as thiazides and related sulfonamides, potassium-sparing diuretics, loop diuretics and organo mercurial diuretics. Nonlimiting examples of thiazides are bendroflumethiazide, benzthiazide, chlorothiazide, cyclothiazide, hydrochlorothiazide, hydroflumethiazide, methylclothiazide, polythiazide and trichloromethiazide. Nonlimiting examples of potassium-sparing diuretics are triameterene and amiloride. Nonlimiting examples of loop diuretics, i.e. diuretics acting on the ascending limb of the loop of Henle of the kidney, are torsemide, bumetanide, furosemide and ethynacrylic acid. Nonlimiting examples or organo mercurial diuretics are mercaptomerin sodium, merethoxylline, procaine and mersalyl with theophylline.

In a different embodiment, a combination of the invention comprises a compound of formula (I) or a pharmaceutically acceptable salt or solvate thereof, and a calcium channel blocker. In one embodiment, the calcium channel blocker is selected from the group consisting of felodipine, amlodipine, nifedipine, verapamil HCl, nicardipine HCl, diltiazem HCl, aranidipine, atosiban, barnidipine, buflomedil, cilnidipine, docosahexaenoic acid, efonidipine HCl, fasudil, isradipine, lacidipine, lercanidipine, lomerizine, manidipine, nifelan, nilvadipine, nimodipine, Teczem, verelan, plendil, nisoldipine, nitrendipine, mebefradil and bepridil HCl. In another embodiment, the calcium channel blocker is selected from the group consisting of NS-7, NW-1015, SB-237376, SL-34.0829-08, terodiline, R-verapamil, bisaramil, CAI, ipenoxazone, JTV-519, S-312d, SD-3212, tamolarizine, TA-993, vintoperol, YM-430, CHF-1521, elgodipine, furnidipine, L651582, oxodipine, ranolazine, AE-0047, azelnidipine, dotarizine, lemildipine, pranidipine, semotiadil, temiverine HCl, tenosal, vatanidipine HCl and ziconotide.

The following examples illustrate the preparation of the intermediates and compounds of the formula (I).

PREPARATIONS

Intermediate 1

4-(3-bromophenyl)-tetrahydro-2H-pyran-4-carboxamide 4-(3-bromophenyl)tetrahydro-2H-pyran-4-carbonitrile made by the procedures described in EP 1081144 (1.05 kg, 3.95 mole) was stirred in 98% $H_2SO_4$ (3.00 L) at room temperature for about 40 h. The mixture was then poured onto ice and the very fine suspension was filtered and washed with $H_2O$ thoroughly until pH of wash is neutral. The white solid was washed with hexanes and was then dried in vacuo at 35-40° C. to give 1119 g (99.8% yield) of product in 99.9% purity. LC/MS: 5%-100% CH3CN:H20-0.01% TFA gradient over 10 minutes: 4.68 min. (M+H)+. $^1$H NMR (400 MHz, DMSO-$d_6$) δ ppm 7.50-7.49 (m, 1H), 7.43-7.40 (m, 1H), 7.36-7.30 (m, 1H), 7.27 (d, J=7.92 Hz, 1H) 7.06 (s, 1H), 5.00 (brs, 1H) 3.71 (dt, J=11.7, 3.7 Hz, 2H), 3.42 (t, J=10.7 Hz, 2H), 2.38 (d, J=13.6 Hz, 2H), 1.75 (td, J=12.2, 4.3 Hz, 2H).

Intermediate 2

4-(3-(triisopropylsilylthio)phenyl)-tetrahydro-2H-pyran-4-carboxamide

Alternative 1
4-(3-Bromophenyl)-tetrahydro-2H-pyran-4-carboxamide prepared in step 1 (300 g (1.06 mole), sodium tert-butoxide (122 g, 1.27 mole), Pd(OAc)$_2$ (4.74 g 0.0211 mole) and DIPPF (1,1-bis(diisopropylphosphino)ferrocene) (10.6 g 0.0253 mole) were placed in a flask which was evacuated and filled with $N_2$ 3 times. Anhydrous dioxane (2.3 L) was added and the mixture was stirred at room temperature for 1 h. To the mixture was added triisopropylsilane thiol (221 g 1.16 mole) and the resulting mixture was heated to reflux. Reflux was stopped after 1 h and the mixture was allowed to cool to room temperature. The mixture was then poured into ethyl acetate (7 L) which was then washed with $H_2O$ (2×4 L) and brine (2 L). The combined aqueous washes were back extracted with ethyl acetate (3 L) which was then washed with $H_2O$ (2×2 L) and brine (1 L). The combined organic layers were dried over MgSO$_4$, filtered and concentrated to dryness. Ethyl acetate (0.5 L) was added to the solid and the mixture was stirred on the rotary evaporator to give a fine suspension. Hexanes (1.5 L) was then added and the suspension was allowed to stand for 1 hour. The solid was filtered, washed with 1:1 ethyl acetate-hexanes (1 L) and then hexanes. The resulting brown solid was dried in vacuo to give 334 g (80% yield) of the product in 99% purity. A second crop was obtained from the filtrate which was washed as before and dried to give an additional 15 g product for a total yield of 84%. LC/MS: 5%-100% CH3CN:H20-0.01% TFA gradient over 10 minutes: 9.35 min. 394.1 (M+H)+. $^1$H NMR (400 MHz, CDCl$_3$) δ ppm 7.52-7.51 (m, 1H) 7.42-7.39 (m, 1H), 7.22-7.21 (m, 2H), 5.35 (brs, 1H), 5.13 (brs, 1H) 3.78-3.75 (m, 4H) 2.36-2.32 (m, 2H), 2.06-2.00 (m, 2H), 1.27-1.16 (m, 3H), 1.05 (d, J=7.25 Hz, 18H).

Alternative 2
Purge a 3-neck flask (overhead stirrer, nitrogen inlet, serum cap) with nitrogen. Add 4-(3-Bromophenyl)-tetrahydro-2H-pyran-4-carboxamide prepared in step 1 (10 g, 0.03519 mole). Add sodium t-butoxide (4.1 g, 0.04223 moles). Add anhydrous toluene. Toluene should be as dry as possible, <0.01% water by KF is sufficient. Initiate stirring. Purge the reaction mixture with 4 vacuum/nitrogen purge cycles, maintaining 60 torr vacuum for 30 seconds with each cycle. Add the thiol (9.1 g, 0.04223 moles) assuring that oxygen is not introduced into the vessel. Heat to 75° C. Add PdCl2(diphenyl-phosphino ferrocene) (0.258 g, 0.00035 moles). Continue heating to reflux (reaction temperature about 107° C.) for a minimum of 1 hour. The mixture should reach reflux within 30 minutes.

Cool the reaction mixture to 25° C. Add ethyl acetate (300 mL, 30 mL/g) and stir the resulting suspension for 30 min. Filter the suspension through celite (30 g). Rinse the celite with ethyl acetate for rinse (100 mL, of product to be rinsed), combining filtrates. Concentrate the filtrate via vacuum distillation at 70 torr at 30° C. until 80% of the filtrate volume has been removed. Add hexane (200 mL, 20 mL/g of product to be crystallized) for crystallization to the slurry over 5 minutes. Stir and cool the mixture to 5° C. Maintain the mixture at 5° C. for a minimum of 1 hour. Isolate product by filtration. Rinse the cake with hexane (100 mL, of product to be rinsed). Dry the cake on the filter to LOD of no more than 5%. Dry the solid at 45-50° C. under vacuum to an LOD of no more than 1.5%. Yield 12 grams (85% yield). Any mL/g amount indicated above is referred to grams of bromo carboxamide.

Intermediate 3

5-(4-bromophenyl)-1-methyl-1H-pyrazole

Alternative 1
A N,N'-dimethylformamide (15 mL) solution of 4-bromoacetophenone (10.60 g, 53.25 mmols) and N,N'-dimethylformamide dimethyl acetal (2.5 equivalents) was heated at 125 degrees Celcius for 3 hours. The dark red solution was cooled to room temperature. The volatiles were removed by rotary evaporation providing a red viscous oil. To this substance was added anhydrous N,N'-dimethylformamide (15 mL) and methyl hydrazine (7.6 g, 160 mmols, 3 equivalents). The mixture was stirred at room temperature for 1 hour and then heated at 75 degrees Celcius for 4 hours. The volatiles were removed by rotary evaporation and the crude residue was taken up in a small volume of methylene chloride. This red solution was applied to a cartridge of silica gel. The cartridge was eluted with a 20:80 mixture of ethyl acetate and hexanes, respectively. The appropriate fractions were combined and concentrated to produce 12.5 g of a white solid.

1H NMR (400 MHz, CHLOROFORM-d) δ ppm 3.87-3.95 (m, J=2.22 Hz, 3H) 6.29-6.36 (m, 1H) 7.31 (dd, J=8.36 Hz, 2H) 7.52-7.56 (m, 1H) 7.62 (dd, J=2.05 Hz, 2H).

Alternative 2

4-bromoacetophenone (20.0 g; 0.10 mole) and N,N-dimethylformamide dimethylacetal (28.5 mL; 0.20 mole) were mixed together in DMF (12 mL) and heated to 110° C. for 4 hours. The methanol and water that were generated during the reaction were distilled (6.2 mL). The mixture was cooled to 25° C. Methyl t-butyl ether (100 mL) and methylhydrazine (21.2 mL; 0.40 moles) were added and the mixture was stirred over night. The reaction mixture was washed with 1M aqueous ammonium chloride (3×40 mL) and water (40 mL). The organic phase was dried by azeotropic distillation using a Dean-Stark apparatus. As an alternative to distillation, the solution was dried through an anhydrous magnesium sulfate cartridge. The solution was filtered through a silica gel cartridge (60 g). The product was flushed from the cartridge with methyl t-butyl ether. The fraction(s) containing product were combined and concentrated to about 70 mL by distillation. Heptane (120 mL) was added and distillation was continued until the pot temperature reached 98.4° C. About 100 mL of distillate was collected. The mixture was cooled to 40° C. The mixture was seeded and the temperature was maintained at 40° C. for 30 minutes while crystallization was initiated. The mixture was slowly chilled to 0° C. over 90 minutes. The mixture was held at 0° C. for 30 minutes. The mixture was filtered and the solid was washed (3×) with chilled (0° C.) heptane. The solid was dried on the filter. A cream-colored, crystalline solid (16.3 g; 68% yield) was obtained. The NMR data of the title compound are as per alternative 1.

Comparative example 1

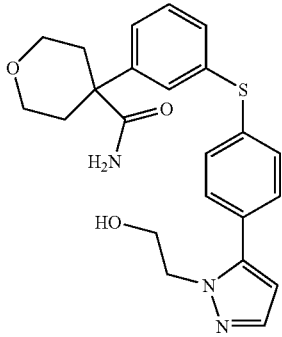

4-[3-({4-[1-(2-hydroxyethyl)-1H-pyrazol-5-yl]phenyl}thio)phenyl]tetrahydro-2H-pyran-4-carboxamide Step 1: Preparation of 4-{3-[(4-acetylphenyl)thio]phenyl}tetrahydro-2H-pyran-4-carboxamide 4-fluoroacetophenone (3.0 g, 21.7 mmols) and 4-{3-[(triisopropylsilyl)thio]phenyl}tetrahydro-2H-pyran-4-carboxamide (8.5 g, 21.7 mols) and tetraethylammonium hydrochloride (6.9 g, 42 mmols) were suspended in anhydrous toluene (50 ml) under an atmosphere of nitrogen. To this mixture was added 1.0 M potassium t-butoxide in THF (43 ml, 43 mmols). The stirring mixture was then heated at 80 degrees Celsius for 12 hours. The heterogeneous mixture was allowed to cool to room temperature. Ethyl acetate (100 ml), and 1.0 N HCl (aq) (43 ml) and water (50 ml) were added to the mixture. The layers were vigorously mixed stirred for one hour. The insoluble product was collected by suction filtration, washed with water and ethyl ether (4×50 ml) and dried under vacuum to afford a beige solid that was not purified further (4.80 g, 13.5 mmols, 62%). Reverse Phase LCMS M+H=356.2, Retention Time 3.03 min, 5% to 95% acetonitrile over 4 min., aqueous buffer with 0.1% TFA.

Step 2: Preparation of N-[(1E)-(dimethylamino)methylene]-4-[3-({4-[(2E)-3-(dimethylamino)prop-2-enoyl]phenyl}thio)phenyl]tetrahydro-2H-pyran-4-carboxamide 4-{3-[(4-acetylphenyl)thio]phenyl}tetrahydro-2H-pyran-4-carboxamide (3.5 g, 9.8 mmols) was added to anhydrous DMF (3 ml). Next, the dimethylacetal of DMF (3.5 g, 29 mmols) was added. The solution was then heated at 100 degrees Celsius for five hours. The volatiles were removed by rotary evaporation at reduced pressure to afford a dark red oil. The oil was dissolved in methylene chloride and applied to a column of silica gel. The column was eluted with a 1:1 Heptane/Ethyl acetate mixture, respectively. The fractions containing the product were combined and concentrated to provide a tan solid (2.8 g, 6.8 mmols, 69%). 1H NMR (400 MHz, DMSO-$d_6$) d ppm 1.69-1.82 (m, 2H) 2.52-2.59 (m, 2H) 2.85 (s, 3H) 2.91 (s, 3H) 3.08 (s, 3H) 3.15 (s, 3H) 3.36-3.47 (m, 2H) 3.67-3.83 (m, 2H) 5.81 (d, J=12.29 Hz, 1H) 7.22 (d, J=8.19 Hz, 2H) 7.25-7.30 (m, 1H) 7.34-7.42 (m, 2H) 7.44-7.50 (m, 1H) 7.72 (d, J=12.29 Hz, 1H) 7.84 (d, J=8.53 Hz, 2H) 8.35 (s, 1H)

Step 3: Preparation of 4-[3-({4-[1-(2-hydroxyethyl)-1H-pyrazol-5-yl]phenyl}thio)phenyl]tetrahydro-2H-pyran-4-carboxamide N-[(1E)-(dimethylamino)methylene]-4-[3-({4-[(2E)-3-(dimethylamino)prop-2-enoyl]phenyl}thio)phenyl]tetrahydro-2H-pyran-4-carboxamide (50 mg, 0.011 mmols) and 2-hydroxyethylhydrazine (152 mg, 1.0 mmols) were stirred in DMF (1 ml) at 80 degrees Celsius for twelve hours. The reaction mixture was cooled to room temperature and the volatiles were evaporated. The residue was dissolved in a small volume and DMSO and purified using reverse phase HPLC (acetonitile/water gradient). The fractions containing pure product were combined and concentrated to afford a white solid (21 mg, 45%) 1H NMR (400 MHz, DMSO-$d_6$) d ppm 1.71-1.86 (m, 2H) 2.38 (d, J=13.18 Hz, 2H) 3.38-3.51 (m, 2H) 3.63-3.80 (m, 4H) 4.08 (t, J=5.86 Hz, 2H) 4.84 (t, J=4.39 Hz, 1H) 6.33 (d, J=1.46 Hz, 1H) 7.00 (br. s., 1H) 7.22 (br. s., 1H) 7.26 (d, J=7.32 Hz, 1H) 7.32 (d, J=8.05 Hz, 2H)

7.36-7.41 (m, 2H) 7.45 (s, 1H) 7.47-7.50 (m, 1H) 7.52 (d, J=8.05 Hz, 2H). HRMS calc M+H: 424.1695, found: 424.1661.

Example 1

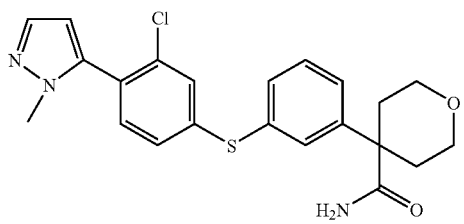

4-(3-{[3-chloro-4-(1-methyl-1H-pyrazol-5-yl)phenyl]thio}phenyl)tetrahydro-2H-pyran-4-carboxamide

Step 1: Preparation of 5-(4-bromo-2-chlorophenyl)-1-methyl-1H-pyrazole 0.379 gm of 4'-bromo-2'-chloroacetophenone (~95% pure) was placed under nitrogen and dissolved in 7.5 mL of anhydrous N,N-dimethyl formamide. 0.80 mL of dimethylformamide dimethyl acetal was added, and the mixture was refluxed for 30 minutes. The reflux condenser was then replaced with a distillation head, and the mixture was distilled until the distillation head temperature reached 150° C. The mixture was cooled to room temperature, 0.18 mL of methylhydrazine was added, and the mixture was refluxed for 30 minutes. The reaction mixture was cooled, diluted into diethyl ether, extracted 4 times with 5% aqueous sodium chloride, dried with magnesium sulfate, filtered, and flash chromatographed on silica gel to give 0.370 gm of a colorless oil. LCMS (M+H) 271; 1H NMR (400 MHz, DMSO-$d_6$) δ ppm 3.64 (s, 3H) 6.36 (d, J=1.88 Hz, 1H) 7.42 (d, J=8.32 Hz, 1H) 7.51 (d, J=1.88 Hz, 1H) 7.69 (dd, J=8.32, 1.88 Hz, 1H) 7.94 (d, J=1.88 Hz, 1H).

Step 2: Preparation of 4-(3-{[3-chloro-4-(1-methyl-1H-pyrazol-5-yl)phenyl]thio}phenyl)tetrahydro-2H-pyran-4-carboxamide 468.2 mg of 4-{3-[(triisopropylsilyl)thio]phenyl}tetrahydro-2H-pyran-4-carboxamide, 287.4 mg of 5-(4-bromo-2-chlorophenyl)-1-methyl-1H-pyrazole, 84.4 mg of tetrakis(triphenylphosphine)palladium, 37.7 mg of bis[(2-diphenylphosphino)phenyl]ether, 180.0 mg of cesium fluoride, and 191.1 mg of tetraethylammonium chloride monohydrate were placed in a septum-sealed vial and evacuated/nitrogen filled three times. 6 mL of anhydrous isopropanol was added, followed by the addition of 1.07 mL of 1.0 M potassium t-butoxide in tetrahydrofuran. The mixture was stirred at room temperature for 5 minutes and then heated at 80° C. for 40 minutes. The reaction mixture was cooled, diluted into ethyl acetate, extracted with 5% aqueous potassium carbonate, dried with magnesium sulfate, filtered and purified by flash chromatography to give 410.2 mg of product. HRMS (M+H) calc. 428.1199, found 428.1172; 1H NMR (400 MHz, DMSO-$d_6$) δ ppm 1.73-1.89 (m, 2H) 2.42 (d, J=13.43 Hz, 2H) 3.41-3.53 (m, 2H) 3.63 (s, 3H) 3.67-3.77 (m, 2H) 6.33 (d, J=2.15 Hz, 1H) 7.07 (s, 1H) 7.21 (dd, J=8.19, 2.01 Hz, 1H) 7.29 (s, 1H) 7.38 (d, J=1.88 Hz, 1H) 7.39-7.43 (m, 2H) 7.45-7.49 (m, 2H) 7.49 (d, J=1.88 Hz, 1H) 7.54 (s, 1H).

Example 2

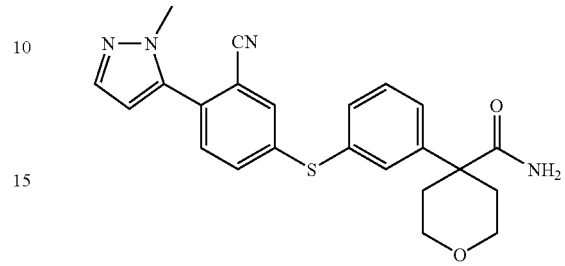

4-(3-{[3-Cyano-4-(1-methyl-1H-pyrazol-5-yl)phenyl]thio}phenyl)tetrahydro-2H-pyran-4-carboxamide

Step 1: Preparation of 5-bromo-2-(1-methyl-1H-pyrazol-5-yl)benzonitrile

5-Bromo-2-iodobenzonitrile (0.30 g, 1.0 mmol), (1-methyl-1H-pyrazol-5-yl)boronic acid (188 mg, 1.5 mmol), dichloro[1,1'-bis(diphenylphosphino)ferrocene] palladium (II) dichloromethane adduct (26 mg, 0.05 mmol) and cesium carbonate (651 mg, 2.00 mmol) were stirred together at 80 degrees Celsius in a solvent mixture of 3:1 dioxane/water (5 mL), respectively, for one hour. The reaction mixture was allowed to cool to room temperature and water (25 mL) and 1 N HCl (5 mL) were added. The product was extracted into methyene chloride. The organic mixture was concentrated by rotary evaporation to a small volume which was applied to a 40 g cartridge of silica gel. The cartridge was eluted with a 70:30 mixture of hexanes-acetone, respectively. The fractions containing the product were combined and concentrated to give a white solid as product. (210 mg, 80%)

Step 2: Preparation of 4-(3-{[3-cyano-4-(1-methyl-1H-pyrazol-5-yl)phenyl]thio}phenyl)tetrahydro-2H-pyran-4-carboxamide A mixture of 5-bromo-2-(1-methyl-1H-pyrazol-5-yl)benzonitrile (160 mg, 0.61 mmol), 4-{3-[(triisopropylsilyl)thio]phenyl}tetrahydro-2H-pyran-4-carboxamide (264 mg, 0.67 mmol), tetrakis(triphenylphosphine)palladium(0) (70 mg, 0061 mmol), bis[(2-diphenylphosphino)]phenyl ether (32.8 mg mg, 0.061 mmol), tetraethylammonium chloride monohydrate (251 mg, 1.52 mmol) and cesium carbonate (497 mg, 1.5 mmol) in anhydrous dioxane (5 mL) was heated for 4 hours at 90 degrees Celsius in an atmosphere of nitrogen. The reaction mixture was cooled to room temperature. 1 N HCl (4 mL) was added followed by water (20 mL). The mixture was extracted with methylene chloride (3×15 mL). The combined extracts were dried (sodium sulfate) and concentrated to provide the crude product mixture. The residue was dissolved in a small volume of methyene chloride and applied to a 120 g cartridge of silica gel. The product was eluted using a mixture of 6:4 methylene chloride/acetone, respectively. Product fractions were combined and evaporated to a give a light brown solid (70 mg, 27%). 1H NMR (400 MHz, DMSO-$d_6$) δ ppm 1.75-1.91 (m, 2H) 2.42 (d, J=13.54 Hz, 2H) 3.43-3.54 (m, 2H) 3.69-3.80 (m, 5H) 6.51 (s, 1H) 7.03 (br. s., 1H) 7.26 (br.

s., 1H) 7.39-7.44 (m, 1H) 7.46-7.57 (m, 5H) 7.58-7.66 (m, 1H) 7.77 (s, 1H); HRMS calc M+H: 419.1542, found 419.1534.

Compounds of examples 3-9 were made using the method described in comparative example 1 using the appropriate hydrazine starting materials.

Example 3

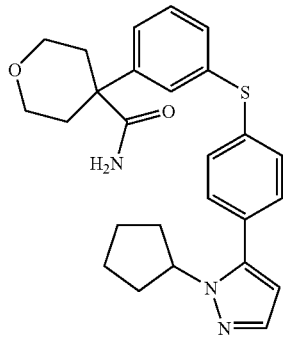

4-(3-{[4-(1-cyclopentyl-1H-pyrazol-5-yl)phenyl]thio}phenyl)tetrahydro-2H-pyran-4-carboxamide 1H NMR (400 MHz, DMSO-$d_6$) δ ppm 1.47-1.63 (m, 2H) 1.73-1.88 (m, 4H) 1.89-2.04 (m, 4H) 2.40 (d, J=13.54 Hz, 2H) 3.47 (s, 2H) 3.72 (d, J=11.35 Hz, 2H) 4.67 (t, J=7.14 Hz, 1H) 6.30 (d, J=1.46 Hz, 1H) 7.02 (br. s., 1H) 7.24 (br. s., 1H) 7.30 (d, J=6.59 Hz, 1H) 7.34-7.44 (m, 6H) 7.50 (d, J=1.46 Hz, 1H) 7.47 (s, 1H); HRMS calc M+H: 448.2059, found: 448.2028.

Example 4

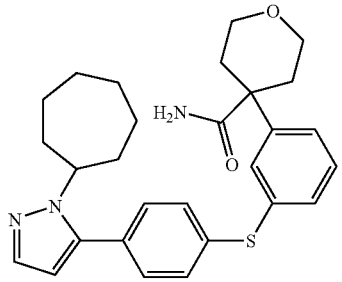

4-(3-{[4-(1-cycloheptyl-1H-pyrazol-5-yl)phenyl]thio}phenyl)tetrahydro-2H-pyran-4-carboxamide 1H NMR (400 MHz, DMSO-$d_6$) δ ppm 1.38 (br. s., 2H) 1.53 (br. s., 5H) 1.71 (br. s., 1H) 1.77 (d, J=4.03 Hz, 1H) 1.80 (br. s., 1H) 1.86 (d, J=19.40 Hz, 1H) 1.85 (d, J=7.69 Hz, 1H) 2.00 (t, J=10.25 Hz, 2H) 2.00 (d, J=19.76 Hz, 1H) 2.40 (d, J=13.54 Hz, 2H) 3.47 (s, 2H) 3.72 (d, J=11:71 Hz, 2H) 4.31 (d, J=4.76 Hz, 1H) 6.28 (d, J=1.46 Hz, 1H) 7.02 (br. s., 1H) 7.24 (br. s., 1H) 7.30 (d, J=6.59 Hz, 1H) 7.35-7.44 (m, 6H) 7.48 (d, J=8.42 Hz, 2H); HRMS calc M+H: 476.2372, found: 476.2369.

Example 5

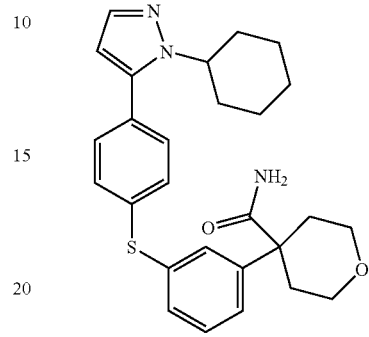

4-(3-{[4-(1-cyclohexyl-1H-pyrazol-5-yl)phenyl]thio}phenyl)tetrahydro-2H-pyran-4-carboxamide 1H NMR (400 MHz, DMSO-$d_6$) δ ppm 1.07-1.35 (m, 4H) 1.59 (d, J=11.71 Hz, 2H) 1.68-1.95 (m, 6H) 2.38 (d, J=13.36 Hz, 2H) 3.45 (t, J=10.70 Hz, 2H) 3.70 (d, J=11.71 Hz, 2H) 3.94-4.18 (m, 1H) 6.26 (s, 1H) 7.00 (br. S., 1H) 7.21 (br. S., 1H) 7.25-7.51 (m, 9H); HRMS calc M+H: 462.2215, found: 462.2215.

Example 6

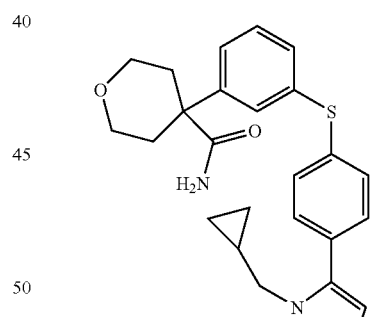

4-[3-({4-[1-(cyclopropylmethyl)-1H-pyrazol-5-yl]phenyl}thio)phenyl]tetrahydro-2H-pyran-4-carboxamide 1H NMR (400 MHz, DMSO-$d_6$) δ ppm 0.14 (q, J=4.88 Hz, 2H) 0.39 (d, J=6.59 Hz, 2H) 1.08 (br. s., 1H) 1.73-1.84 (m, 2H) 2.40 (d, J=13.54 Hz, 2H) 3.47 (br. s., 2H) 3.72 (d, J=11.35 Hz, 2H) 4.00 (d, J=6.95 Hz, 2H) 6.36 (d, J=1.46 Hz, 1H) 7.02 (br. s., 1H) 7.23 (br. s., 1H) 7.28 (d, J=6.59 Hz, 1H) 7.32-7.41 (m, 4H) 7.43-7.49 (m, 3H) 7.71-7.86 (m, 1H); HRMS calc M+H: 434.1902, found: 434.1908.

Example 7

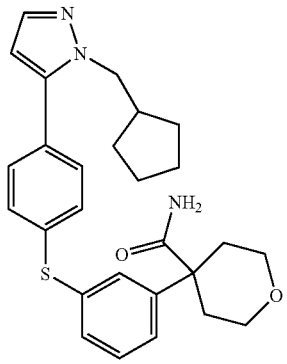

4-[3-({4-[1-(cyclopentylmethyl)-1H-pyrazol-5-yl]phenyl}thio)phenyl]tetrahydro-2H-pyran-4-carboxamide 1H NMR (400 MHz, DMSO-$d_6$) δ ppm 1.01-1.11 (m, 1H) 1.06 (d, J=5.86 Hz, 1H) 1.39-1.50 (m, 6H) 1.74-1.84 (m, 1H) 1.79 (t, J=10.25 Hz, 2H) 2.26 (d, J=7.32 Hz, 1H) 2.40 (d, J=13.54 Hz, 2H) 3.43-3.51 (m, 1H) 3.71 (d, J=11.71 Hz, 2H) 4.04 (d, J=7.32 Hz, 2H) 6.34 (d, J=1.46 Hz, 1H) 7.02 (br. s., 1H) 7.23 (br. s., 1H) 7.27 (d, J=6.22 Hz, 1H) 7.35-7.41 (m, 4H) 7.48 (d, J=1.83 Hz, 1H) 7.45 (d, J=8.42 Hz, 3H). HRMS calc M+H: 462.2215, found: 462.2208.

Example 8

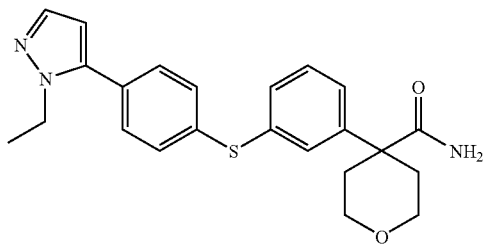

4-(3-{[4-(1-ethyl-1H-pyrazol-5-yl)phenyl]thio}phenyl)tetrahydro-2H-pyran-4-carboxamide 1H NMR (400 MHz, DMSO-$d_6$) δ ppm 1.27 (t, J=7.14 Hz, 3H) 1.68-1.86 (m, 2H) 2.38 (d, J=13.72 Hz, 2H) 3.45 (t, J=10.52 Hz, 2H) 3.70 (d, J=11.71 Hz, 2H) 4.09 (q, J=7.01 Hz, 2H) 7.00 (br. s., 1H) 7.12-7.52 (m, 11H); HRMS calc M+H: 408.1746, found: 408.1847.

Example 9

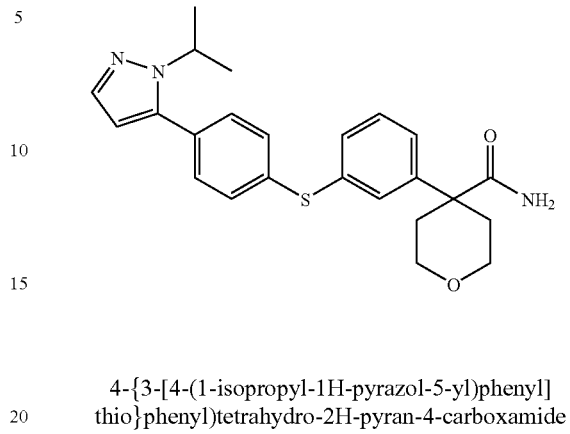

4-{3-[4-(1-isopropyl-1H-pyrazol-5-yl)phenyl]thio}phenyl)tetrahydro-2H-pyran-4-carboxamide 1H NMR (400 MHz, DMSO-$d_6$) δ ppm 1.34 (d, J=6.59 Hz, 6H) 1.78 (t, J=10.16 Hz, 2H) 2.38 (d, J=13.17 Hz, 2H) 3.45 (t, J=10.70 Hz, 2H) 3.70 (d, J=11.89 Hz, 2H) 4.39-4.55 (m, 1H) 7.00 (br. s., 1H) 7.16-7.53 (m, 11H); HRMS calc M+H: 422.1902, found: 422.2011.

Example 10

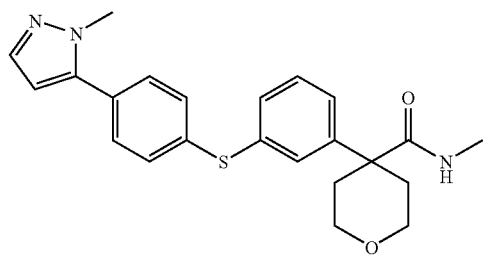

N-Methyl-4-(3-{[4-(1-methyl-1H-pyrazol-5-yl)phenyl]thio}phenyl)tetrahydro-2H-pyran-4-carboxamide 4-(3-{[4-(1-Methyl-1H-pyrazol-5-yl)phenyl]thio}phenyl)tetrahydro-2H-pyran-4-carboxamide (100 mg, 0.25 mmol) was suspended in anhydrous THF (10 mL). To this mixture was added sodium hydride (50% dispersion in mineral oil, 25 mg). The mixture was stirred for 30 minutes at room temperature then iodomethane (0.14 g, 1.0 mmol) was added. The mixture was then stirred overnight at ambient temperature. Water (2 mL) was then added slowly to the reaction mixture. The pH was adjusted to approximately 5 by the addition of 1 N HCl. The product was extracted into methylene chloride and purified using flash column chromatography with a mobile phase of 97:3 methylene chloride-methanol, respectively. The fractions containing the product were combined and concentrated to provide N-methyl-4-(3-{[4-(1-methyl-1H-pyrazol-5-yl)phenyl]thio}phenyl)tetrahydro-2H-pyran-4-carboxamide as a white solid (82 mg, 79%) 1H NMR (400 MHz, DMSO-$d_6$) δ ppm 1.78-1.89 (m, 2H) 2.38 (d, J=13.54 Hz, 2H) 3.38-3.50 (m, 2H) 3.66-3.75 (m, 2H) 3.84 (s, 3H) 6.41 (d, J=1.83 Hz, 1H) 7.24-7.31 (m, 1H) 7.32-7.43 (m, 5H)

7.46 (d, J=1.83 Hz, 1H) 7.52 (d, J=8.42 Hz, 2H) 7.58-7.66 (m, 1H); HRMS calc M+H: 408.1746, found 408.1815.

Example 11

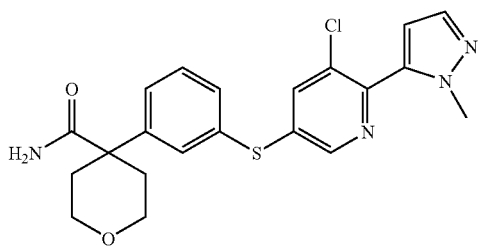

4-(3-{[5-chloro-6-(1-methyl-1H-pyrazol-5-yl)pyridin-3-yl]thio}phenyl)tetrahydro-2H-pyran-4-carboxamide Step 1: Preparation of 5-bromo-3-chloro-2-iodopyridine 1.11 g of 5-bromo-2,3-dichloropyridine was placed under nitrogen in a dried vial and dissolved in 12 ml of anhydrous 1,2-dichloroethane. 0.862 mL of iodotrimethylsilane was added, and the solution was heated at 80° C. for 3 days. The reaction was cooled, diluted into ethyl acetate, extracted with saturated aqueous potassium carbonate, extracted with aqueous ~0.5% sodium metabisulfite, dried with magnesium sulfate, filtered, concentrated, and purified by reverse phase chromatography. The product fractions were combined, concentrated to remove most of the acetonitrile, diluted with ethyl acetate and 10% aqueous potassium carbonate, extracted, dried with magnesium sulfate, filtered, concentrated, and briefly vacuum dried to give 0.439 gm of product. GCMS (M) 317; $^1$H NMR (400 MHz, DMSO-$d_6$) δ ppm 8.36 (d, J=2.15 Hz, 1H) 8.52 (d, J=2.15 Hz, 1H).

Step 2: Preparation of 5-bromo-3-chloro-2-(1-methyl-1H-pyrazol-5-yl)pyridine 102.7 mg of 5-bromo-2,3-dichloropyridine, 52.8 mg of 1-methylpyrazole-5-boronic acid, and 24.9 mg of 1,1'-bis(diphenylphosphino)ferrocene palladium dichloride dichloromethane adduct were placed in a septum sealed vial and evacuated/nitrogen filled three times. 2.00 mL of anhydrous dioxane and 0.630 of nitrogen saturated aqueous 2M cesium carbonate were added, and the mixture was heated at 80° C. for 20 minutes. The reaction was cooled, and 43.2 mg more of 1-methylpyrazole-5-boronic acid was added before heating another 15 minutes. The reaction was cooled, diluted into ethyl acetate, extracted with water, dried with magnesium sulfate, filtered, and flash chromatographed to give 50.2 mg of product. LCMS (M+H) 27; $^1$H NMR (400 MHz, DMSO-$d_6$) δ ppm 3.79-3.88 (m, 3H) 6.68 (d, J=1.88 Hz, 1H) 7.54 (d, J=1.88 Hz, 1H) 8.53 (d, J=1.88 Hz, 1H) 8.83 (d, J=2.15 Hz, 1H).

Step 3: Preparation of 4-(3-{[5-chloro-6-(1-methyl-1H-pyrazol-5-yl)pyridin-3-yl]thio}phenyl)tetrahydro-2H-pyran-4-carboxamide 90.6 mg of 4-{3-[(triisopropylsilyl)thio]phenyl}tetrahydro-2H-pyran-4-carboxamide, 48.4 mg of 5-bromo-3-chloro-2-(1-methyl-1H-pyrazol-5-yl)pyridine, 14.0 mg of tetrakis(triphenylphosphine)palladium, 6.7 mg of bis[(2-diphenylphosphino)phenyl]ether, 35.4 mg of cesium fluoride, and 34.5 mg of tetraethylammonium chloride monohydrate were placed in a septum sealed vial and evacuated/nitrogen filled three times. 2 mL of anhydrous isopropanol were added, followed by the addition of 0.180 mL of 1.0 M potassium t-butoxide in tetraydrofuran. The mixture was stirred at room temperature for 5 minutes and then heated at 80° C. for 30 minutes. The reaction mixture was cooled, diluted into ethyl acetate, extracted with 5% aqueous potassium carbonate, dried with magnesium sulfate, filtered, concentrated, and purified by reverse phase chromatography. The product fractions were diluted into ethyl acetate, extracted with 5% aqueous sodium bicarbonate, dried with magnesium sulfate, filtered, concentrated, and vacuum dried to give 66.5 mg of product. HRMS (M+H) calc. 429.1152, found 429.1132; $^1$H NMR (400 MHz, DMSO-$d_6$) δ ppm 1.76-1.88 (m, 2H) 2.42 (d, J=13.96 Hz, 2H) 3.43-3.51 (m, 2H) 3.68-3.77 (m, 2H) 3.83 (s, 3H) 6.65 (d, J=1.88 Hz, 1H) 7.08 (s, 1H) 7.28 (s, 1H) 7.40-7.50 (m, 3H) 7.53 (d, J=2.15 Hz, 1H) 7.57 (s, 1H) 7.87 (d, J=2.15 Hz, 1H) 8.46 (d, J=2.15 Hz, 1H).

Example 12

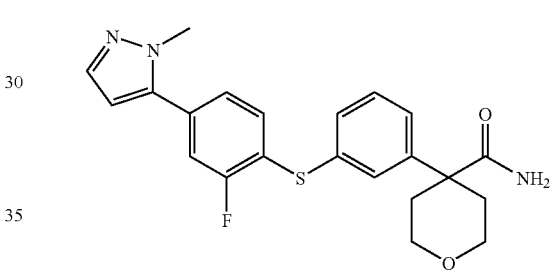

4-(3-{[2-Fluoro-4-(1-methyl-1H-pyrazol-5-yl)phenyl]thio}phenyl)tetrahydro-2H-pyran-4-carboxamide Step 1: Preparation of 4-{3-[(4-acetyl-2-fluorophenyl)thio]phenyl}tetrahydro-2H-pyran-4-carboxamide 3,4-Difluoroacetophenone (0.234 g, 1.50 mmol), 4-{3-[(triisopropylsilyl)thio]phenyl}tetrahydro-2H-pyran-4-carboxamide (0.590 g, 1.50 mmol), tetrabutylammonium fluoride (0.66 g, 2.54 mmol) and potassium tert-butoxide (1.0 M in THF, 2.0 mL, 2.0 mmol) were added to anhydrous toluene (10 mL). The mixture was warmed to 90 degrees Celsius and stirred for 4 hours. After cooling to room temperature, ethyl acetate was added (100 mL) along with 1.0 N HCl (6 mL). The mixture was then stirred for 30 minutes and the beige precipitated was collected by suction filtration. The crude product was purified further on silica gel using a 70:30 mixture of methylene chloride and acetone, respectively. The product was a light brown solid and weighed 0.36 g (64%). LC/MS: 5%-100% CH3CN:H20 gradient over 4.5 minutes: 3.1 minutes, 374.2 (M+H).

Step 2: Preparation of 4-[3-({4-[(2E)-3-(dimethylamino)prop-2-enoyl]-2-fluorophenyl}thio)phenyl]tetrahydro-2H-pyran-4-carboxamide 4-{3-[(4-Acetyl-3-fluorophenyl)thio]phenyl}tetrahydro-2H-pyran-4-carboxamide (600 mg, 1.60 mmol) was added to anhydrous DMF (5 mL). Then, the dimethyl acetal of DMF was added (1.03 g, 8.7 mmol), and the solution was heated at 100 degrees Celsius for four hours. The volatiles were evaporated at reduced pressure to provide an orange residual solid that was used, without additional purification, for the next step.

Step 3: Preparation of 4-(3-{[2-fluoro-4-(1-methyl-1H-pyrazol-5-yl)phenyl]thio}phenyl)tetrahydro-2H-pyran-4-carboxamide 4-[3-({4-[(2E)-3-(Dimethylamino)prop-2-enoyl]-2-fluorophenyl}thio)phenyl]tetrahydro-2H-pyran-4-carboxamide (52 mg, 0.121 mmol) was dissolved in anhydrous DMF (5 mL). This solution was cooled to 0 degrees Celsius and methyl hydrazine (2 mL) was added. The solution was stirred at 0 degrees Celsius for one hour and then at room temperature for 10 hours. The volatiles were removed by rotary evaporation. The viscous oily residue was dissolved in a small volume of methylene chloride and applied to a cartridge of silica gel. The cartridge was eluted using a gradient going from a 7:3 ratio of methylene chloride and acetone, respectively, to a 2:8 ratio of methylene chloride and acetone, respectively. Fractions containing the product were combined and concentrated to provide the product as a white solid (15 mg, 30%). 1H NMR (400 MHz, DMSO-$d_6$) δ ppm 1.80 (t, J=10.06 Hz, 2H) 2.40 (d, J=12.44 Hz, 2H) 3.42-3.52 (m, 2H) 3.72 (d, J=11.71 Hz, 2H) 3.88 (s, 3H) 6.49 (s, 1H) 7.02 (br. s., 1H) 7.20-7.29 (m, 2H) 7.34-7.43 (m, 4H) 7.46 (d, J=9.52 Hz, 2H) 7.54 (d, J=10.98 Hz, 1H); HRMS calc M+H: 412.1495, found 412.1454.

Example 13

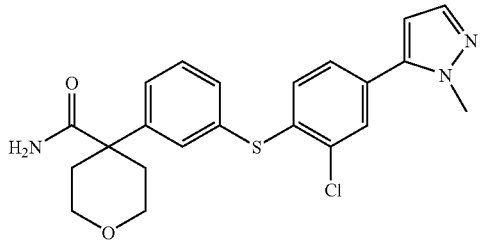

4-(3-{[2-chloro-4-(1-methyl-1H-pyrazol-5-yl)phenyl]thio}phenyl)tetrahydro-2H-pyran-4-carboxamide Step 1: Preparation of 4-{3-[(4-bromo-2-chlorophenyl)thio]phenyl}tetrahydro-2H-pyran-4-carboxamide 1.15 g of 4-{3-[(triisopropylsilyl)thio]phenyl}tetrahydro-2H-pyran-4-carboxamide, 1.016 g of 4-bromo-2-chloroiodobenzene, 0.206 g of tetrakis(triphenylphosphine)palladium, 0.0916 g of bis[(2-diphenylphosphino)phenyl]ether, 0.525 g of cesium fluoride, and 0.631 g of tetraethylammonium chloride monohydrate were placed in a flask and evacuated/nitrogen filled three times. 22 mL of anhydrous isopropanol was added, followed by the addition of 3.50 mL of 1.0 M potassium t-butoxide in tetrahydrofuran. The reaction mixture was heated at reflux for 30 minutes, cooled, concentrated, and flash chromatographed on silica gel to give 0.98 g of product. HRMS (M+H) calc. 425.9930, found 425.9923; 1H NMR (400 MHz, DMSO-$d_6$) δ ppm 1.79 (ddd, J=13.96, 10.47, 4.03 Hz, 2H) 2.41 (d, J=13.70 Hz, 2H) 3.46 (t, J=10.88 Hz, 2H) 3.68-3.77 (m, 2H) 6.82 (d, J=8.59 Hz, 1H) 7.08 (br. s., 1H) 7.28 (br. s., 1H) 7.30-7.34 (m, 1H) 7.43-7.51 (m, 4H) 7.83 (d, J=2.15 Hz, 1H).

Step 2: Preparation of 4-(3-{[2-chloro-4-(1-methyl-1H-pyrazol-5-yl)phenyl]thio}phenyl)tetrahydro-2H-pyran-4-carboxamide 117.5 mg of 4-{3-[(4-bromo-2-chlorophenyl)thio]phenyl}tetrahydro-2H-pyran-4-carboxamide, 130.1 g of (1-methyl-1H-pyrazol-5-yl)boronic acid, and 38.1 mg of 1,1'-bis(diphenylphosphino)ferrocene palladium dichloride dichloromethane adduct were placed in a vial and evacuated/nitrogen filled three times. 2 mL of anhydrous dioxane and 0.55 mL of 2 M aqueous cesium carbonate were added, and the mixture was heated at 70° C. for 30 minutes, cooled, diluted the dioxane phase into ethyl acetate, dried with magnesium sulfate, filtered, concentrated, and purified by reverse phase chromatography to give 71.9 mg of product. HRMS (M+H) calc. 428.1199, found 428.1133; 1H NMR (400 MHz, DMSO-$d_6$) δ ppm 1.82 (ddd, J=13.70, 10.47, 3.76 Hz, 2H) 2.43 (d, J=13.96 Hz, 2H) 3.47 (t, J=10.20 Hz, 2H) 3.73 (dt, J=11.75, 3.52 Hz, 2H) 3.85 (s, 3H) 6.46 (d, J=1.88 Hz, 1H) 6.92 (d, J=8.32 Hz, 1H) 7.09 (br. s., 1H) 7.30 (br. s., 1H) 7.37-7.48 (m, 3H) 7.50 (d, J=5.10 Hz, 2H) 7.55 (s, 1H) 7.72 (d, J=1.88 Hz, 1H).

Example 14

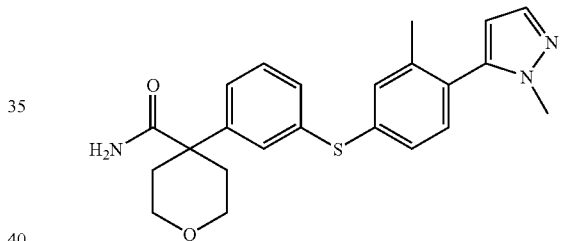

4-(3-{[3-methyl-4-(1-methyl-1H-pyrazol-5-yl)phenyl]thio}phenyl)tetrahydro-2H-pyran-4-carboxamide Step 1: Preparation of 5-(4-bromo-2-methylhenyl)-1-methyl-1H-pyrazole 0.1 g of 1-bromo-4-iodo-5-methylbenzene, 0.043 g of 1-methyl-1H-pyrazol-5-ylboronic acid, and 0.045 g of 1,1'-Bis(diphenylphosphino)ferrocene]-dichloropalladium(II) were placed in a septum-sealed vial and evacuated/nitrogen filled three times. 3 mL of 1,4-dioxane was then added, followed by the addition of 0.5 mL of 1 M cesium carbonate. The mixture was stirred at room temperature for 30 minutes and heated at 70° C. for 4 hours. The reaction mixture was cooled, diluted with water, and extracted with ethyl acetate. The ethyl acetate was dried with sodium sulfate, filtered, concentrated, and the residue was purified by reverse phase HPLC to give 0.05 g of product. LCMS (M+H): 252.

Step 2: Preparation of 4-(3-{[3-methyl-4-(1-methyl-1H-Pyrazol-5-yl)phenyl]thio}-phenyl)tetrahydro-2H-pyran-4-carboxamide 0.157 g of 4-{3-[(triisopropylsilyl)thio]phenyl}tetrahydro-2H-pyran-4-carboxamide, 0.068 g of tetraethylammonium chloride, 0.01 g of oxydi-2,1-phenylene bis-(diphenylphosphine), 0.024 g palladium(0)tetrakis-(triphenylphosphine), 0.1 g of 5-(4-bromo-2-methylphenyl)-1-methyl-1H-pyrazole, and 0.065 g of cesium fluoride were placed in a reaction flask and evacuated and filled with nitrogen 3 times. 5 mL of nitrogen-purged isopropanol was added, followed by the addition of 0.6 mL of 1.0 M potassium t-butoxide in tetrahydrofuran. The mixture was then refluxed for 2 hours. After cooling, the reaction mixture was diluted with water and extracted with ethyl acetate. The ethyl acetate extract was dried with sodium sulfate, filtered, concentrated, and purified by reverse phase chromatography to give 0.082 g of product. HRMS (M+H) calc. 408.1746, found 408.1743; 1H NMR (400 MHz, DMSO-$d_6$) δ ppm 1.74 (s, 3H) 2.09 (s, 2H) 3.17 (s, 3H) 3.38 (s, 2H) 3.47 (s, 2H) 3.59 (s, 2H) 3.70 (s, 2H) 6.26 (s, 1H) 7.02 (s, 1H) 7.22 (s, 1H) 7.26 (d, J=15.74 Hz, 2H) 7.37-7.48 (m, 3H) 7.62 (s, 1H).

Example 15

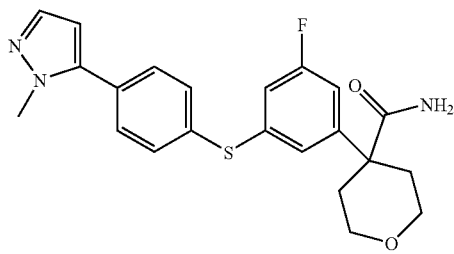

4-(3-fluoro-5-{[4-(1-methyl-1H-pyrazol-5-yl)phenyl]thio}phenyl)tetrahydro-2H-pyran-4-carboxamide Step 1: Preparation of 4-(3,5-difluorophenyl)tetrahydro-2H-pyran-4-carboxamide 4-(3,5-difluorophenyl)tetrahydro-2H-pyran-4-carbonitrile (prepared according to the procedures in Synthesis (2004), 16, 2625-2628), (10 g) was slowly combined with 100 mL of ice cold sulfuric acid. The resulting mixture was heated at 145° C. for 2 hours. After cooling to room temperature, the mixture was poured over ice, and the pH was adjusted to 10 with 5 N NaOH. The solid was isolated by filtration, rinsing with water and hexanes to give 2.2 g of the product. LC/MS (M+H): 242; 1H NMR (400 MHz, DMSO-$d_6$) δ ppm 1.79 (ddd, J=13.83, 10.61, 3.76 Hz, 2H) 2.39 (d, J=13.16 Hz, 2H) 3.41-3.50 (m, 2H) 3.73 (dt, J=11.61, 3.73 Hz, 2H) 7.02-7.18 (m, 4H) 7.29 (s, 1H).

Step 2: Preparation of 1-methyl-5-{4-[(triisopropylsilyl)thio]phenyl}-1H-pyrazole 5-(4-bromophenyl)-1-methyl-1H-pyrazole (7.84 g), sodium tert-butoxide (3.81 g), 1,1'-bus(di-1-propylphosphino)ferrocene (332 mg), and palladium acetate (148 mg) were placed under nitrogen and combined with 60 mL anhydrous 1,4-dioxane. The resulting mixture was stirred at room temperature for 1 hour before adding triisopropylsilanethiol (7.81 ml) followed by heating at reflux for 1 hour. After cooling to room temperature, the mixture was diluted with ethyl acetate and washed with water twice and 5% aqueous sodium chloride once. The organic layer was dried over sodium sulfate, filtered, concentrated, and purified by flash chromatography on silica gel to give the title compound. LCMS (M+H): 347; 1H NMR (400 MHz, DMSO-d6) δ ppm 0.85-0.96 (m, 3H) 0.96-1.02 (m, 18H) 3.84 (s, 3H) 7.40 (s, 1H) 7.46 (s, 1H) 7.58 (d, J=8.32 Hz, 2H) 7.63-7.71 (m, 2H).

Step 3: Preparation of 4-(3-fluoro-5-{[4-(1-methyl-1H-pyrazol-5-yl)phenyl]thio}phenyl)tetrahydro-2H-pyran-4-carboxamide 1-methyl-5-{4-[(triisopropylsilyl)thio]phenyl}-1H-pyrazole (100 mg) was placed under nitrogen and dissolved with 1.5 mL anhydrous 1-methyl-2-pyrrolidinone. Water (5.2 uL) was added, and the solution was stirred for 40 minutes. 1.0 M potassium tert-butoxide in tetrahydrofuran (0.29 mL) was added, and the solution was stirred for 15 minutes. In a separate vial, 4-(3,5-difluorophenyl) tetrahydro-2H-pyran-4-carboxamide (70 mg) was dissolved in 1 mL anhydrous 1-methyl-2-pyrrolidinone and added to the main reaction mixture. The resulting solution was heated at 135° C. for 40 hours and then purified by reverse phase chromatography to give the product (27 mg). HRMS (M+H) calc. 412.1495, found 412.1550; 1H NMR (400 MHz, DMSO-$d_6$) δ ppm 1.72-1.83 (m, 2H) 2.37 (d, J=12.89 Hz, 2H) 3.39-3.49 (m, 2H) 3.72 (dt, J=11.55, 3.63 Hz, 2H) 3.87 (s, 3H) 6.45 (d, J=1.88 Hz, 1H) 7.03 (dt, J=8.86, 1.88 Hz, 1H) 7.11-7.17 (m, 2H) 7.23 (t, J=1.61 Hz, 1H) 7.31 (s, 1H) 7.44-7.49 (m, J=8.59, 2.01, 2.01 Hz, 3H) 7.58 (ddd, J=8.46, 2.15, 2.01 Hz, 2H).

Example 16

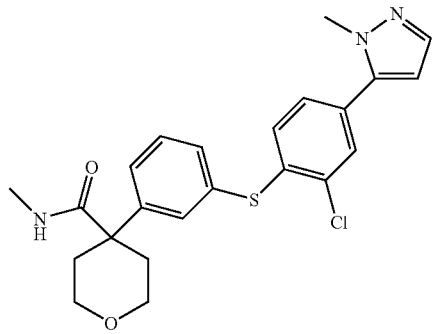

4-(3-{[2-chloro-4-(1-methyl-1H-pyrazol-6-yl)phenyl]thio}phenyl)-N-methyltetrahydro-2H-pyran-4-carboxamide 80 mg of the compound of example 13 and 10 mL of anhydrous tetrahydrofuran were placed in an oven-dried vial. 30 mg of sodium hydride (60% dispersion in mineral oil) was added, and the mixture was stirred at room temperature for 30 minutes. 0.035 mL of methyl iodide was added, and the mixture was stirred at room temperature for 2 hours. 0.042 mL of glacial acetic acid was added, and the reaction was diluted with ethyl acetate and extracted with water and 5% sodium chloride, dried over magnesium sulfate, filtered, concentrated, and purified by reverse phase chromatography. The product fractions were diluted into ethyl acetate, extracted with 5% aqueous sodium bicarbonate, dried with magnesium sulfate, filtered, concentrated, and vacuum dried to give 41 mg of product. HRMS (M+H) calc. 442.1356, found 442.1472; 1H NMR (400 MHz, DMSO-d6) δ ppm 1.80-1.90 (m, 2H) 2.40 (d, J=13.70 Hz, 2H) 2.54 (d, J=4.30 Hz, 3H) 3.43

(t, J=10.20 Hz, 2H) 3.71 (dt, J=11.88, 3.73 Hz, 2H) 3.85 (s, 3H) 6.46 (d, J=2.15 Hz, 1H) 6.93 (d, J=8.32 Hz, 1H) 7.38 (ddd, J=7.12, 1.75, 1.61 Hz, 1H) 7.43 (dd, J=8.32, 1.88 Hz, 1H) 7.45-7.52 (m, 4H) 7.68 (q, J=4.39 Hz, 1H) 7.72 (d, J=1.88 Hz, 1H).

Example 17

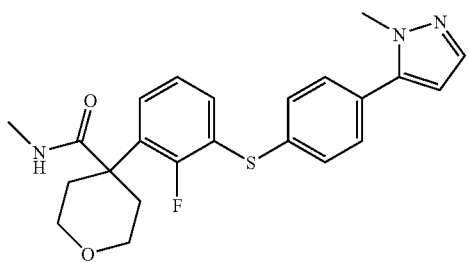

4-(2-fluoro-3-{[4-(1-methyl-1H-pyrazol-5-yl)phe-nyl]thio}phenyl)-N-methyl-tetrahydro-2H-pyran-4-carboxamide Step 1: Preparation of (3-bromo-2-fluorophenyl)methanol 5.0 g of 3-bromo-2-fluorobenzoic acid and 40 mL of anhydrous tetrahydrofuran were placed under nitrogen in an oven-dried flask and chilled to 0° C. 34.2 mL of 1 M boran-tetrahydrofuran complex was added from an addition funnel, and the mixture was stirred at room temperature overnight. 5 mL of water were added, and the reaction was concentrated, diluted with diethyl ether, and extracted with saturated potassium carbonate, water, and 5% sodium chloride before drying over sodium sulfate. The solution was filtered, concentrated, and purified by flash chromatography on silica. The product fractions were concentrated and vacuum dried to give 4.26 g. GCMS (M) 204; 1H NMR (400 MHz, DMSO-d6) δ ppm 4.57 (d, J=5.91 Hz, 2H) 5.39 (t, J=5.77 Hz, 1H) 7.15 (t, J=8.06 Hz, 1H) 7.44-7.50 (m, 1H) 7.55-7.61 (m, 1H).

Step 2: Preparation of 1-bromo-3-(chloromethyl)-2-fluorobenzene 4.26 g of (3-bromo-2-fluorophenyl)methanol and 70 mL of anhydrous methylene chloride were placed under nitrogen in an oven-dried flask. 1.64 mL thionyl chloride was added, and the mixture was stirred at room temperature overnight, concentrated, and diluted with diethyl ether. 50 mL of saturated potassium carbonate were added, and the phases were allowed to separate. The organic layer was extracted two times with water and one time with 5% sodium chloride, dried over magnesium sulfate, filtered, concentrated, and purified by flash chromatography on silica. The product fractions were concentrated and vacuum dried to give 2.72 g of product. 1H NMR (400 MHz, DMSO-d6) δ ppm 5.11 (ddd, J=16.45, 12.15, 0.94 Hz, 2H) 7.16-7.22 (m, 1H) 7.44-7.50 (m, 1H) 7.73 (ddd, J=8.19, 6.85, 1.61 Hz, 1H).

Step 3: Preparation of (3-bromo-2-fluorophenyl)acetonitrile 2.7 g of 1-bromo-3-(chloromethyl)-2-fluorobenzene, 0.83 g of potassium cyanide, and 25 mL of anhydrous dimethyl-sulfoxide were place under nitrogen in an oven-dried flask and stirred at room temperature for 2 hours. The reaction was diluted into ethyl acetate and extracted four times with 5% sodium chloride, dried over magnesium sulfate, filtered, concentrated, and purified by flash chromatography on silica. The product fractions were concentrated and vacuum dried to give 1.17 g of product. GCMS (M) 213; 1H NMR (400 MHz, DMSO-d6) δ ppm 4.14 (s, 2H) 7.21 (td, J=7.85, 0.94 Hz, 1H) 7.45-7.51 (m, J=7.32, 7.32, 0.94, 0.81 Hz, 1H) 7.71 (ddd, J=8.12, 6.65, 1.61 Hz, 1H).

Step 4: Preparation of 4-(3-bromo-2-fluorophenyl) tetrahydro-2H-pyran-4-carbonitrile 1.17 g of (3-bromo-2-fluorophenyl)acetonitrile and 15 mL of anhydrous DMSO were placed under nitrogen in an oven-dried flask. 459 mg of sodium hydride (60% dispersion in oil) were added, and the mixture was stirred at room temperature for 1 hour. 0.86 g of 2-chloroethyl ether dissolved with 2 ml anhydrous DMSO was added, and the mixture was stirred at room temperature overnight. 0.65 mL of glacial acetic acid was added, and the reaction was diluted into ethyl acetate, extracted with water and 5% sodium chloride, dried over magnesium sulfate, filtered, concentrated, and purified by flash chromatography on silica. The product fractions were concentrated and vacuum dried to give 730 mg of product. GCMS (M) 283; 1H NMR (400 MHz, DMSO-d6) δ ppm 2.04-2.15 (m, 2H) 2.17-2.25 (m, 2H) 3.69 (td, J=12.08, 1.88 Hz, 2H) 4.01 (dd, J=11.95, 2.82 Hz, 2H) 7.27 (td, J=7.92, 1.07 Hz, 1H) 7.47-7.55 (m, 1H) 7.80 (ddd, J=8.12, 6.65, 1.61 Hz, 1H).

Step 5: Preparation of 4-(3-bromo-2-fluorophenyl) tetrahydro-2H-pyran-4-carboxamide 705 mg of 4-(3-bromo-2-fluorophenyl)tetrahydro-2H-pyran-4-carbonitrile, and 418 mg ground potassium hydroxide were place in an oven-dried vial and evacuated/nitrogen filled three times. 8 mL tertiary butyl alcohol was added, and the mixture was heated at 80° C. for two hours. The reaction was cooled, diluted with ethyl acetate, extracted two times with water and one time with 5% sodium chloride, dried over magnesium sulfate, filtered, concentrated, and purified by reverse phase chromatography. The product fractions were diluted into ethyl acetate, extracted with 5% aqueous sodium bicarbonate, dried with magnesium sulfate, filtered, concentrated, and vacuum dried to give 593 mg of product. LCMS (M+H) 302. 1H NMR (400 MHz, DMSO-d6) δ ppm 1.93 (ddd, J=13.56, 7.79, 5.77 Hz, 2H) 2.32 (d, J=13.70 Hz, 2H) 3.59-3.70 (m, 4H) 7.01 (br. s., 1H) 7.07 (br. s., 1H) 7.17 (td, J=7.92, 0.81 Hz, 1H) 7.45 (td, J=7.65, 1.61 Hz, 1H) 7.62 (ddd, J=8.06, 6.44, 1.61 Hz, 1H).

Step 6: Preparation of 4-(1-methyl-1H-pyrazol-5-yl)benzenethiol

Inside an argon filled glove bag, 3.41 g of sodium t-butoxide was placed in an oven-dried flask. 7.03 g of 5-(4-bromophenyl)-1-methyl-1H-pyrazole, 0.328 g of palladium acetate, and 0.7720 g of 1,1'-bis(di-1-propylphosphino)-ferrocene were added, and the mixture was evacuated/nitrogen filled three times. 50 mL of anhydrous 1,4-dioxane was added, followed by the addition of 7.00 mL of triisopropyl-silanethiol. After heating at reflux for 40 minutes, the reaction mixture was cooled, and 20 mL of 2.5 N aqueous sodium hydroxide and 15 mL of DMSO were then added under nitrogen. The reaction was stirred vigorously at room temperature for 40 minutes and then diluted into ether. The addition of 125 mL of 5% aqueous sodium chloride containing ~5 mL of concentrated hydrochloric acid adjusted the pH of the aqueous phase to 4, and the mixture was extracted, separated, extracted the aqueous again with ether, combined the ether extracts, dried with magnesium sulfate, filtered, and concentrated to give a dark liquid. The crude product was diluted into ether, extracted twice with 100-mL portions of 0.5 N aqueous sodium hydroxide (discarded the ether), combined the aqueous extracts, extracted the aqueous solution with ether (discarded ether), carefully adjusted the pH to 3 with concentrated hydrochloric acid, extracted three times with ether, combined the ether extracts, dried with magnesium sulfate, filtered, concentrated, and flash chromatographed on silica gel to give 4.4600 gm of product. 1H NMR (400 MHz, DMSO-$d_6$) δ ppm 3.83 (s, 3H) 5.65 (s, 1H) 6.36 (d, J=1.95 Hz, 1H) 7.40 (s, 4H) 7.44 (d, J=1.95 Hz, 1H).

Step 7: Preparation of 4-(2-fluoro-3-{[4-(1-methyl-1H-pyrazol-5-yl)phenyl]thio}-phenyl)tetrahydro-2H-pyran-4-carboxamide 277 mg of 4-(1-methyl-1H-pyrazol-5-yl)benzenethiol, 400 mg of 4-(3-bromo-2-fluorophenyl)tetrahydro-2H-pyran-4-carboxamide, 35.1 mg of bis[(2-diphenylphosphino)phenyl]ether, 77.9 mg of tetrakis(triphenylphosphin)palladium (0) were placed in an oven-dried vial and evacuated/nitrogen filled three times. 15 mL of anhydrous 1,4-dioxane and 3.97 mL of 2 M cesium carbonate was added, and the mixture was heated at 80° C. overnight. The mixture was cooled, concentrated, and purified by reverse phase chromatography. The product fractions were diluted into ethyl acetate, extracted with 5% aqueous sodium bicarbonate, dried with magnesium sulfate, filtered, and concentrated. The residue was triturated with diethyl ether, filtered, and vacuum dried to give 223 mg of product. HRMS (M+H) calc. 412.1495, found 412.1593; 1H NMR (400 MHz, DMSO-d6) δ ppm 1.89-2.00 (m, 2H) 2.32 (d, J=13.43 Hz, 2H) 3.63-3.69 (m, 4H) 3.85 (s, 3H) 6.42 (d, J=1.88 Hz, 1H) 7.01 (br. s., 1H) 7.06 (br. s., 1H) 7.23-7.36 (m, 4H) 7.46 (d, J=1.88 Hz, 1H) 7.47-7.55 (m, 3H).

Step 8: Preparation of 4-(2-fluoro-3-{[4-(1-methyl-1H-pyrazol-5-yl)phenyl]thio}-phenyl)-N-methyltetrahydro-2H-pyran-4-carboxamide 198 mg of 4-(2-fluoro-3-{[4-(1-methyl-1H-pyrazol-5-yl)phenyl]thio}phenyl)-tetrahydro-2H-pyran-4-carboxamide and 20 ml anhydrous tetrahydrofuran were placed under nitrogen in an oven-dried vial. 39 mg of sodium hydride (60% dispersion in mineral oil) were added, and the mixture was stirred at room temperature for 30 minutes. 0.050 mL of methyl iodide was added, and the mixture was stirred at room temperature for 3 hours. 0.055 mL of glacial acetic acid was added, and the reaction was diluted with ethyl acetate, extracted with water and 5% sodium chloride, dried with magnesium sulfate, filtered, concentrated, and purified by reverse phase chromatography. The product fractions were diluted into ethyl acetate, extracted with 5% aqueous sodium bicarbonate, dried with magnesium sulfate, filtered, and vacuum dried to give 108 mg of product. HRMS (M+H) calc. 426.1651, found 426.1750; 1H NMR (400 MHz, DMSO-d6) δ ppm 1.96 (ddd, J=13.63, 8.12, 5.37 Hz, 2H) 2.30 (d, J=13.43 Hz, 2H) 2.54 (d, J=4.57 Hz, 3H) 3.58-3.70 (m, 4H) 3.84 (s, 3H) 6.41 (d, J=1.88 Hz, 1H) 7.24-7.37 (m, 4H) 7.41 (q, J=4.48 Hz, 1H) 7.46 (d, J=1.88 Hz, 1H) 7.47-7.54 (m, 3H).

Example 18

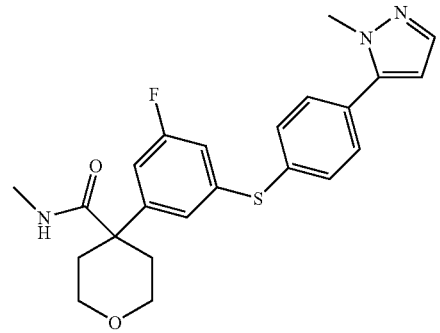

4-(3-fluoro-5-{[4-(1-methyl-1H-pyrazol-5-yl)phenyl]thio}-phenyl)-N-methyltetrahydro-2H-pyran-4-carboxamide The title compound was made using the method described in example 16 using the compound of example 15 as starting material.

HRMS (M+H) calc. 426.1651, found 426.1796; 1H NMR (400 MHz, DMSO-d6) δ ppm 1.81 (ddd, J=13.90, 10.41, 3.89 Hz, 2H) 2.35 (d, J=13.70 Hz, 2H) 2.54 (d, j=4.57 Hz, 3H) 3.36-3.46 (m, 2H) 3.70 (ddd, J=11.55, 3.76, 3.49 Hz, 2H) 3.87 (s, 3H) 6.45 (d, J=1.88 Hz, 1H) 7.03 (ddd, J=8.39, 2.28, 1.95 Hz, 1H) 7.11 (dt, J=10.54, 1.98 Hz, 1H) 7.14 (t, J=1.48 Hz, 1H) 7.46 (dt, J=8.86, 2.15 Hz, 3H) 7.58 (ddd, J=8.46, 2.15, 2.01 Hz, 2H) 7.69 (q, J=4.21 Hz, 1H).

Example 19

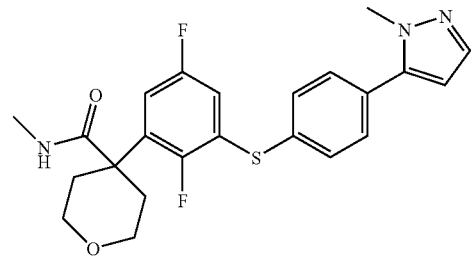

4-(2,5-difluoro-3-{[4-(1-methyl-1H-pyrazol-5-yl)phenyl]thio}phenyl)-N-methyltetrahydro-2H-pyran-4-carboxamide Step 1: Preparation of 4-amino-2,5-difluorobenzonitrile 10 g of 4-bromo-2,5-difluoroaniline, 4.48 g of copper (I) cyanide, and 110 mL of anhydrous dimethyl formamide were placed under nitrogen in an oven-dried flask and heated at reflux overnight. The reaction was cooled, and 110 mL of 10% aqueous sodium cyanide was added and stirred for 30 minutes. The reaction was diluted with 200 mL water and extracted three times with methylene chloride. The combined organic layers were extracted with 5% sodium carbonate and water, dried over sodium sulfate, filtered, concentrated, and purified by flash chromatography on silica. The product fractions were concentrated and vacuum dried to give 5 g of product. GCMS (M) 154; 1H NMR (400 MHz, DMSO-d6) δ ppm 6.58-6.68 (m, 3H) 7.57 (dd, J=11.14, 6.04 Hz, 1H).

Step 2: Preparation of 4-amino-3-bromo-2,5-difluorobenzonitrile 5.0 g of 4-amino-2,5-difluorobenzonitrile, 5.13 g bromine, 2 mL water, and 50 mL glacial acetic acid were placed under nitrogen in an oven-dried flask and stirred overnight at room temperature. The reaction was concentrated, diluted with methylene chloride, extracted with water and 5% sodium carbonate, dried over sodium sulfate, filtered, concentrated, and purified by flash chromatography on silica. The product fractions were concentrated and vacuum dried to give 6.9 g of product. GCMS (M) 232; 1H NMR (400 MHz, DMSO-d6) δ ppm 6.89 (s, 2H) 7.71 (dd, J=11.14, 6.04 Hz, 1H).

Step 3: Preparation of 4-amino-3-bromo-2,5-difluorobenzaldehyde 6.70 g of 4-amino-3-bromo-2,5-difluorobenzonitrile and 0.754 g of platinum (IV) oxide were placed in a Fischer-Porter pressure bottle and evacuated/nitrogen filled three times. Under a nitrogen atmosphere, 36 mL of formic acid and 9 mL of nitrogen-saturated water were added, and the mixture was heated at 60° C. for 4 hours. The reaction was cooled, filtered over a Celite bed, concentrated, diluted with ethyl acetate, extracted with saturated sodium carbonate, dried over sodium sulfate, filtered, concentrated, and purified by flash chromatography on silica. The product fractions were concentrated and vacuum dried to give 4.61 g of product. GCMS (M) 235; 1H NMR (400 MHz, DMSO-d6) δ ppm 6.94 (br. s., 2H) 7.44 (dd, J=11.01, 6.18 Hz, 1H) 9.90 (d, J=2.95 Hz, 1H).

Step 4: Preparation of 3-bromo-2,5-difluorobenzaldehyde 4.6 g of 4-amino-3-bromo-2,5-difluorobenzaldehyde, 110 mL glacial acetic acid, and 54 mL of hypophosphorous acid were placed under nitrogen in an oven-dried flask and chilled to 0° C. 1.96 g of sodium nitrite dissolved with 11 mL water was added to the reaction mixture from an addition funnel maintaining reaction temperature below 15° C. The mixture was warmed to room temperature and stirred for 1 hour, diluted into 300 mL of ice water and extracted 3 times with methylene chloride. The combined organic layers were extracted with water, 2 times with 10% sodium hydroxide, 2 times with water, dried over sodium sulfate, filtered, concentrated, and purified by flash chromatography on silica. The product fractions were concentrated and dried under vacuum to give 2.79 g of product. GCMS (M) 222; 1H NMR (400 MHz, DMSO-d6) δ ppm 7.66 (ddd, J=8.06, 4.83, 3.22 Hz, 1H) 8.12 (ddd, J=7.52, 5.37, 3.22 Hz, 1H) 10.13 (d, J=2.42 Hz, 1H).

Step 5: Preparation of (3-bromo-2,5-difluorophenyl)methanol 2.69 g of 3-bromo-2,5-difluorobenzaldehyde, and 30 mL of anhydrous tetrahydrofuran were placed in an oven-dried flask and chilled to 0° C. 18.3 mL of boran-tetrahydrofuran complex was added slowly from an addition funnel, and the mixture was warmed to room temperature and stirred for 3 hours. 5 mL of water were added, and the reaction was concentrated, diluted with diethyl ether, and extracted with saturated potassium carbonate. The aqueous layer was extracted 3 times with diethyl ether, and the combined organic layers were extracted with water and 5% sodium chloride, dried over magnesium sulfate, filtered, and concentrated. Crystals formed upon sitting overnight and were dried under vacuum to give 2.7 g of product. GCMS (M) 222.; 1H NMR (400 MHz, DMSO-d6) δ ppm 4.57 (d, J=5.91 Hz, 2H) 5.53 (t, J=5.91 Hz, 1H) 7.29 (ddd, J=8.73, 5.24, 3.22 Hz, 1H) 7.58 (ddd, J=7.99, 5.17, 3.22 Hz, 1H).

Step 6: Preparation of 1-bromo-3-(chloromethyl)-2,5-difluorobenzene 590 mg of (3-bromo-2,5-difluorophenyl)methanol, and 5 ml anhydrous methylene chloride were placed under nitrogen in an oven dried vial and chilled to 0° C. 0.42 ml thionyl chloride was added and the mixture was warmed to room temperature and stirred for 2 hours. The reaction was concentrated, diluted with diethyl ether and 5 ml saturated potassium carbonate and additional water was added. The two phases were separated and the aqueous layer was extracted with diethyl ether. The organic layers were combined and extracted with water, 5% sodium chloride, dried with magnesium sulfate, filtered, concentrated, and purified by flash chromatography on silica. The product fractions were concentrated and vacuum dried to give 275 mg of product. GCMS (M-Cl) 220.

Step 7: Preparation of (3-bromo-2,5-difluorophenyl)acetonitrile 775 mg of 1-bromo-3-(chloromethyl)-2,5-difluorobenzene, 251 mg of potassium cyanide, and 7 ml anhydrous dimethyl sulfoxide were placed under nitrogen in an oven dried vial and stirred at room temperature for 1 hour. The reaction mixture was diluted with ethyl acetate and extracted four times with 5% sodium chloride, dried over magnesium sulfate, filtered, concentrated and purified by flash chromatography on silica. The product fractions were concentrated and vacuum dried to give 277 mg of product. GCMS (M) 231; 1H NMR (400 MHz, DMSO-d6) δ ppm 4.13-4.17 (m, 2H) 7.40 (ddd, J=8.59, 5.37, 3.22 Hz, 1H) 7.76 (ddd, J=8.06, 5.10, 2.95 Hz, 1H).

Step 8: Preparation of 4-(3-bromo-2,5-difluorophenyl)tetrahydro-2H-pyran-4-carbonitrile 930 mg of (3-bromo-2,5-difluorophenyl)acetonitrile, 373 mg sodium hyride (60% dispersion in oil), and 10 ml anhydrous dimethyl sulfoxide were placed under nitrogen in an oven dried flask and stirred at room temperature for 45 minutes. 0.71 ml 2-chloroethyl ether was added and the mixture was stirred overnight. 0.53 ml glacial acetic acid was added and the reaction was diluted with water and extracted with ethyl acetate. The organic phase was extracted two times with 5% sodium chloride, dried over magnesium sulfate, filtered, concentrated, and purified by flash chromatography on silica. The product fractions were concentrated and vacuum dried to give 748 mg of product. GCMS (M) 301; 1H NMR (400 MHz, DMSO-d6) δ ppm 2.03-2.14 (m, 2H) 2.16-2.25 (m, 2H)

3.68 (td, J=12.15, 1.75 Hz, 2H) 4.01 (dd, J=12.35, 2.42 Hz, 2H) 7.41 (ddd, J=9.33, 5.84, 3.09 Hz, 1H) 7.85 (ddd, J=7.85, 5.03, 2.95 Hz, 1H).

Step 9: Preparation of 4-(3-bromo-2,5-difluorophenyl)tetrahydro-2H-pyran-4-carboxamide 748 mg of 4-(3-bromo-2,5-difluorophenyl)tetrahydro-2H-pyran-4-carbonitrile, and 417 mg of ground potassium hydroxide were placed in an oven dried vial and evacuated/nitrogen filled three times. 20 ml anhydrous tertiary butyl alcohol was added and the mixture was heated at 80° C. for 1 hour. The reaction was cooled, concentrated, diluted with ethyl acetate, extracted one time with water, and three times with 5% sodium chloride, dried over magnesium sulfate, filtered, and concentrated. The residue was triturated with 50% diethyl ether in hexanes, filtered and dried under vacuum to give 631 mg of product. LCMS (M+H) 320; 1H NMR (400 MHz, DMSO-d6) δ ppm 1.91 (dt, J=13.63, 6.75 Hz, 2H) 2.28 (d, J=13.43 Hz, 2H) 3.65 (dd, J=6.44, 3.76 Hz, 4H) 7.03 (br. s., 1H) 7.09 (br. s., 1H) 7.30 (ddd, J=10.07, 5.77, 3.22 Hz, 1H) 7.65 (ddd, J=7.59, 4.90, 3.09 Hz, 1H).

Step 10: Preparation of 4-(2,5-difluoro-3-{[4-(1-methyl-1H-pyrazol-5-yl)phenyl]-thio}phenyl)tetrahydro-2H-pyran-4-carboxamide 405 mg of 4-(3-bromo-2,5-difluorophenyl)tetrahydro-2H-pyran-4-carboxamide, 265 mg of 4-(1-methyl-1H-pyrazol-5-yl)benzenethiol, 33.5 mg of bis[(2-diphenylphosphino)phenyl]ether, 74.5 mg of tetrakis(triphenylphosphin)palladium (0) were placed in an oven-dried vial and evacuated/nitrogen filled three times. 6 ml of anhydrous 1,4-dioxane and 3.8 ml 2 M cesium carbonate were added and the mixture was heated at 80° C. overnight. The reaction was cooled, concentrated, and purified by reverse phase chromatography. The product fractions were diluted into ethyl acetate, extracted with 5% aqueous sodium bicarbonate, dried with magnesium sulfate, filtered, and concentrated. It was purified a second time by flash chromatography on silica. The product fractions were concentrated and vacuum dried to give 137 mg of product. HRMS (M+H) calc. 430.1401, found 430.1459; 1H NMR (400 MHz, DMSO-d6) δ ppm 1.93 (dt, J=13.90, 6.88 Hz, 2H) 2.29 (d, J=13.70 Hz, 2H) 3.66 (dd, J=6.44, 3.76 Hz, 4H) 3.87 (s, 3H) 6.46 (d, J=1.88 Hz, 1H) 7.01-7.07 (m, 2H) 7.09 (br. s., 1H) 7.28 (ddd, J=9.87, 6.11, 3.09 Hz, 1H) 7.44 (ddd, J=8.53, 2.28, 2.08 Hz, 2H) 7.48 (d, J=1.88 Hz, 1H) 7.57 (dt, J=8.59, 2.15 Hz, 2H).

Step 11: Preparation of 4-(2,5-difluoro-3-{[4-(1-methyl-1H-pyrazol-5-yl)phenyl]-thio}phenyl)-N-methyltetrahydro-2H-pyran-4-carboxamide 106 mg of 4-(2,5-difluoro-3-{[4-(1-methyl-1H-pyrazol-5-yl)phenyl]thio}phenyl)-tetrahydro-2H-pyran-4-carboxamide, 48.6 mg of sodium hydride (60% dipersion in oil), and 10 ml anhydrous tetrahydrofuran were placed under nitrogen in an oven dried vial and stirred at room temperature for 1 hour. 129 mg of iodomethane was added and the mixture was stirred at room temperature for 1 hour. 0.07 ml glacial acetic acid was added and the reaction was diluted with water and extracted two times with ethyl acetate. The combined organic layers were extracted with 5% sodium chloride, dried with magnesium sulfate, filtered, concentrated, and purified by reverse phase chromatography. The product fractions were diluted into ethyl acetate, extracted with 5% aqueous sodium bicarbonate, dried with magnesium sulfate, filtered, concentrated and vacuum dried to give 28 mg of product. HRMS (M+H) calc. 444.1557, found 444.1658; 1H NMR (400 MHz, DMSO-d6) δ ppm 1.89-1.99 (m, 2H) 2.22-2.31 (m, 2H) 2.54 (d, J=4.57 Hz, 3H) 3.60-3.68 (m, J=5.91, 4.03 Hz, 4H) 3.86 (s, 3H) 6.44 (d, J=1.88 Hz, 1H) 7.09 (ddd, J=7.85, 5.03, 2.95 Hz, 1H) 7.30 (ddd, J=9.67, 6.04, 3.09 Hz, 1H) 7.38-7.45 (m, 3H) 7.47 (d, J=1.88 Hz, 1H) 7.56 (dt, J=8.66, 2.11 Hz, 2H).

Example 20

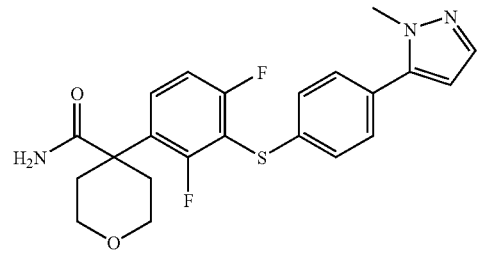

4-(2,4-difluoro-3-{[4-(1-methyl-1H-pyrazol-5-yl)phenyl]thio}phenyl)-tetrahydro-2H-pyran-4-carboxamide Step 1: Preparation of 4-(2,3,4-trifluorophenyl)tetrahydro-2H-pyran-4-carbonitrile 1 g of 2,3,4-trifluorophenylacetonitrile, 0.52 g sodium hydride (60% dispersion in oil), and 10 mL of anhydrous dimethyl sulfoxide were placed under nitrogen in an oven-dried vial and stirred at room temperature for 30 minutes. 0.733 mL of 2-chloroethyl ether was added, and the mixture was stirred at room temperature overnight. The reaction was diluted with water and extracted three times with ethyl acetate. The combined organic layers were extracted with 1 N hydrogen chloride and 5% sodium chloride, dried over magnesium sulfate, filtered, concentrated, and purified by flash chromatography on silica. The product fractions were concentrated and vacuum dried to give 175 mg of product. GCMS (M) 241; 1H NMR (400 MHz, DMSO-$d_6$) δ ppm 2.10 (ddd, J=13.43, 11.95, 4.43 Hz, 2H) 2.16-2.24 (m, 2H) 3.68 (td, J=12.15, 1.75 Hz, 2H) 4.01 (dd, J=12.49, 3.89, 1.34 Hz, 2H) 7.31-7.50 (m, 2H).

Step 2: Preparation of S-[4-(1-methyl-1H-pyrazol-5-yl)phenyl]ethanethioate 1.60 g of 4-(1-methyl-1H-pyrazol-5-yl)benzenethiol was placed under nitrogen and dissolved in 20 mL of anhydrous tetrahydrofuran. 0.200 g of 4-dimethyl-aminopyridine and 0.70 mL of anhydrous pyridine were added followed by the addition of 0.960 mL of acetic anhydride. The reaction was stirred for 10 minutes, then diluted with ether, extracted with water, extracted with 0.1 N aqueous hydrochloric acid, extracted with 1% aqueous sodium bicarbonate, dried with magnesium sulfate, filtered, concentrated and flash chromatographed to give 1.57 g of product. LCMS (M+H) 233; 1H NMR (400 MHz, DMSO-$d_6$) δ ppm 2.47 (s, 3H) 3.88 (s, 3H) 6.49 (d, J=1.71 Hz, 1H) 7.49 (d, J=1.71 Hz, 1H) 7.52-7.55 (m, 2H) 7.62-7.66 (m, 2H).

Step 3: Preparation of 4-(2,4-difluoro-3-{[4-(1-methyl-1H-pyrazol-5-yl)phenyl]thio}phenyl)tetrahydro-2H-pyran-4-carbonitrile 169 mg of S-[4-(1-methyl-1H-pyrazol-5-yl)phenyl] ethanethioate and 5 mL of anhydrous 1-methyl-2-pyrrolidinone were placed under nitrogen in an oven-dried vial and chilled to 0° C. 0.726 mL of 1 M potassium t-butoxide in tetrahydrofuran was added, and the mixture was stirred at 0° C. for 1 hour. 175 mg of 4-(2,3,4-trifluorophenyl)tetrahydro-2H-pyran-4-carbonitrile dissolved in 2 mL of anhydrous 1-methyl-2-pyrrolidinone was added, and the mixture was stirred at 45° C. overnight. The reaction was cooled and 0.041 mL of glacial acetic acid was added, diluted into ethyl acetate, extracted three times with 5% sodium chloride, dried over magnesium sulfate, filtered, concentrated, and purified by reverse phase chromatography. The product fractions were diluted into ethyl acetate, extracted with 5% aqueous sodium bicarbonate, dried with magnesium sulfate, filtered, and concentrated, and vacuum dried to give 48.1 mg of product. LC/MS (M+H)-412; 1H NMR (400 MHz, DMSO-$d_6$) δ ppm 2.11 (td, J=12.76, 4.30 Hz, 2H) 2.19-2.26 (m, 2H) 3.68 (td, J=12.08, 1.61 Hz, 2H) 3.82 (s, 3H) 3.97-4.05 (m, 2H) 6.40 (d, J=1.88 Hz, 1H) 7.27 (ddd, J=8.59, 2.42, 2.15 Hz, 2H) 7.40-7.46 (m, 2H) 7.50 (ddd, J=8.73, 2.28, 2.15 Hz, 2H) 7.72 (td, J=8.86, 6.18 Hz, 1H).

Step 4: Preparation of 4-(2,4-difluoro-3-{[4-(1-methyl-1H-pyrazol-5-yl)phenyl]thio}-phenyl)tetrahydro-2H-pyran-4-carboxamide 45 mg of 4-(2,4-difluoro-3-{[4-(1-methyl-1H-pyrazol-5-yl)phenyl]thio}phenyl)-tetrahydro-2H-pyran-4-carbonitrile was placed under nitrogen in an oven-dried vial. 1.5 mL of a 4:1 (v/v) solution of trifluoroacetic acid-sulfuric acid was added, and the mixture was stirred at room temperature for four days. The reaction was diluted into ethyl acetate and extracted with 10% sodium carbonate, water, and 5% sodium chloride, dried over magnesium sulfate, filtered, concentrated and dried under vacuum to give 32 mg of product. HRMS (M+H) calc. 430.1401, found 430.1508; 1H NMR (400 MHz, DMSO-$d_6$) δ ppm 1.89-2.00 (m, 2H) 2.30 (d, J=13.96 Hz, 2H) 3.66 (dd, J=6.71, 3.76 Hz, 4H) 3.82 (s, 3H) 6.39 (d, J=2.15 Hz, 1H) 7.04 (br. s., 1H) 7.06 (br. s., 1H) 7.20 (ddd, J=8.53, 2.15, 1.95 Hz, 2H) 7.30-7.37 (m, 1H) 7.46 (dt, J=9.06, 2.18 Hz, 3H) 7.67 (td, J=8.79, 6.04 Hz, 1H).

Example 21

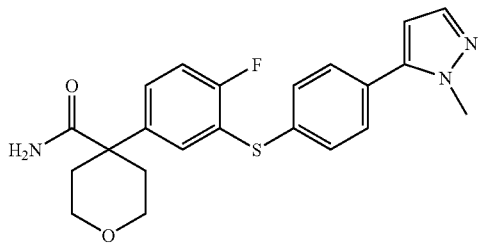

4-(4-fluoro-3-(4-(1-methyl-1H-pyrazol-5-yl)phenylthio)phenyl)-tetrahydro-2H-pyran-4-carboxamide Step 1: Preparation of 2-(3-bromo-4-fluorophenyl)acetonitrile A solution of 2-bromo-4-(bromomethyl)-1-fluorobenzene (5.0 g, 18.7 mmol) in DMSO (80 mL) was treated with sodium cyanide (1.16 g, 22.4 mmol) and stirred for 18 hours. The reaction was poured into ethyl acetate and washed 4× with 5% sodium chloride. The organic layer was dried over magnesium sulfate, filtered, and concentrated to an oil. Purification by silica gel column chromatography provided the title compound as a light amber oil (3.6 g, 75%). LC/MS: 10%-90% CH3CN:H20 gradient over 5 minutes: 2.57 min., 214, 216 (M+H); $^1$H NMR (400 MHz, CHLOROFORM-d) δ ppm 3.73 (s, 2H) 7.15 (t, J=8.40 Hz, 1H) 7.20-7.32 (m, 1H) 7.56 (dd, J=6.25, 2.35 Hz, 1H).

Step 2: Preparation 4-(3-bromo-4-fluorophenyl)-tetrahydro-2H-pyran-4-carbonitrile A solution of 2-(3-bromo-4-fluorophenyl)acetonitrile (300 mg, 1.40 mmol) in DMSO (5 mL) was treated with sodium hydride (120 mg, 3.0 mmol) and stirred for 1 hour. The reaction was then treated with 2-chloroethyl ether (409 mg, 0.335 mL, 2.8 mmol) and stirred for 2 hours. The reaction was quenched with acetic acid, poured into water, and extracted 3× with ethyl acetate. The organic layer was washed with brine, dried over magnesium sulfate, filtered, and concentrated to an oil. Purification by silica gel column chromatography provided the title compound as a light amber oil (240 mg, 30%). $^1$H NMR (400 MHz, CHLOROFORM-d) δ ppm 2.05-2.15 (m, 4H) 3.86-3.94 (m, 2H) 4.07-4.11 (m, 1H) 4.10-4.15 (m, 1H) 7.19 (dd, J=8.70, 8.11 Hz, 1H) 7.43 (ddd, J=8.60, 4.30, 2.54 Hz, 1H) 7.68 (dd, J=6.25, 2.54 Hz, 1H).

Step 3: Preparation of 4-(4-fluoro-3-(4-(1-methyl-1H-pyrazol-5-yl)phenylthio)phenyl)-4-tetrahydro-2H-pyran-4-carboxamide A solution of 4-(3-bromo-4-fluorophenyl)-tetrahydro-2H-pyran-4-carbonitrile (100 mg, 0.352 mmol) in t-butanol (1 mL) was treated with powdered potassium hydroxide (59.2 mg, 1.06 mmol) and heated to 80° C. for 1.5 hours. The reaction was cooled to room temperature, diluted with water, and the resulting solid was filtered off and dried (93 mg). The solid was combined with S-4-(1-methyl-1H-pyrazol-5-yl) phenyl ethanethioate (71.5 mg, 0.31 mmol), tetrakis(triphenylphosphine) palladium (57.8 mg, 0.05 mmol) and bis(2-diphenylphosphinophenyl)ether (32.3 mg, 0.06 mmol) in 1,4-dioxane (3 mL). The mixture was degassed and purged with Ar(g), aqueous sodium carbonate (1.21 mL, 2M) was added, and the resulting mixture heated to 85° C. for 18 hours. The reaction was cooled to room temperature and concentrated. The residue was dissolved in DMSO (1 mL) and purified by reverse phase chromatography to give the title compound (38 mg, 39%). LC/MS: 10%-90% CH3CN:H20 gradient over 5 minutes: 2.72 min., 412 (M+H).

Example 22

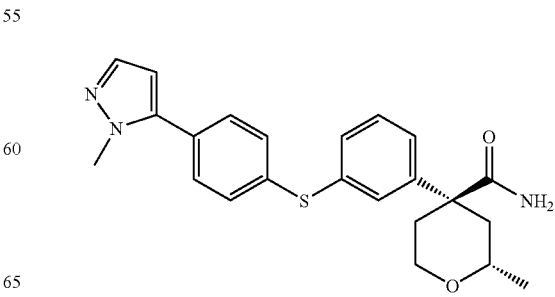

(2S,4R)-2-methyl-4-(3-(4-(1-methyl-1H-pyrazol-5-yl)phenylthio)phenyl)-tetrahydro-2H-pyran-4-carboxamide

Step 1: Preparation of (S)-ethyl 2-(2-ethoxy-2-oxoethoxy)propanoate

Ethyl (S)-(−)-lactate (738 g, 6247 mmol, 1 eq.) and potassium carbonate (856 g, 6.193 mmol, 1 eq.) were dissolved in N,N-dimethylformamide (7.0 L) and stirred at room temperature for 20 min. Ethyl bromoacetate (1049 g, 6.200 mmol, 0.98 eq.) was added to the reaction mixture and stirred at room temperature for 24 h. The reaction was diluted with water (25 L) and extracted with dichloromethane (3×3 L). The combined organic phases were washed with water (1×3 L) and concentrated to an oil. The oil was distilled under vacuum (1 mmHg) to afford 418 g (33%) of the desired intermediate. LC/MS (M+H)=205.

Step 2: Preparation of (S)-2-(2-hydroxyethoxy)propan-1-ol (S)-ethyl 2-(2-ethoxy-2-oxoethoxy)propanoate (418 g, 2050 mmol, 1 eq.) was dissolved in THF (3.0 L). While stirring, lithium aluminum hydride (2.52 L, 2520 mmol, 1.2 eq.) was added dropwise to the reaction mixture, keeping the temperature below 60° C. The reaction mixture was stirred for 24 h. The reaction was quenched by dropwise addition of water (47 mL). A solution of sodium hydroxide (94 mL, 2.5 N) was added to the mixture followed by the addition of water (141 mL). The mixture was stirred for 30 min., and the solids were filtered and rinsed with acetone. The filtrate was concentrated to a neat oil. The oil was distilled under vacuum (<1 mmHg, 90-105° C.) to afford 146 g (59%) of the desired alcohol. 1H NMR (400 MHz, CHLOROFORM-d) δ ppm 0.93-1.08 (m, 3H) 3.20-3.81 (m, 7H) 4.10-4.33 (m, 1H) 4.50 (d, J=17.59 Hz, 1H); LCMS (M+H)=121.

Step 3: Preparation of (S)-1-iodo-2-(2-iodoethoxy)propane

Triphenyl phosphine (45.0 g, 166 mmol, 4 eq.) and imidazole (11.7 g, 166 mmol, 4 eq.) were dissolved in acetonitrile (100 mL) and diethyl ether (300 mL). Iodine (52.4 g, 206 mmol, 5 eq.) was added slowly to the reaction mixture and stirred for 30 min. (S)-2-(2-hydroxyethoxy)propan-1-ol (5.0 g, 42 mmol, 1 eq.) was added dropwise to the reaction mixture and stirred for 24 h avoiding light exposure. The resulting solids were filtered and washed with ethyl acetate. The filtrate was concentrated under reduced pressure to an oily residue. The residue was filtered through a silica column using 5% ethyl acetate/heptane to afford an oil. The resulting oil was purified further by chiral chromatography to remove any remains (5%) of (R)-1-iodo-2-(2-iodoethoxy)propane. GC/MS m/z=340; 1H NMR (400 MHz, CHLOROFORM-d) δ ppm 1.28 (d, J=6.25 Hz, 3H) 3.14-3.29 (m, 4H) 3.43-3.54 (m, 1H) 3.67-3.82 (m, 2H).

Procedure for Enhancement of Chiral Purity of (S)-1-Iodo-2-(2-Iodoethoxy)propane Separations performed with a Berger MultiGram II SFC chromatograph using a Chiralpak AS-H 30×250 mm column from Chiral Technologies, Inc. Isocratic elution with 5% MeOH/95% $CO_2$ at 70 ml/min. Samples were dissolved at 50 mg/ml in MeOH, 2 ml/injection. Peak one is the minor enantiomer, peak 2 is the major enantiomer and peak 3 is an unknown impurity. Analytical analysis was performed with a Chiralpak AD-H 4.6×250 mm column from Chiral Technologies, Inc. Isocratic elution using 20% MeOH/80% $CO_2$ at 3 ml/min. Peak 1 eluted at 1.86 minutes, Peak 2 eluted at 1.99 minutes, and the impurity peak eluted at 2.26 minutes.

Step 4: Preparation of (2S,4R)-4-(3-bromophenyl)-2-methyl-tetrahydro-2H-pyran-4-carbonitrile 3-Bromophenyl acetonitrile (1.04 g, 5.3 mmol, 1 eq.) and (S)-1-iodo-2-(2-iodoethoxy)propane (2.13 g, 6.25 mmol, 1.2 eq.) were dissolved in dimethyl sulfoxide (20 mL). Sodium hydride (405 mg, 10.1 mmol, 1.9 eq.) was added to the reaction mixture and stirred for 1 h at room temperature. The reaction mixture was diluted with water (10 mL) and ethyl acetate (10 mL), and the layers were separated. The organic phase was washed with 1 M HCl (1×10 ml), water (1×10 ml), and brine (1×10 ml). The organic phase was concentrated under vacuum to afford a yellow liquid. The mixture of diastereomers (1:1) formed, were separated by reverse phase chromatography (40-90% acetonitrile-water) to obtain the title compound (350 mg, 24%) as a single isomer. Stereochemistry confirmed by NMR. 1H NMR (400 MHz, CHLOROFORM-d) δ ppm 1.29 (d, J=6.14 Hz, 3H) 1.71 (dd, J=13.31, 11.26 Hz, 1H) 2.02-2.12 (m, 3H) 3.91-4.00 (m, 2H) 4.10-4.16 (m, 1H) 7.31 (t, J=8.02 Hz, 1H) 7.43-7.46 (m, 1H) 7.50 (s, 1H) 7.63 (t, J=1.88 Hz, 1H). LCMS (M+H)=280 (100%), 282 (98.5%).

Step 5: Preparation of (2S,4R)-2-methyl-4-(3-(4-(1-methyl-1H-pyrazol-5-yl)phenylthio)phenyl)-tetrahydro-2H-pyran-4-carbonitrile 4-(1-methyl-1H-pyrazol-5-yl)phenyl ethanethioate (296 mg, 1.27 mmol, 1 eq.), (2S,4R)-4-(3-bromophenyl)-2-methyl-tetrahydro-2H-pyran-4-carbonitrile (350 mg, 1.20 mmol, 1 eq.), palladium tetrakis (80 mg, 0.07 mmol, 0.05 eq.) and DPEphos (37 mg, 0.07 mmol, 0.05 eq.), potassium tert-butoxide (3.75 mL of 1 M in THF, 3.75 mmol, 3 eq.) were mixed in isopropanol (5 mL) at room temperature. Nitrogen was bubbled through the reaction mixture for 5 minutes. The solution was heated to 65° C. for 24 hours. The solution was cooled to room temperature and diluted with ethyl acetate (5 mL) and water (5 mL). The layers were separated, and the aqueous phase was extracted with ethyl acetate (2×5 ml). The combined organic phases were dried over sodium sulfate, and the solvent was removed at reduced pressure. The resulting oil was isolated by reverse phase chromatography (40-90% acetonitrile-water) to give the desired product (49.4 mg, 10%). 1H NMR (400 MHz, DMSO-d6) δ ppm 1.19 (d, J=5.86 Hz, 3H) 1.62-1.74 (m, 1H) 1.98 (td, J=12.81, 4.39 Hz, 1H) 2.04-2.12 (m, 1H) 2.18 (d J=13.18 Hz, 1H) 3.64-3.80 (m, 2H) 3.72 (d, J=12.45 Hz, 1H) 3.85 (s, 3H) 4.03 (dd, J=12.08, 4.03 Hz, 1H) 6.41 (s, 1H) 7.36-7.59 (m, 9H); ES-HRMS m/z 390.1696 (M+H calc.: 390.1640).

Step 6: Preparation of (2S,4R)-2-methyl-4-(3-(4-(1-methyl-1H-pyrazol-5-yl)phenylthio)phenyl)-tetrahydro-2H-pyran-4-carboxamide (2S,4R)-2-methyl-4-(3-(4-(1-methyl-1H-pyrazol-5-yl)phenylthio)phenyl)-tetrahydro-2H-pyran-4-carbonitrile (443 mg, 1.14 mmol, 1 eq.) and potassium hydroxide (300 mg, 5.4 mmol, 4.7 eq.) were dissolved in tert-butyl alcohol (10.0 mL). The mixture stirred at 60° C. for 24 h. The mixture was diluted with water (10 mL) and extracted with ethyl acetate (2×10 mL). The organic phase was concentrated to a solid. The crude solid was purified by reverse phase chromatography (40-90% acetonitrile-water) to afford the title product (143 mg, 31%) as a solid. 1H NMR (400 MHz, DMSO-d6) δ ppm 1.10 (d, J=6.22 Hz, 3H) 1.20-1.31 (m, 1H) 1.50-1.63 (m, 1H) 2.45-2.62 (m, 3H) 3.40-3.51 (m, 2H) 3.83 (s, 3H) 6.40 (d, J=1.83 Hz, 1H) 7.10 (s, 1H) 7.23-7.55 (m, 9H) 8.12 (s, 1H); ES-HRMS m/z 408.1816 (M+H calc.: 408.1746).

Example 23

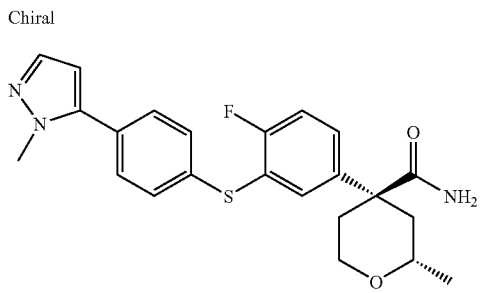

(2S,4R)-4-(4-fluoro-3-(4-(1-methyl-1H-pyrazol-5-yl)phenylthio)phenyl)-2-methyl-tetrahydro-2H-pyran-4-carboxamide The title compound was made using the methods described in example 15 using 2-(3-bromo-4-fluorophenyl)acetonitrile as starting material.

1H NMR (400 MHz, CHLOROFORM-d) δ ppm 1.22 (d, J=6.25 Hz, 3H) 1.53 (dd, J=13.29, 11.14 Hz, 1H) 1.82-1.93 (m, 1H) 2.27-2.41 (m, 2H) 3.67-3.77 (m, 2H) 3.91 (s, 3H) 3.96-4.03 (m, 1H) 5.60 (br. s., 1H) 6.02 (br. s., 1H) 6.34 (d, J=2.15 Hz, 1H) 7.15 (t, J=8.50 Hz, 1H) 7.25-7.35 (m, 4H) 7.37-7.43 (m, 1H) 7.49 (dd, J=6.64, 2.35 Hz, 1H) 7.59 (d, J=1.95 Hz, 1H); ES-HRMS m/z 426.1662 (M+H calc.: 426.1651).

Example 24

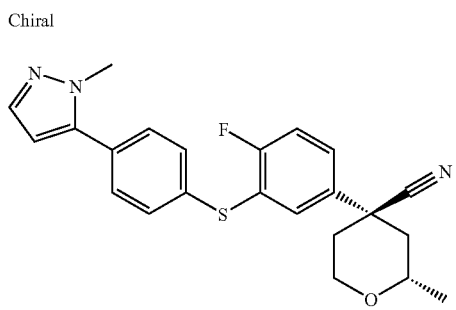

(2S,4R)-4-(4-fluoro-4-(4-(1-methyl-1H-pyrazol-5-yl)phenylthio)phenyl)-2-methyl-tetrahydro-2H-pyran-4-carbonitrile Procedures used in the preparation of the compound of example 27, below, was used to prepare the following compound using 2-(3-bromo-4-fluorophenyl)acetonitrile as starting material:

1H NMR (400 MHz, DMSO-d$_6$) δ ppm 1.16-1.18 (d, 3H), 1.64-1.7 (m, 1H), 1.92-1.99 (m, 1H), 2.07-2.11 (m, 1H), 2.17-2.2 (m, 1H), 3.64-3.73 (m, 2H), 3.84 (s, 3H), 4.0-4.04 (m, 1H), 6.41 (m, 1H), 7.35-7.38 (d, 2H), 7.45-7.49 (m, 2H), 7.53-7.55 (d, 2H), 7.63 (m, 1H), 7.67 (m, 1H); HRMS M+H calc.: 408.1546, found 408.1619.

Example 25

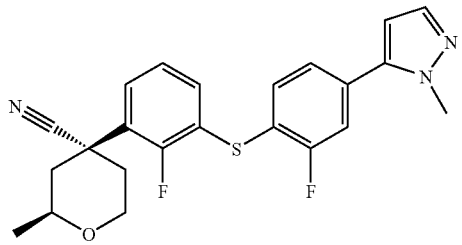

(2S,4R)-4-(2-fluoro-3-(2-fluoro-4-(1-methyl-1H-pyrazol-6-yl)phenylthio)phenyl)-2-methyl-tetrahydro-2H-pyran-4-carbonitrile Step 1: Preparation of (4-bromo-3-fluorophenyl)(morpholino)methanone To a solution of 4-bromo-3-fluorobenzoic acid (3.0 g, 14 mmol) in methylene chloride (50 mL) was added 1-ethyl-3-(3'-dimethylaminopropyl)carbodiimide hydrochloride (3.41 g, 1.3 mmol), dimethylaminopyridine (502 mg, 4.11 mmol), and morpholine (1.22 g, 14 mmol). After stirring for 3 hours at ambient temperature the reaction was poured into water (300 mL), washed with water (2×100 mL), and the organic dried over magnesium sulfate, filtered and the solvent removed by evaporation under reduced pressure, to provide the title compound (3.68 g) as an oil. $^1$H NMR (400 MHz, CHLOROFORM-d) δ ppm 3.31-3.92 (m, 8H) 7.05-7.13 (m, 1H) 7.20 (dd, J=8.40, 1.95 Hz, 1H) 7.62 (dd, J=8.20, 6.64 Hz, 1H). LCMS: m/z [MH+] 288.0, 290.0.

Step 2: Preparation of 1-(4-bromo-3-fluorophenyl)ethanone

To an ice-bath cooled solution of (4-bromo-3-fluorophenyl)(morpholino)methanone (3.14 mg, 10.9 mmol) in anhydrous tetrahydrofuran (45 mL), under argon, was added methylmagnesium chloride (1.22 g, 16.4 mmol). The reaction was stirred at ice bath temperature for 1 hour then allowed to warm to ambient temperature. The reaction was poured into water (350 mL), extracted with ethyl acetate (3×75 mL), washed with brine (100 mL), dried over magnesium sulfate, filtered and the solvent removed by evaporation under reduced pressure, to provide the title compound (2.8 g) as a liquid. $^1$H NMR (400 MHz, CHLOROFORM-d) δ ppm 2.60 (s, 3H) 7.52-7.77 (m, 3H).

Step 3: Preparation of 5-(4-bromo-3-fluorophenyl)-1-methyl-1H-pyrazole

To a solution of 1-(4-bromo-3-fluorophenyl)ethanone (2.8 g, 12 mmol) in N,N-dimethylformamide (10 mL) was added N,N-dimethylformamide dimethyl acetal (3.45 mL, 26 mmol). The reaction was heated to reflux for three hours, cooled to room temperature, treated with methyl hydrazine (2.5 mL, 46 mmol), and heated to 75° C. for 18 hours. The reaction was cooled to room temperature, extracted with ethyl acetate (3×75 mL), washed with brine (100 mL), dried over magnesium sulfate, filtered and the solvent removed by evaporation under reduced pressure. The residue was purified by flash chromatography on silica gel eluting with a solvent gradient of ethyl acetate:heptane (20:80, by volume) changing to ethyl acetate:heptane (60:40 by volume), to provide the title compound (1.66 g) as a solid. $^1$H NMR (400 MHz, CHLOROFORM-d) δ ppm 3.91 (s, 3H) 6.34 (d, J=1.95 Hz, 1H) 7.11 (dd, J=8.01, 1.76 Hz, 1H) 7.20 (dd, J=8.99, 1.95 Hz, 1H) 7.53 (d, J=1.95 Hz, 1H) 7.65 (dd, J=8.20, 7.03 Hz, 1H).

LCMS: m/z [MH+] 255.0, 257.0.

Step 4: Preparation of S-2-fluoro-4-(1-methyl-1H-pyrazol-5-yl)phenyl ethanethioate To a solution of 5-(4-bromo-3-fluorophenyl)-1-methyl-1H-pyrazole (120 mg, 0.470 mmol) in degassed, anhydrous 1,4-dioxane (13 mL), under argon, was added palladium acetate (8.1 mg, 0.036 mmol), bis(2-diphenylphosphinophenyl)ether (9.7 mg, 0.018 mmol), cesium carbonate (234 mg, 0.719 mmol), and triisopropylsilane thiol (205 mg, 0.231 mL, 1.08 mmol). The reaction was heated to 95° C. for 45 minutes, cooled to room temperature, and treated with acetic anhydride (1.5 mL). After 18 hours the reaction was filtered, and the filtrate was extracted with ethyl acetate (3×75 mL), washed with brine (100 mL), dried over magnesium sulfate, filtered and the solvent removed by evaporation under reduced pressure. The residue was purified by flash chromatography on silica gel eluting with a solvent gradient of ethyl acetate:heptane (5:95, by volume) changing to ethyl acetate:heptane (40:60 by volume), to provide the title compound (50 mg) as a solid. $^1$H NMR (400 MHz, CHLOROFORM-d) δ ppm 2.50 (s, 3H) 3.96 (s, 3H) 6.38 (d, J=1.95 Hz, 1H) 7.23-7.29 (m, 2H) 7.51 (dd, J=8.30, 6.93 Hz, 1H) 7.55 (d, J=2.15 Hz, 1H).

LCMS: m/z [MH+] 251.1

Step 5: Preparation of (2S,4R)-4-(2-fluoro-3-(2-fluoro-4-(1-methyl-1H-pyrazol-5-yl)phenylthio)phenyl)-2-methyl-tetrahydro-2H-pyran-4-carbonitrile To a solution of S-2-fluoro-4-(1-methyl-1H-pyrazol-5-yl)phenyl ethanethioate (100 mg, 0.400 mmol) in degassed, anhydrous 1,4-dioxane (3 mL), under argon, was added, ((2S,4R)-4-(3-bromo-2-fluorophenyl)-2-methyl-tetrahydro-2H-pyran-4-carbonitrile) (119 mg, 0.0400 mmol), palladium acetate (13.7 mg, 0.060 mmol), bis(2-diphenylphosphinophenyl)ether (21.5 mg, 0.040 mmol), and solid cesium carbonate (391 mg, 1.20 mmol). After heating to 85° C. for 18 hours the reaction was cooled to room temperature, filtered and purified by reverse phase HPLC, to provide the title compound (44 mg) as a glassy solid. $^1$H NMR (400 MHz, DMSO-d$_6$) δ ppm 1.19 (d, J=6.22 Hz, 3H) 1.72 (dd, J=13.18, 10.98 Hz, 1H) 1.96-2.05 (m, 1H) 2.19 (dt, J=13.36, 1.19 Hz, 1H) 2.28 (dt, J=13.45, 2.24 Hz, 1H) 3.69-3.81 (m, 2H) 3.89 (s, 3H) 4.00-4.06 (m, 1H) 6.52 (d, J=1.83 Hz, 1H) 7.28-7.35 (m, 2H) 7.38-7.51 (m, 4H) 7.58-7.63 (m, 1H).

LCMS: m/z [MH+] 425.1.

Example 26

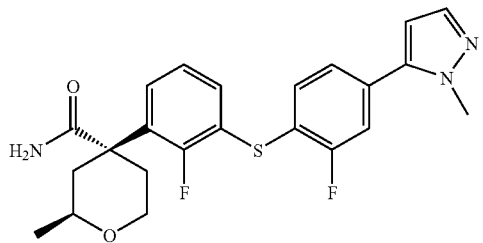

(2S,4R)-4-(2-fluoro-3-(2-fluoro-4-(1-methyl-1H-pyrazol-5-yl)phenylthio)phenyl)-2-methyl-tetrahydro-2H-pyran-4-carboxamide A solution of compound of example 25 (98 mg, 0.23 mmol) in t-butanol (2 mL) was treated with powdered potassium hydroxide (41.6 mg, 0.741 mmol) and heated to 70° C. for 18 hours. The reaction was cooled to ambient temperature, filtered and purified by reverse phase HPLC to provide the title compound (38 mg) as a solid. $^1$H NMR (400 MHz, DMSO-d$_6$) δ ppm 1.09 (d, J=6.59 Hz, 3H) 1.36-1.48 (m, 1H) 1.71-1.83 (m, 1H) 2.33-2.49 (m, 2H) 3.57-3.73 (m, 2H) 3.77-3.85 (m, 1H) 3.89 (s, 3H) 6.51 (d, J=1.46 Hz, 1H) 7.12 (s, 2H) 7.25 (t, J=6.59 Hz, 3H) 7.38 (d, J=8.05 Hz, 1H) 7.42-7.51 (m, 2H) 7.59 (d, J=8.79 Hz, 1H). LCMS: m/z [MH+] 444.2.

Example 27

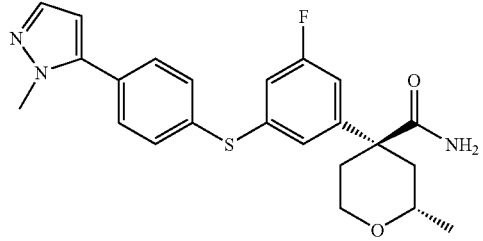

(2S,4R)-4-(3-fluoro-5-(4-(1-methyl-1H-pyrazol-5-yl)phenylthio)phenyl)-2-methyl-tetrahydro-2H-pyran-4-carboxamide

Step 1: Preparation of (2S,4R)-4-(3-bromo-5-fluorophenyl)-2-methyl-tetrahydro-2H-pyran-4-carbonitrile 2-(3-bromo-5-fluorophenyl)acetonitrile (1.40 g, 4.6 mmol, 1 eq.) and (S)-1-iodo-2-(2-iodoethoxy)propane (2.30 g, 6.87 mmol, 1.5 eq) were dissolved in dimethyl sulfoxide (10 ml). Sodium hydride (450 mg, 11 mmol, 2.5 eq.) was added to the reaction mixture and stirred for 1 h at room temperature. The reaction mixture was diluted with water (10 ml) and ethyl acetate (10 ml), and the layers separated. The organic phase was washed with 1 M HCl (1×10 ml), water (1×10 ml) and brine (1×10 ml). The organic phase was concentrated under vacuum to afford a diastereomeric mixture of (2S,4R)-4-(3-bromo-5-fluorophenyl)-2-methyl-tetrahydro-2H-pyran-4-carbonitrile and (2S,4S)-4-(3-bromo-5-fluorophenyl)-2-methyl-tetrahydro-2H-pyran-4-carbonitrile (1:1). The diastereomeric mixture was separated by reverse phase chromatography (40-90% acetonitrile-water) to obtain the title compound (522 mg, 38%) as a single isomer. LCMS (M+1)= 298 (100%), 300 (98%).

Step 2: Preparation of (2S,4R)-4-(3-fluoro-5-(4-(1-methyl-1H-pyrazol-5-yl)phenylthio)phenyl)-2-methyl-tetrahydro-2H-pyran-4-carbonitrile

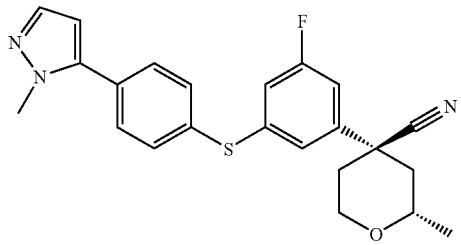

4-(1-methyl-1H-pyrazol-5-yl)phenyl ethanethioate (407 mg, 1.75 mmol, 1 eq.), (2S,4R)-4-(3-bromo-5-fluorophenyl)-2-methyl-tetrahydro-2H-pyran-4-carbonitrile (522 mg, 1.75 mmol, 1 eq.), palladium tetrakis (111 mg, 0.096 mmol, 0.05 eq.) and DPEphos (51.7 mg, 0.096 mmol, 0.05 eq.), potassium tert-butoxide (5.25 ml of 1 M in THF, 5.25 mmol, 3 eq.) were mixed in isopropanol (10 ml) at room temperature. Nitrogen was bubbled through the reaction mixture for 5 minutes. The solution was heated to 65° C. for 24 hours. The solution was cooled to room temp and diluted with ethyl acetate (5 ml) and water (5 ml). The layers separated and the aqueous phase was extracted with ethyl acetate (2×5 ml). The combined organic phases were dried over sodium sulfate and solvent removed at reduced pressure. The resulting oil was isolated by reverse phase chromatography (40-90% acetonitrile-water) to give the desired product (520 mg, 73%). 1H NMR (400 MHz, DMSO-d6) δ ppm 1.16 (d, J=6.59 Hz, 3H) 1.63-1.72 (m, 1H) 1.91-2.01 (m, 1H) 2.04-2.11 (m, 1H) 2.17 (d, J=13.91 Hz, 1H) 3.61-3.74 (m, 2H) 3.86 (s, 3H) 4.01 (dd, J=12.08, 3.29 Hz, 1H) 6.45 (s, 1H) 7.12 (d, J=8.79 Hz, 1H) 7.34-7.40 (m, 2H) 7.46-7.49 (m, 1H) 7.51-7.63 (m, 4H); ES-HRMS m/z 408.1611 (M+H calcd: 408.1546).

Step 3: Preparation of (2S,4R)-4-(3-fluoro-5-(4-(1-methyl-1H-pyrazol-5-yl)phenylthio)phenyl)-2-methyl-tetrahydro-2H-pyran-4-carboxamide (2S,4R)-4-(3-fluoro-5-(4-(1-methyl-1H-pyrazol-5-yl)phenylthio)phenyl)-2-methyl-tetrahydro-2H-pyran-4-carbonitrile (370 mg, 0.91 mmol, 1 eq.) and potassium hydroxide (428 mg, 7.6 mmol 8.7 eq.) was dissolved in tert-butyl alcohol (5.0 ml). The mixture stirred at 60° C. for 24 h. The mixture was diluted with water (10 ml) and extracted with ethyl acetate (2×10 ml). The organic phase was concentrated to a solid. The crude solid was purified by reverse phase chromatography (40-90% acetonitrile-water) to afford the title product (126 mg, 33%) as a solid. 1H NMR (400 MHz, DMSO-d6) δ ppm 1.09 (d, J=5.86 Hz, 3H) 1.21-1.30 (m, 1H) 1.51-1.62 (m, 2H) 2.41-2.56 (m, 2H) 3.37-3.49 (m, 2H) 3.81 (d, J=2.93 Hz, 1H) 3.85 (s, 3H) 6.44 (s, 1H) 7.01 (d, J=8.79 Hz, 1H) 7.09-7.18 (m, 2H) 7.22 (s, 1H) 7.35 (br. s., 1H) 7.42-7.48 (m, 2H) 7.57 (d, J=8.05 Hz, 2H); ES-HRMS m/z 426.1656 (M+H calc.: 426.1651).

Example 28

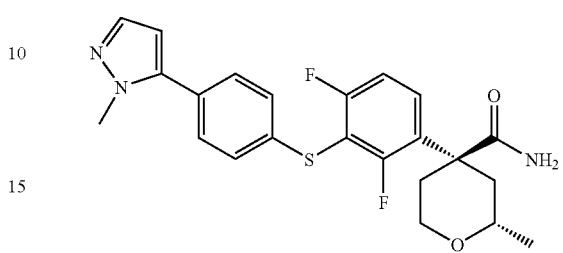

(2S,4R)-4-(2,4-difluoro-3-(4-(1-methyl-1H-pyrazol-5-yl)phenylthio)phenyl)-2-methyl-tetrahydro-2H-pyran-4-carboxamide

Step 1: Preparation of (2S,4R)-4-(3-bromo-2,4-difluorophenyl)-2-methyl-tetrahydro-2H-pyran-4-carbonitrile 2-(3-bromo-2,4-difluorophenyl)acetonitrile (1.60 g, 9.4 mmol, 1 eq.) and (S)-1-iodo-2-(2-iodoethoxy)propane (3.40 g, 10 mmol, 1.1 eq.) were dissolved in dimethyl sulfoxide (10 ml). Sodium hydride (828 mg, 21 mmol, 2.2 eq.) was added to the reaction mixture and stirred for 1 h at room temperature. The reaction mixture was diluted with water (10 ml) and ethyl acetate (10 ml) and the layers separated. The organic phase was washed with 1M HCl (1×10 ml), water (1×10 ml) and brine (1×10 ml). The organic phase was concentrated under vacuum to afford a diastereomeric mixture of (2S,4R)-4-(3-bromo-2,4-difluorophenyl)-2-methyl-tetrahydro-2H-pyran-4-carbonitrile and (2S,4S)-4-(3-bromo-2,4-difluorophenyl)-2-methyl-tetrahydro-2H-pyran-4-carbonitrile (1:1). The diastereomeric mixture was separated by reverse phase chromatography (30-85% acetonitrile-water) to obtain the title compound (251 mg, 11%) as a single isomer. LC/MS (M+1)=316 (100%), 318 (98%).

Step 2: Preparation of (2S,4R)-4-(2,4-difluoro-3-(4-(1-methyl-1H-pyrazol-5-yl)phenylthio)phenyl)-2-methyl-tetrahydro-2H-pyran-4-carbonitrile 4-(1-methyl-1H-pyrazol-5-yl)phenyl ethanethioate (233 mg, 1.0 mmol, 1 eq.) was dissolved in 1-methyl-2-pyrrolidinone (10 mL) and potassium tert-butoxide (1.0 ml of 1 M in THF, 1.0 mmol, 1 eq.) was added. The reaction mixture was followed by LCMS until complete conversion to the free thiol was observed. (2S,4R)-4-(3-bromo-2,4-difluorophenyl)-2-methyl-tetrahydro-2H-pyran-4-carbonitrile (251 mg, 0.98 mmol, 1.0 eq.) was added to the reaction mixture and stirred at 45° C. for 24 hrs. The solution was cooled to room temp and diluted with ethyl acetate (5 ml) and water (5 ml). The layers separated and the aqueous phase was extracted with ethyl acetate (2×5 ml). The combined organic phases were washed with brine (2×10 mL), dried over sodium sulfate and solvent removed at reduced pressure. The resulting oil was isolated by reverse phase chromatography (40-90% acetonitrile-water) to give the desired product (110 mg, 26%). 1H NMR (400 MHz, DMSO-d6) δ ppm 1.18 (d, J=6.59 Hz, 3H) 1.68-1.77

(m, 1H) 1.95-2.06 (m, 1H) 2.20 (d, J=13.18 Hz, 1H) 2.29 (d, J=13.18 Hz, 1H) 3.68-3.79 (m, 2H) 3.81 (s, 3H) 4.03 (dd, J=12.45, 2.93 Hz, 2H) 6.39 (s, 1H) 7.26 (d, J=8.05 Hz, 2H) 7.37-7.53 (m, 3H) 7.65-7.75 (m, 1H); ES-HRMS m/z 426.1515 (M+H calc.: 426.1451).

Step 3: Preparation of (2S,4R)-4-(2,4-difluoro-3-(4-(1-methyl-1H-pyrazol-5-yl)phenylthio)phenyl)-2-methyl-tetrahydro-2H-pyran-4-carboxamide (2S,4R)-4-(2,4-difluoro-3-(4-(1-methyl-1H-pyrazol-5-yl)phenylthio)phenyl)-2-methyl-tetrahydro-2H-pyran-4-carbonitrile (100 mg, 0.23 mmol, 1 eq) was dissolved in 3 mL of a trifluoroacetic and sulfuric acid mixture (4:1). The reaction mixture stirred for 72 h at room temperature. The solution was poured into water (5 mL) and extracted with ethyl acetate (2×10 ml). The organic phase was washed with a saturated solution of sodium bicarbonate (1×10 mL) and concentrated to a solid. The crude solid was purified by reverse phase chromatography (40-90% acetonitrile-water) to afford the title product (37 mg, 36%) as a solid. 1H NMR (400 MHz, DMSO-d6) δ ppm 1.08 (d, J=5.86 Hz, 3H) 1.37-1.46 (m, 1H) 1.71-1.83 (m, 1H) 2.39 (dd, J=32.21, 13.91 Hz, 2H) 3.57-3.73 (m, 2H) 3.78 (d, J=3.66 Hz, 1H) 3.81 (s, 3H) 6.38 (s, 1H) 7.11 (d, J=8.79 Hz, 2H) 7.18 (d, J=8.05 Hz, 2H) 7.32 (t, J=8.05 Hz, 1H) 7.42-7.49 (m, 3H) 7.58-7.68 (m, 1H); ES-HRMS m/z 444.1592 (M+H calc.: 444.1557).

Example 29

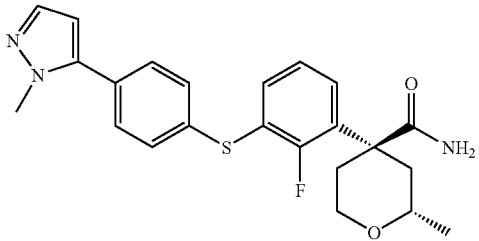

(2S,4R)-4-(2-fluoro-3-(4-(1-methyl-1H-pyrazol-5-yl)phenylthio)phenyl)-2-methyl-tetrahydro-2H-pyran-4-carboxamide Step 1: Preparation of (2S,4R)-4-(3-bromo-2-fluorophenyl)-2-methyl-tetrahydro-2H-Pyran-4-carbonitrile 2-(3-bromo-2-fluorophenyl)acetonitrile (800 mg, 3.7 mmol, 1 eq.) and (S)-1-iodo-2-(2-iodoethoxy)propane (1.27 g, 3.74 mmol, 1 eq.) were dissolved in dimethyl sulfoxide (10 mL). Sodium hydride (331 mg, 8.3 mmol, 2.2 eq.) was added to the reaction mixture and stirred for 1 h at room temperature. The reaction mixture was diluted with water (10 mL) and ethyl acetate (10 mL), and the layers were separated. The organic phase was washed with 1 M HCl (1×10 mL), water (1×10 mL) and brine (1×10 mL). The organic phase was concentrated under vacuum to afford a diastereomeric mixture of (2S,4R)-4-(3-bromo-2-fluorophenyl)-2-methyl-tetrahydro-2H-pyran-4-carbonitrile and (2S,4S)-4-(3-bromo-2-fluorophenyl)-2-methyl-tetrahydro-2H-pyran-4-carbonitrile (1:1). The diastereomeric mixture was separated by reverse phase chromatography (40-90% acetonitrile-water) to obtain the title compound (252 mg, 23%) as a single isomer. Stereochemistry confirmed by NMR. (2S,4R): 1H NMR (400 MHz, CHLOROFORM-d) δ ppm 1.26 (d, J=6.2 Hz, 3H) 1.81 (dd, J=13.2, 11.0 Hz, 1H) 2.08-2.26 (m, 3H) 3.89-4.02 (m, 2H) 4.04-4.16 (m, 1H) 6.99-7.13 (m, 1H) 7.32-7.44 (m, 1H) (s, 1H) 7.51-7.63 (m, 1H); LC/MS (M+H)=298 (100%), 300 (98.5%). (2S,4S): 1H NMR (400 MHz, CHLOROFORM-d) δ ppm 1.22 (d, J=6.2 Hz, 3H) 2.05 (dd, J=14.5, 10.7 Hz, 1H) 2.25-2.44 (m, 1H) 2.49-2.63 (m, 2H) 3.44-3.59 (m, 2H) 3.86-3.99 (m, 1H) 7.02-7.13 (m, 1H) 7.19-7.31 (m, 1H) (s, 1H) 7.53-7.64 (m, 1H); LC/MS (M+H)=298 (100%), 300 (98.5%).

Step 2: Preparation of (2S,4R)-4-(2-fluoro-3-(4-(1-methyl-1H-pyrazol-5-yl)phenylthio)phenyl)-2-methyl-tetrahydro-2H-Pyran-4-carbonitrile

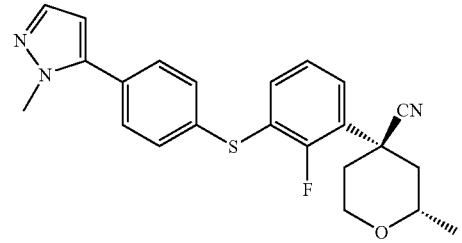

Alternative 1

4-(1-methyl-1H-pyrazol-5-yl)phenyl ethanethioate (156 mg, 0.67 mmol, 1 eq.), (2S,4R)-4-(3-bromo-2-fluorophenyl)-2-methyl-tetrahydro-2H-pyran-4-carbonitrile (200 mg, 0.67 mmol, 1 eq.), palladium tetrakis (42.8 mg, 0.07 mmol, 0.05 eq.) and DPEphos (19.9 mg, 0.07 mmol, 0.05 eq.), potassium tert-butoxide (2.01 mL of 1 M in THF, 2.01 mmol, 3 eq.) were mixed in isopropanol (5 mL) at room temperature. Nitrogen was bubbled through the reaction mixture for 5 minutes. The solution was heated to 65° C. for 24 hours. The solution was cooled to room temperature and diluted with ethyl acetate (5 mL) and water (5 mL). The layers were separated, and the aqueous phase was extracted with ethyl acetate (2×5 mL). The combined organic phases were dried over sodium sulfate, and the solvent was removed at reduced pressure. The resulting oil was isolated by reverse phase chromatography (40-90% acetonitrile-water) to give the desired product (220 mg, 80%). 1H NMR (400 MHz, DMSO-d6) δ ppm 1.18 (d, J=5.86 Hz, 3H) 1.66-1.77 (m, 1H) 1.95-2.06 (m, 1H) 2.22 (dd, J=35.87, 13.18 Hz, 2H) 3.68-3.80 (m, 2H) 3.83 (s, 3H) 4.02 (dd, J=12.44, 2.93 Hz, 1H) 6.41 (s, 1H) 7.27-7.58 (m, 8H); ES-HRMS m/z 408.1634 (M+H calc.: 408.1516).

Alternative 2

(2S,4R)-4-(3-bromo-2-fluorophenyl)-2-methyl-tetrahydro-2H-pyran-4-carbonitrile (80 g, 268 mmol), 4-(1-methyl-1H-pyrazol-5-yl)phenyl ethanethioate (62 g, 268 mmol), tetrakis(triphenylphosphine)palladium (17 g, 15 mmol), bis(2-diphenylphosphinophenyl)ether (8 g, 15 mmol) and tetrabutylammonium bromide (4 g, 13 mmol) were mixed together in toluene (800 mL) under a nitrogen atmosphere. 2.5 M sodium hydroxide (365 mL, 912 mmol) was added to the mixture and the mixture was heated to reflux. The reaction was usually done within three hours. The mixture was cooled to 25° C. and the phases were separated. The organic phase was dried with anhydrous magnesium sulfate and the solvent was stripped at reduced pressure. The crude product was purified by normal phase chromatography. The product (89 g) was obtained as an amorphous, hard glassy material.

Step 3: Preparation of (2S,4R)-4-(2-fluoro-3-(4-(1-methyl-1H-pyrazol-5-yl)phenylthio)phenyl)-2-methyl-tetrahydro-2H-pyran-4-carboxamide (2S,4R)-4-(2-fluoro-3-(4-(1-methyl-1H-pyrazol-5-yl)phenylthio)phenyl)-2-methyl-tetrahydro-2H-pyran-4-carbonitrile (200 mg, 0.49 mmol, 1 eq.) and potassium hydroxide (428 mg, 7.6 mmol, 15 eq.) were dissolved in tert-butyl alcohol (5.0 mL). The mixture was stirred at 60° C. for 24 h. The mixture was diluted with water (10 mL) and extracted with ethyl acetate (2×10 mL). The organic phase was concentrated to a solid. The crude solid was purified by reverse phase chromatography (40-90% acetonitrile-water) to afford the title product (100 mg, 48%) as a solid. 1H NMR (400 MHz, CHLOROFORM-d) δ ppm 1.22 (d, J=6.18 Hz, 3H) 1.61 (dd, J=13.43, 11.28 Hz, 1H) 1.94-2.03 (m, 2H) 2.37-2.51 (m, 2H) 3.89 (s, 3H) 3.91-3.98 (m, 2H) 5.38 (br. s., 2H) 6.31 (d, J=2.15 Hz, 1H) 7.13 (t, J=7.92 Hz, 1H) 7.21-7.24 (m, 1H) 7.33-7.39 (m, 5H) 7.52 (d, J=1.88 Hz, 1H); ES-HRMS m/z 426.1645 (M+H calc.: 426.1651).

Procedure for Enhancement of Chiral Purity of Final Compounds

Separations performed with a Berger MultiGram II SFC chromatograph using a Chiralpak AS-H 30×250 mm column from Chiral Technologies, Inc. Isocratic elution using 30% MeOH/70% $CO_2$ at 70 ml/min. Samples were injected in MeOH @ 3 mg/ml, 5 ml/injection. In the case of (2S,4R)-4-(2-fluoro-3-(4-(1-methyl-1H-pyrazol-5-yl)phenylthio)phenyl)-2-methyl-tetrahydro-2H-pyran-4-carbonitrile, obtained two peaks, peak 1, the minor enantiomer and peak 2, the major enantiomer. Analytical analysis was performed with a Chiralpak AS-H 4.6×250 mm column, 20% MeOH/80% $CO_2$; Peak 1 eluted at RT=4.446 minutes and peak 2 eluted at RT=6.345 minutes.

Example 29bis

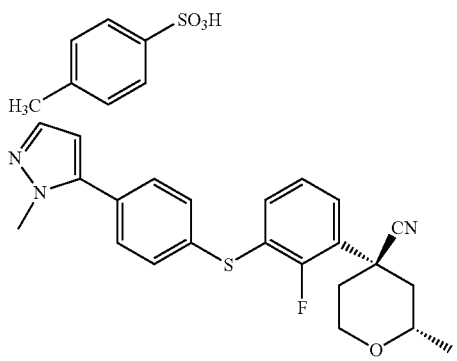

(2S,4R)-4-(2-fluoro-3-(4-(1-methyl-1H-pyrazol-5-yl)phenylthio)phenyl)-2-methyl-tetrahydro-2H-pyran-4-carbonitrile, tosylate salt, 1:1 molar ratio (2S,4R)-4-(2-fluoro-3-(4-(1-methyl-1H-pyrazol-5-yl)phenylthio)phenyl)-2-methyl-tetrahydro-2H-pyran-4-carbonitrile—i.e. the compound prepared in step 2 of Example 29—(4.5 g, 11.0 mmol) and para-toluenesulfonic acid (2.3 g, 12.1 mmol) were mixed together in ethyl acetate (68 mL). The mixture was heated to reflux and held until homogeneous. The mixture was cooled to 65° C. and held until crystallization started. The mixture was cooled to 60° C. and held for 30 minutes. The mixture was cooled to 25° C. and held for 60 minutes. The mixture was filtered and the solid was washed with ethyl acetate. A white solid (5.81 g, 90%) was obtained.

TGA/SDTA Analysis

Figure 2:
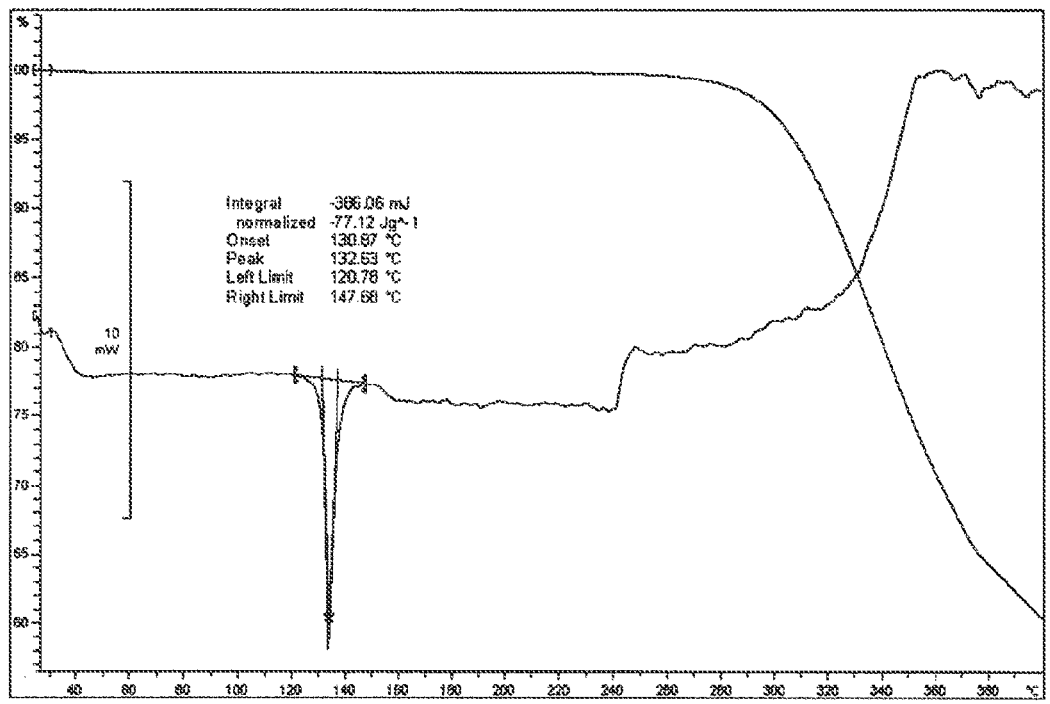
FIG. 2: TGA/SDTA trace for the same compound of FIG. 1. The melting point endotherm has a peak at 132.7° C. (onset at 130.9° C.).

A Mettler TGA/SDTA851e thermogravimetric analyzer simultaneous differential thermal analyzer was used to collect the weight loss and sample temperature versus temperature data. Samples were sealed in 40 μL pierceable aluminium capsules. Samples were heated at 5° C./min from 20° C. up to a maximum of 400° C. The temperature and simulated heat flow axis were calibrated using indium. The TGA/SDTA trace is shown in FIG. 2.

Powder X-Ray Diffraction Method

The powder X-ray diffraction pattern was measured using a Bruker D-8 Advance diffractometer. The system used a copper X-ray source maintained at 40 kV and 40 mA to provide Cu $K\alpha_1$ (1.5406 Å) and Cu $K\alpha_2$ (1.54439 Å) radiation with an intensity weighted average of ($K\alpha_{ave}$) 1.54184 Å. A scintillation counter was used for detection. Data were collected using a step scan of 0.02° per point with a 1 second/point counting time over a range of 3 to 35° two-theta. Fabricated aluminium inserts held in Bruker plastic sample cup holders were utilized for all analyses. Samples were run as is and were rotated during analysis to minimize preferred orientation. The measured pattern is shown below (peak positions derived from PXRD pattern of FIG. 1; 2 theta angles±0.1. degrees):

| Angle 2 theta | Intensity % |
| --- | --- |
| 5.6 | 10 |
| 7.8 | 5.3 |
| 8.5 | 15.2 |
| 10.5 | 13.1 |
| 11.4 | 8.8 |
| 12.6 | 9.2 |
| 13.2 | 13.4 |
| 13.5 | 28 |
| 14.3 | 56.2 |
| 15.0 | 10.5 |
| 15.5 | 14.5 |
| 15.8 | 6.1 |
| 16.5 | 10.4 |
| 17.1 | 13 |
| 17.7 | 8.8 |
| 18.9 | 100 |
| 19.3 | 10.6 |
| 19.6 | 6.5 |
| 20.1 | 12.1 |
| 21.4 | 24.1 |
| 21.7 | 15.5 |
| 22.0 | 8.9 |
| 22.8 | 15.4 |
| 23.3 | 33.1 |
| 23.7 | 12 |
| 24.2 | 14.1 |
| 24.5 | 37 |
| 25.3 | 10.6 |
| 25.9 | 6.7 |
| 26.3 | 15.1 |
| 26.6 | 17 |
| 27.1 | 8 |
| 27.4 | 5.7 |
| 28.3 | 5.1 |
| 28.8 | 14.2 |
| 29.2 | 8.7 |
| 30.5 | 6.1 |
| 31.4 | 7.1 |

-continued

| Angle 2 theta | Intensity % |
|---|---|
| 31.9 | 5.1 |
| 32.1 | 6.2 |
| 32.6 | 4.3 |
| 33.4 | 6.6 |
| 34.2 | 4 |
| 34.6 | 6.1 |

Example 30

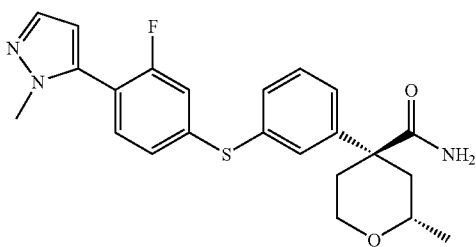

(2S,4R)-4-(3-(3-fluoro-4-(1-methyl-1H-pyrazol-5-yl)
phenylthio)phenyl)-2-methyl-tetrahydro-2H-pyran-4-
carboxamide Step 1: Preparation of S-3-fluoro-4-(1-methyl-1H-
pyrazol-5-yl)phenyl ethanethioate S-3-fluoro-4-(1-methyl-1H-pyrazol-5-yl)phenyl ethanethioate (2.00 g, 7.8 mmol, 1 eq), sodium tert-butoxide (753 mg, 7.8 mmol, 1 eq), palladium acetate (35.2 mg, 0.157 mmol) and (1,1'-Bis(Diphenylphosphine)ferrocene-dichloropalladium (115 mg, 0.157 mmol) were dissolved in 1,4 dioxane (20 mL). The mixture was stirred at room temperature for 1 h. Triisopropylsilane thiol (1.49 g, 7.80 mmol) was added. The resulting mixture was heated to reflux for 1 h, then it was poured into ethyl acetate (30 mL). The organics were washed with water (1×20 mL) and Brine (1×30 mL) then dried over sodium sulfate. The organics were evaporated to obtain a crude oil. The oil was dissolved in 16 mL of a solution of tetrabutyl ammonium fluoride in THF (1M) and stirred at room temperature for 10 min. Acetic anhydride (7.42 mL) was added to the reaction mixture and stirred for 20 min. The reaction mixture was poured into water (25 mL) and extracted with dichloromethane (2×20 mL). The organic phase was washed with Brine (1×20 mL), dried over sodium sulfate and concentrated. The resulting oil was purified by chromatography (Heptane/Ethyl acetate) (0-100%) to afford an amber oil. No further purification was made. LCMS (M+1)=251.

Step 2: Preparation of (2S,4R)-4-(3-(3-fluoro-4-(1-
methyl-1H-pyrazol-5-yl)phenylthio)phenyl)-2-me-
thyl-tetrahydro-2H-pyran-4-carbonitrile S-3-fluoro-4-(1-methyl-1H-pyrazol-5-yl)phenyl ethanethioate (692 mg, 2.76 mmol, 1.1 eq), (2S,4R)-4-(3-bromophenyl)-2-methyl-tetrahydro-2H-pyran-4-carbonitrile (700 mg, 2.50 mmol, 1 eq), palladium tetrakis(triphenyl phosphine) (150 mg, 0.130 mmol, 0.05 eq) and DPEphos (70.0 mg, 0.130 mmol, 0.05 eq), potassium tert-butoxide (7.50 ml of 1 M in THF, 7.49 mmol, 3 eq) were mixed in isopropanol (10 ml) at room temperature. Nitrogen was bubbled through the reaction mixture for 5 minutes. The solution was heated to 65° C. for 24 hours. The solution was cooled to room temp and diluted with ethyl acetate (5 ml) and water (5 ml). The layers separated and the aqueous phase was extracted with ethyl acetate (2×5 ml). The combined organic phases were dried over sodium sulfate and solvent removed at reduced pressure. The resulting oil was isolated by reverse phase chromatography (40-90% acetonitrile-water) to give the desired product (620 mg, 61%). 1H NMR (400 MHz, DMSO-d6) d ppm 1.17 (d, J=5.86 Hz, 3H) 1.66-1.74 (m, 1H) 1.94-2.03 (m, 1H) 2.07-2.14 (m, 1H) 2.20 (d, J=13.18 Hz, 1H) 2.47-2.50 (m, 2H) 3.72 (s, 3H) 4.03 (dd, J=12.45, 2.93 Hz, 1H) 6.38 (s, 1H) 7.15 (d, J=8.05 Hz, 1H) 7.25 (d, J=10.25 Hz, 1H) 7.44-7.51 (m, 3H) 7.55 (t, J=7.69 Hz, 1H) 7.59-7.63 (m, 1H) 7.65-7.68 (m, 1H). ES-HRMS m/z 408.1584 (M+H calcd: 408.1546).

Step 3: Preparation of (2S,4R)-4-(3-(3-fluoro-4-(1-
methyl-1H-pyrazol-5-yl)phenylthio)phenyl)-2-me-
thyl-tetrahydro-2H-pyran-4-carboxamide (2S,4R)-4-(3-(3-fluoro-4-(1-methyl-1H-pyrazol-5-yl) phenylthio)phenyl)-2-methyl-tetrahydro-2H-pyran-4-carbonitrile (380 mg, 0.93 mmol, 1 eq) and potassium hydroxide (812 mg, 14.5 mmol 15.5 eq) dissolved in tert-butyl alcohol (5.0 ml). The mixture stirred at 60° C. for 24 h. The mixture was diluted with water (10 ml) and extracted with ethyl acetate (2×10 ml). The organic phase was concentrated to a solid. The crude solid was purified by reverse phase chromatography (40-90% acetonitrile-water) to afford the title product (210 mg, 53%) as a solid. 1H NMR (400 MHz, DMSO-d6) d ppm 1.10 (d, J=5.86 Hz, 3H) 1.23-1.33 (m, 1H) 1.59 (td, J=12.81, 4.39 Hz, 2H) 2.58 (d, J=13.18 Hz, 1H) 3.39-3.51 (m, 2H) 3.71 (s, 3H) 3.84 (dd, J=11.71, 2.93 Hz, 1H) 6.37 (s, 1H) 7.04-7.17 (m, 3H) 7.30-7.54 (m, 7H). ES-HRMS m/z 426.1589 (M+H calcd: 408.1651).

Example 31

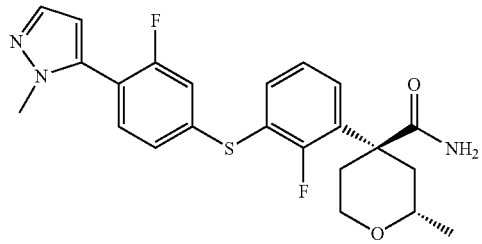

(2S,4R)-4-(2-fluoro-3-(3-fluoro-4-(1-methyl-1H-
pyrazol-5-yl)phenylthio)phenyl)-2-methyl-tetrahy-
dro-2H-pyran-4-carboxamide Step 1: Preparation of (2S,4R)-4-(2-fluoro-3-(3-
fluoro-4-(1-methyl-1H-pyrazol-5-yl)phenylthio)phe-
nyl)-2-methyl-tetrahydro-2H-pyran-4-carbonitrile S-3-fluoro-4-(1-methyl-1H-pyrazol-5-yl)phenyl ethanethioate (539 mg, 2.15 mmol, 1.1 eq), (2S,4R)-4-(3-bromo-2-fluorophenyl)-2-methyl-tetrahydro-2H-pyran-4-carbonitrile (580 mg, 1.94 mmol, 1 eq), palladium tetrakis(triphenyl phosphine) (117 mg, 0.101 mmol, 0.05 eq) and DPEphos (54.4 mg, 0.101 mmol, 0.05 eq), potassium tert-butoxide (5.84 ml of 1 M in THF, 5.84 mmol, 3 eq) were mixed in isopropanol (10 ml) at room temperature. Nitrogen was bubbled through the reaction mixture for 5 minutes. The solution was heated to 65° C. for 24 hours. The solution was cooled to room temp and diluted with ethyl acetate (5 ml) and water (5 ml). The layers separated and the aqueous phase was extracted with ethyl acetate (2×5 ml). The combined organic phases were dried over sodium sulfate and solvent removed at reduced pressure. The resulting oil was isolated by reverse phase chromatography (40-90% acetonitrile-water) to give the desired product (274 mg, 33%). 1H NMR (400 MHz, DMSO-d6) d ppm 1.19 (d, J=5.86 Hz, 3H) 1.68-1.77 (m, 1H) 2.02 (td, J=12.81, 4.39 Hz, 1H) 2.20 (d, J=13.91 Hz, 1H) 2.29 (d, J=13.18 Hz, 1H) 3.69-3.81 (m, 5H) 4.03 (dd, J=12.45, 2.93 Hz, 1H) 6.39 (s, 1H) 7.15 (d, J=8.05 Hz, 1H) 7.29 (d, J=10.25 Hz, 1H) 7.38 (t, J=8.05 Hz, 1H) 7.46-7.52 (m, 2H) 7.57 (q, J=7.57 Hz, 2H). ES-HRMS m/z 426.1445 (M+H calcd: 426.1451).

Step 2: Preparation of (2S,4R)-4-(2-fluoro-3-(3-fluoro-4-(1-methyl-1H-pyrazol-5-yl)phenylthio)phenyl)-2-methyl-tetrahydro-2H-pyran-4-carboxamide (2S,4R)-4-(2-fluoro-3-(3-fluoro-4-(1-methyl-1H-pyrazol-5-yl)phenylthio)phenyl)-2-methyl-tetrahydro-2H-pyran-4-carbonitrile (160 mg, 0.376 mmol, 1 eq) and potassium hydroxide (812 mg, 14.5 mmol 15.5 eq) dissolved in tert-butyl alcohol (5.0 ml). The mixture stirred at 60° C. for 24 h. The mixture was diluted with water (10 ml) and extracted with ethyl acetate (2×10 ml). The organic phase was concentrated to a solid. The crude solid was purified by reverse phase chromatography (40-90% acetonitrile-water) to afford the title product (115, 69%) as a solid. 1H NMR (400 MHz, DMSO-d6) d ppm 1.08 (d, J=5.86 Hz, 3H) 1.37-1.45 (m, 1H) 1.77 (td, J=13.00, 4.76 Hz, 1H) 2.36 (d, J=13.18 Hz, 1H) 2.44 (d, J=13.18 Hz, 1H) 3.57-3.70 (m, 2H) 3.71 (s, 3H) 3.79 (dd, J=11.71, 2.93 Hz, 1H) 6.38 (s, 1H) 7.04-7.17 (m, 4H) 7.30 (t, J=8.05 Hz, 1H) 7.41-7.48 (m, 2H) 7.49-7.51 (m, 1H) 7.54 (t, J=7.32 Hz, 1H). ES-HRMS m/z 444.1521 (M+H calcd: 444.1557).

Example 32

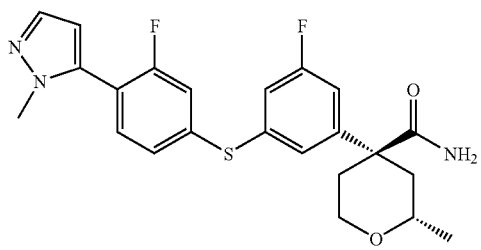

(2S,4R)-4-(3-fluoro-5-(3-fluoro-4-(1-methyl-1H-pyrazol-5-yl)phenylthio)phenyl)-2-methyl-tetrahydro-2H-pyran-4-carboxamide Step 1: Preparation Of (2S,4R)-4-(3-fluoro-5-(3-fluoro-4-(1-methyl-1H-pyrazol-5-yl)phenylthio)phenyl)-2-methyl-tetrahydro-2H-pyran-4-carbonitrile S-3-fluoro-4-(1-methyl-1H-pyrazol-5-yl)phenyl ethanethioate (349 mg, 1.39 mmol, 1.1 eq), (2S,4R)-4-(3-bromo-2-fluorophenyl)-2-methyl-tetrahydro-2H-pyran-4-carbonitrile (375 mg, 1.26 mmol, 1 eq), palladium tetrakis(triphenyl phosphine) (75 mg, 0.065 mmol, 0.05 eq) and DPEphos (35 mg, 0.065 mmol, 0.05 eq), potassium tert-butoxide (3.77 ml of 1 M in THF, 3 eq) were mixed in isopropanol (10 ml) at room temperature. Nitrogen was bubbled through the reaction mixture for 5 minutes. The solution was heated to 65° C. for 24 hours. The solution was cooled to room temp and diluted with ethyl acetate (5 ml) and water (5 ml). The layers separated and the aqueous phase was extracted with ethyl acetate (2×5 ml). The combined organic phases were dried over sodium sulfate and solvent removed at reduced pressure. The resulting oil was isolated by reverse phase chromatography (40-90% acetonitrile-water) to give the desired product (300 mg, 56%). 1H NMR (400 MHz, DMSO-d6) d ppm 1.17 (d, J=5.86 Hz, 3H) 1.66-1.74 (m, 1H) 1.98 (td, J=13.00, 4.76 Hz, 1H) 2.08-2.14 (m, 1H) 2.21 (d, J=13.91 Hz, 1H) 3.62-3.71 (m, 2H) 3.73 (s, 3H) 4.02 (dd, J=12.45, 2.93 Hz, 1H) 6.41 (s, 1H) 7.25-7.33 (m, 2H) 7.39-7.47 (m, 3H) 7.50-7.56 (m, 2H). ES-HRMS m/z 426.1565 (M+H calcd: 426.1451).

Step 2: Preparation of (2S,4R)-4-(3-fluoro-5-(3-fluoro-4-(1-methyl-1H-pyrazol-5-yl)phenylthio)phenyl)-2-methyl-tetrahydro-2H-pyran-4-carboxamide (2S,4R)-4-(3-fluoro-5-(3-fluoro-4-(1-methyl-1H-pyrazol-5-yl)phenylthio)phenyl)-2-methyl-tetrahydro-2H-pyran-4-carbonitrile (169 mg, 0.397 mmol, 1 eq) was dissolved in dimethyl sulfoxide (6.0 mL). Sodium hydroxide (0.476 mL, 2.5 N) was added to the reaction mixture followed by hydrogen peroxide (0.476, 35%). The mixture stirred at room temperature for 10 min. The mixture was diluted with ethyl acetate (10 ml) and washed with water (1×10 mL) Brine (1×10 mL). The organic phase was dried over sodium sulfate and concentrated to a solid. The crude solid was purified by reverse phase chromatography (40-90% acetonitrile-water) to afford the title product (117, 66%) as a solid. 1H NMR (400 MHz, DMSO-d6) d ppm 1.10 (d, J=5.86 Hz, 3H) 1.23-1.32 (m, 1H) 1.58 (td, J=12.81, 4.39 Hz, 1H) 2.46 (br. s., 1H) 2.57 (br. s., 1H) 3.41-3.50 (m, 2H) 3.73 (s, 3H) 3.84 (dd, J=11.71, 2.93 Hz, 1H) 6.40 (s, 1H) 7.15-7.23 (m, 4H) 7.27-7.32 (m, 2H) 7.37 (s, 1H) 7.47-7.53 (m, 2H). ES-HRMS m/z 444.1606 (M+H calcd: 444.1557).

Example 33

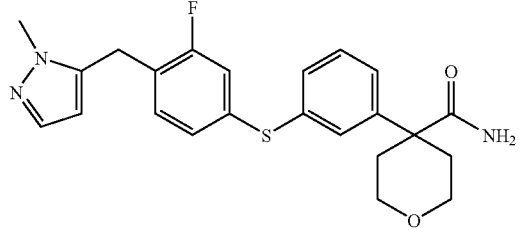

4-{3-[3-Fluoro-4-(2-methyl-2H-pyrazol-3-ylmethyl)phenylsulfanyl]-phenyl}-tetrahydro-pyran-4-carboxylic acid amide Step 1: Preparation of 5-(4-Bromo-2-fluoro-benzyl)-methyl pyrazole 1-methyl-1H-pyrazol-5-ylboronic acid (224 mg, 1.78 mmol, 1 eq.), 4-bromo-1-(bromomethyl)-2-fluorobenzene (500 mg, 1.87 mmol, 1.05 eq.), Pd(PPh₃)₄ (0.05 eq.) and 2N aq. Sodium carbonate solution (2.4 eq) were taken up in toluene:ethanol (4:3) and purged with nitrogen. The reaction mixture was heated at 50° C. for 2-20 h. The reaction mixture was concentrated. The residue was extracted with ether, dried over sodium sulfate, filtered, and concentrated. The crude material was purified by flash chromatography eluting with gradient of 0-100% dichloromethane in hexanes to obtain 0.60 g of the intermediate as a crude oil. APCI(+)=269, 271

Step 2: Preparation of 4-{3-[3-Fluoro-4-(2-methyl-2H-pyrazol-3-ylmethyl) phenylsulfanyl]-phenyl}-tetrahydro-pyran-4-carboxylic acid amide To a solution of 4-(3-(triisopropylsilylthio)phenyl)-tetrahydro-2H-pyran-4-carboxamide (630 mg, 1.60 mmol, 1.0 eq) in anhydrous isopropanol was added 5-(4-Bromo-2-fluoro-benzyl)-1-methylpyrazole (430 mg, 1.60 mmol, 1.0 eq), tetraethylammonium chloride (1 eq), cesium fluoride (1.0 eq), DPEPhos (0.066 eq), and Pd(PPh₃)₄ (0.22 eq). This mixture was degassed and filled with nitrogen. Potassium tert-butoxide solution (1M in THF, 2 eq) was then added and the resulting reaction mixture was heated at 70° C. with stirring for 15 h. The solvent was removed under reduced pressure. The residue was slurried with silica gel and purified by flash chromatography using 1-5% methanol I chloroform as eluent to isolate 17 mg (4%) of the title product as a white solid. as a white solid. 1H NMR (DMSO-D6, 300 MHz) d ppm: 7.43-7.36 (m, 3H), 7.42-7.24 (m, 6H), 7.28-7.17 (m, 4H), 7.10-7.04 (m, 3H), 5.90 (d, J=1.7 Hz, 1H), 4.01 (s. 2H), 3.75 (s, 3H), 3.71 (dm, J=11.6 Hz, 2H), 3.41 (bt, J=10.2 Hz, 2H), 2.5)s. 3H), 2.39 (bd, J=13.8 Hz, 2H), 1.77 (m, 2H). APCI(+) m/z=426 amu.

Example 34

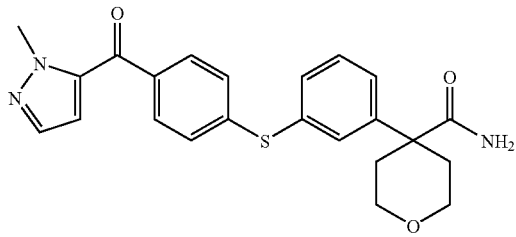

4-[3-({4-[(1-methyl-1H-pyrazol-5-yl)carbonyl]phenyl}thio)phenyl]tetrahydro-2H-pyran-4-carboxamide Step 1: Preparation of (4-fluorophenyl)(1-methyl-1H-5-yl)methanol 1-methyl-1H-pyrazole (1.32 g, 16.1 mmol) was dissolved in anhydrous THF (50 ml). The solution was cooled to −78 degrees Celsius and a 1.6 M solution of nBuLi (1.2 equiv) was added via syringe. The solution was allowed to stir at −78 degrees Celsius for 5 minutes before the 4-fluorobenzaldehyde (2.0 g, 16.1 mmol) was added. The ice bath was then removed and the mixture was allowed to equilibrate to room temperature where it was allowed to stir for 1 hour. The reaction was then quenched by the addition of 1 N ammonium chloride (25 ml). The reaction was diluted with ethyl acetate (50 ml) and water (25 ml). The layers were mixed and the organic phase was collected and washed again with water. The organic layer was dried (sodium sulfate) and concentrated to give (4-fluorophenyl)(1-methyl-1H-5-yl)methanol as a viscous oil. Yield=3.1 g, 93%.

Step 2: Preparation of (4-fluorophenyl)(1-methyl-1H-pyrazol-5-yl)methanone (4-fluorophenyl)(1-methyl-1H-5-yl)methanol (3.1 g, 15.1 mmol) was suspended in acetonitrile (20 ml). Pyridinium chlorochromate (6.4 g, 30.2 mmol)) was added and the reaction was heated at 50 degrees Celsius for 4 hours. Water (20 ml) was added to the reaction mixture causing a precipitate to form. The precipitate was collected using suction filtration. It was washed thoroughly with water and dried under vacuum to provide the product, (4-fluorophenyl)(1-methyl-1H-pyrazol-5-yl)methanone, as a beige colored solid. Yield=1.65 g, 53%. 1H NMR (400 MHz, CHLOROFORM-d) δ ppm 4.23 (s, 3H) 6.66 (s, 1H) 7.20 (t, J=8.45 Hz, 2H) 7.55 (s, 1H) 7.95 (dd, J=8.19, 5.63 Hz, 2H).

Step 3: Preparation of 4-[3-({4-[(1-methyl-1H-pyrazol-5-yl)carbonyl]phenyl}thio)phenyl]tetrahydro-2H-pyran-4-carboxamide (4-fluorophenyl-1-methyl-1H-pyrazol-5-yl)methanone (250 mg, 1.2 mmol) and 4-{3-[(triisopropylsilyl)thio]phenyl}tetrahydro-2H-pyran-4-carboxamide (482 mg, 1.2 mmol) were added to a 1:1 solution of toluene/THF (20 ml). The mixture was heated to 80 degrees Celsius and it became homogenous. Tetra n-butylammonium fluoride (1.5 equiv, as a 1 M solution in THF) was added and stirring was continued at 80 degrees Celsius for 12 hours. The reaction was allowed to cool to room temperature. A fine light brown precipitate formed over 5 hours. The precipitate, 4-[3-({4-[(1-methyl-1H-pyrazol-5-yl)carbonyl]phenyl}thio)phenyl]tetrahydro-2H-pyran-4-carboxamide, was collected by suction filtration and washed with water and ethyl ether. Yield=265 mg, 51%. 1H NMR (400 MHz, DMSO-d₆) δ ppm 1.75-1.87 (m, 2H) 2.42 (d, J=13.18 Hz, 2H) 3.48 (t, J=10.61 Hz, 2H) 3.74 (d, J=11.35 Hz, 2H) 4.07 (s, 3H) 6.75 (d, J=2.20 Hz, 1H) 7.03 (br. s., 1H) 7.24 (br. s., 1H) 7.30 (d, J=8.42 Hz, 2H) 7.41 (d, J=4.03 Hz, 1H) 7.48 (d, J=4.76 Hz, 2H) 7.55 (s, 1H) 7.57 (d, J=2.20 Hz, 1H) 7.80 (d, J=8.42 Hz, 2H). HRMS calc M+H: 422.1538, found 422.1651.

Example 35

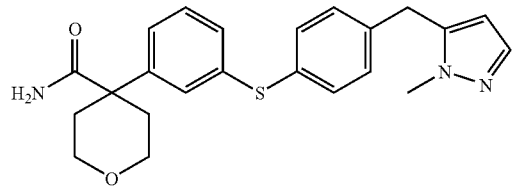

4-[3-({4-[(1-methyl-1H-pyrazol-5-yl)methyl]phenyl}thio)phenyl]tetrahydro-2H-pyran-4-carboxamide Step 1: Preparation of 5-(4-bromobenzyl)-1-methyl-1H-pyrazole 0.25 gm of 4-bromobenzyl bromide, 0.208 gm of 1-methyl-5-(4,4,5,5-tetramethyl-1,3,2-dioxaborolan-2-yl)-1H- pyrazole and 0.022 gm of palladium (0) tetrakis-(triphenylphosphine) were placed in a septum sealed vial and evacuated/nitrogen filled three times. 8 ml of 1,4-dioxane was then added, followed by the addition of 2 ml of 1M cesium carbonate. The mixture was stirred at room temperature for 30 minutes and heated at 70° C. for 4 hours. The reaction mixture was cooled, diluted with water and extracted with ethyl acetate. The ethyl acetate was dried with sodium sulfate, filtered, concentrated and the residue purified by reverse phase HPLC to give 0.13 g of product. LCMS (M+H): 252.

Step 2: Preparation of 4-[3-({4-[(1-methyl-1H-pyrazol-5-yl)methyl]phenyl}thio)-phenyl]tetrahydro-2H-pyran-4-carboxamide 0.59 gm of 4-(3-(triisopropylsilylthio)phenyl)tetrahydro-2H-pyran-4-carboxamide, 0.253 gm of tetraethylammonium chloride, 0.04 gm of oxydi-2,1-phenylene bis-(diphenylphosphine), 0.89 gm palladium(0)tetrakis-(triphenylphosphine), 0.377 gm 5-(4-bromobenzyl)-1-methyl-1H-pyrazole and 0.228 gm of cesium fluoride were placed in a reaction flask and evacuated and filled with nitrogen 3 times. 10 ml of nitrogen purged isopropanol was added, followed by the addition of 1.5 ml of 1.0M potassium t-butoxide in tetrahydrofuran. The mixture was then refluxed for 2 hours. After cooling, the reaction mixture was diluted with water and extracted with ethyl acetate. The ethyl acetate extract was dried with sodium sulfate, filtered, concentrated and purified by reverse phase chromatography to give 0.202 gm of product. HRMS (M+H) calc. 408.1746 obsd. 408.2033 1H NMR (400 MHz, DMSO-$d_6$) δ ppm 1.71-1.81 (m, 2H) 2.36 (d, J=13.54 Hz, 2H) 3.45 (t, J=10.80 Hz, 2H) 3.71 (br. s., 1H) 3.68 (s, 4H) 4.03 (s, 2
H) 5.98 (s, 1H) 6.98 (br. s., 1H) 7.11 (d, J=6.95 Hz, 1H) 7.21 (d, J=8.42 Hz, 3H) 7.26-7.36 (m, 2H) 7.30 (d, J=8.78 Hz, 4H).

Example 36

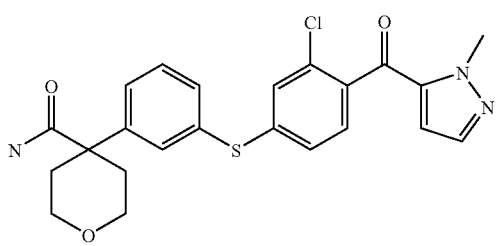

4-[3-({3-chloro-4-[(1-methyl-1H-pyrazol-6-yl)carbonyl]phenyl}thio)phenyl]tetrahydro-2H-pyran-4-carboxamide Step 1: Preparation of (2-chloro-4-fluorophenyl)(1-methyl-1H-Pyrazol-5-yl)methanol To a solution of N-methylpyrazole (1.0 g, 12.18 mmol) in anhydrous tetrahydrofuran (35 mL) chilled to −78° C., was added via syringe 1.6 M solution of n-butyllithium (9.1 mL). The reaction was stirred at −78° C. for 5 minutes before 2-chloro-4-fluorobenzaldehyde (1.93 g, 12.2 mmol) was added. The ice bath was then removed and the reaction was stirred for 18 h at room temperature. 1 M ammonium chloride (12 mL) was added and the reaction was diluted with ethyl acetate (50 mL). The layers were separated and the organic layer was washed with water (20 mL) and saturated sodium chloride (20 mL) before drying over anhydrous sodium sulfate. Filtration and evaporation of the solvent under reduced pressure afforded a crude yellow oil. Purification by normal phase chromatography provided the title compound as a clear oil (0.94 g).

LC/MS 5-100% acetonitrile/tfa-water/tfa (4 min gradient) 2.87 min [(M+H)$^+$=241].

$^1$H NMR (400 MHz, DMSO-$d_6$) δ ppm 7.72 (1H, dd, J=8.8, 6.4 Hz), 7.43 (1H, dd, J=8.9, 2.6 Hz), 7.27-7.38 (1H, m), 7.24 (1H, d, J=1.7 Hz), 6.30 (1H, d, J=5.5 Hz), 6.01 (1H, d, J=5.5 Hz), 5.59 (1H, d, J=1.7 Hz), 3.86 (3H, s)

Step 2: Preparation of (2-chloro-4-fluorophenyl)(1-methyl-1H-pyrazol-5-yl)methanone To a suspension of (2-chloro-4-fluorophenyl)(1-methyl-1H-pyrazol-5-yl)methanol (0.94 g, 3.91 mmol) in acetonitrile (5 mL) was added pyridinium chlorochromate (1.26 g, 5.86 mmol). The reaction was heated at 50° C. for 18 h. Water (13 mL) was added to the reaction mixture causing a precipitate to form. The precipitate was collected by suction filtration and washed thoroughly with water (100 mL). The precipitate was then washed with ethyl ether (100 mL) and the two filtrates were combined. The layers were separated and the organic layer was washed with water (50 mL) and saturated sodium chloride (50 mL) before drying over anhydrous sodium sulfate. Filtration and evaporation of the solvent under reduced pressure afforded the title compound as an off-white solid (0.86 g).

LC/MS 5-100% acetonitrile/tfa-water/tfa (4 min gradient) 3.47 min [(M+H)$^+$=239]. $^1$H NMR (400 MHz, DMSO-$d_6$) δ ppm 7.60-7.74 (2H, m), 7.56 (1H, d, J=2.0 Hz), 7.33-7.43 (1H, m), 6.53 (1H, d, J=2.0 Hz), 4.17 (3H, s)

Step 3: Preparation of 4-[3-({3-chloro-4-[(1-methyl-1H-pyrazol-5-yl)carbonyl]phenyl}thio)phenyl]tetrahydro-2H-pyran-4-carboxamide To a solution of (2-chloro-4-fluorophenyl)(1-methyl-1H-pyrazol-5-yl)methanone (500 mg, 2.10 mmol) and 4-{3-[(triisopropylsilyl)thio]phenyl}tetrahydro-2H-pyran-4-carboxamide (825 mg, 2.10 mmol) in dimethylformamide (14 mL) was added a 1.0 M solution of tetrabutylammonium fluoride in tetrahydrofuran (2.72 mL, 2.72 mmol) and the reaction was stirred at room temperature for 18 h. Water (50 mL) was added to the reaction mixture to precipitate the product. The precipitated product was collected by suction filtration and washed with water and ethyl ether. The precipitate was vacuum desiccated to afford the title compound as a yellow solid (0.82 g).

LC/MS 5-100% acetonitrile/tfa-water/tfa (4 min gradient) 3.53 min [(M+H)$^+$=456]. $^1$H NMR (400 MHz, DMSO-$d_6$) δ ppm 7.37-7.61 (6H, m), 7.31 (2H, s), 7.21 (1H, dd, J=8.0, 1.7 Hz), 7.10 (1H, s), 6.55 (1H, d, J=2.0 Hz), 4.15 (3H, s), 3.66-3.79 (2H, m), 3.47 (2H, t, J=10.6 Hz), 2.42 (2H, d, J=13.7 Hz), 1.73-1.89 (2H, m)

Example 37

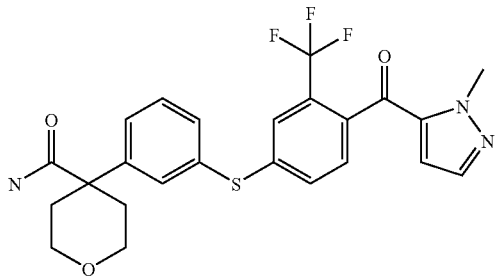

4-[3-({4-[(1-methyl-1H-pyrazol-5-yl)carbonyl]-3-(trifluoromethyl)phenyl}thio)phenyl]tetrahydro-2H-pyran-4-carboxamide Step 1: Preparation of (4-fluoro-2-(trifluoromethyl)phenyl)(1-methyl-1H-pyrazol-5-yl)methanol To a solution of N-methylpyrazole (1.0 g, 12.18 mmol) in anhydrous tetrahydrofuran (35 mL) chilled to −78° C., was added via syringe 1.6 M solution of n-butyllithium (9.1 mL). The reaction was stirred at −78° C. for 5 minutes before 4-fluoro-2-trifluoromethylbenzaldehyde (2.34 g, 12.2 mmol) was added. The ice bath was then removed, and the reaction was stirred for 18 h at room temperature. 1 M ammonium chloride (12 mL) was added and the reaction was diluted with ethyl acetate (50 mL). The layers were separated and the organic layer was washed with water (20 mL) and saturated sodium chloride (20 mL) before drying over anhydrous sodium sulfate. Filtration and evaporation of the solvent under reduced pressure afforded a crude yellow oil. Purification by normal phase chromatography provided the title compound as a yellow solid (1.39 g).

LC/MS 5-100% acetonitrile/tfa-water/tfa (4 min gradient) 3.11 min [(M+H)$^+$=275]. $^1$H NMR (400 MHz, DMSO-d$_6$) δ ppm 7.92 (1H, dd, J=8.6, 5.6 Hz), 7.57-7.72 (2H, m), 7.22 (1H, d, J=1.9 Hz), 6.42 (1H, d, J=5.6 Hz), 6.03 (1H, d, J=5.4 Hz), 5.49 (1H, d, J=1.9 Hz), 3.84 (3H, s)

Step 2: Preparation of (4-fluoro-2-(trifluoromethyl)phenyl)(1-methyl-1H-pyrazol-5-yl)methanone To a suspension of (4-fluoro-2-(trifluoromethyl)phenyl)(1-methyl-1H-pyrazol-5-yl)methanol (1.37 g, 5.0 mmol) in acetonitrile (10 mL) was added pyridinium chlorochromate (1.62 g, 7.49 mmol). The reaction was heated at 50° C. for 18 h. Water (13 mL) was added to the reaction mixture causing a precipitate to form. The precipitate was collected by suction filtration and washed thoroughly with water (100 mL). The precipitate was then washed with ethyl ether (100 mL) and the two filtrates were combined. The layers were separated and the organic layer was washed with water (50 mL) and saturated sodium chloride (50 mL) before drying over anhydrous sodium sulfate. Filtration and evaporation of the solvent under reduced pressure afforded the title compound as a yellow oil (1.23 g).

LC/MS 5-100% acetonitrile/tfa-water/tfa (4 min gradient) 3.54 min [(M+H)$^+$=273]. $^1$H NMR (400 MHz, DMSO-d$_6$) δ ppm 7.77-7.92 (2H, m), 7.65-7.75 (1H, m), 7.56 (1H, d, J=2.0 Hz), 6.51 (1H, d, J=2.0 Hz), 4.17 (3H, s)

Step 3: Preparation of 4-[3-({4-[(1-methyl-1H-pyrazol-5-yl)carbonyl]-3-(trifluoromethyl)phenyl}thio)phenyl]tetrahydro-2H-pyran-4-carboxamide To a solution of (4-fluoro-2-(trifluoromethyl)phenyl)(1-methyl-1H-pyrazol-5-yl)methanone (510 mg, 1.87 mmol) and 4-{3-[(triisopropylsilyl)thio]phenyl}tetrahydro-2H-pyran-4-carboxamide (885 mg, 2.25 mmol) in dimethylformamide (14 mL) was added a 1.0 M solution of tetrabutylammonium fluoride in tetrahydrofuran (2.44 mL, 2.44 mmol) and the reaction was stirred at room temperature for 18 h. Water (50 mL) was added to the reaction mixture to precipitate the product. The precipitated product was collected by suction filtration and washed with water and ethyl ether. The precipitate was vacuum desiccated to afford the title compound as a tan solid (0.83 g). LC/MS 5-100% acetonitrile/tfa-water/tfa (4 min gradient) 3.57 min [(M+H)$^+$=490]. $^1$H NMR (400 MHz, DMSO-d$_6$) 0 ppm 7.23-7.74 (9H, m), 7.09 (1H, s), 6.54 (1H, d, J=2.0 Hz), 4.16 (3H, s), 3.64-3.83 (2H, m), 3.47 (2H, t, J=10.5 Hz), 2.42 (2H, d, J=13.5 Hz), 1.68-1.92 (2H, m)

Example 38

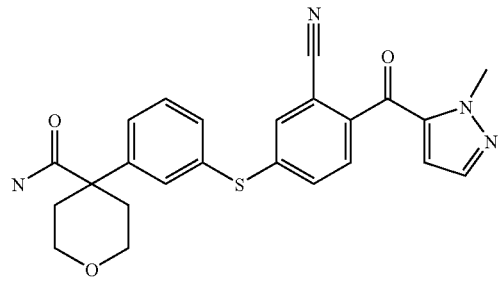

4-[3-({3-cyano-4-[(1-methyl-1H-pyrazol-5-yl)carbonyl]phenyl}thio)phenyl]tetrahydro-2H-pyran-4-carboxamide To a microwave vessel containing the compound of example 36, sodium cyanide (103 mg, 2.10 mmol), and nickel (II) bromide (230 mg, 1.05 mmol) was added 1-methyl-2-pyrrolidinone (5 mL). The reaction was placed in the microwave apparatus at 200° C., 120 W for 1 min. The reaction mix was partitioned between ethyl acetate (50 mL) and water (50 mL). The organic layer was washed with brine (50 mL), dried over magnesium sulfate, filtered, and evaporated to afford a crude solid. Purification by reverse phase chromatography provided the title compound as an off-white solid (6 mg).

LC/MS 5-100% acetonitrile/tfa-water/tfa (5 min gradient) 4.62 min [(M+H)$^+$=447]. $^1$H NMR (400 MHz, DMSO-d$_6$) δ ppm 7.70-7.89 (2H, m), 7.41-7.66 (6H, m), 7.31 (1H, br. s.), 7.10 (1H, br. s.), 6.74 (1H, d, J=2.0 Hz), 4.13 (3H, s), 3.73 (2H, d, J=11.7 Hz), 3.47 (2H, t, J=10.4 Hz), 2.42 (2H, d, J=13.7 Hz), 1.72-1.90 (2H, m)

Example 39

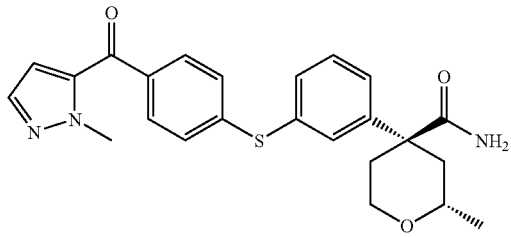

(2S,4R)-2-methyl-4-(3-(4-(1-methyl-1H-pyrazole-5-carbonyl)phenylthio)phenyl)-tetrahydro-2H-pyran-4-carboxamide The compound of example 55, below, (77 mg, 0.18 mmol) was dissolved in a 5 mL solution of 4:1 TFA:T2SO4. The mixture was heated to 60° C. for 2 h. The reaction was cooled, neutralized with 2.5N NaOH, extracted into ethyl acetate (5 mL), dried over magnesium sulfate, filtered, and concentrated to 173 mg oil. The product was isolated by reverse phase chiral chromatography and obtained as a light-yellow solid. 1H NMR (400 MHz, DMSO-$d_6$) δ ppm 7.79 (2H, m, J=8.4 Hz), 7.57 (1H, d, J=2.2 Hz), 7.53 (1H, s), 7.31-7.50 (4H, m), 7.27 (2H, m, J=8.4 Hz), 7.12 (1H, s), 6.75 (1H, d, J=2.2 Hz), 4.06 (3H, s), 3.81-3.88 (1H, m), 3.39-3.51 (2H, m), 2.55-2.61 (2H, m), 1.54-1.64 (1H, m), 1.24-1.33 (1H, m), 1.10 (3H, d, J=6.2 Hz).

Example 40

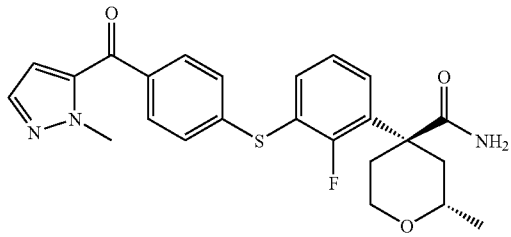

(2S,4R)-2-methyl-4-(3-(4-(1-methyl-1H-pyrazole-4-carbonyl)phenylthio)phenyl)-tetrahydro-2H-pyran-4-carboxamide (2S,4R)-4-(2-fluoro-3-(4-(1-methyl-1H-pyrazole-5-carbonyl)phenylthio)phenyl)-2-methyl-tetrahydro-2H-pyran-4-carbonitrile (150 mg, 0.36 mmol) was dissolved in a 5 mL solution of 4:1 TFA:$H_2SO_4$. The mixture was heated to 60° C. for 2 h. The reaction was cooled, neutralized with 2.5N NaOH, extracted into ethyl acetate (5 mL), dried over magnesium sulfate, filtered and concentrated to 173 mg oil. The product was isolated by reverse phase chiral chromatography and obtained as a light-yellow solid. 1H NMR (400 MHz, DMSO-d6) δ ppm 7.83 (2H, m, J=8.4 Hz), 7.59-7.65 (2H, m), 7.51-7.57 (1H, m), 7.36 (1H, t, J=7.9 Hz), 7.29 (2H, m, J=8.4 Hz), 7.09-7.18 (2H, m), 6.81 (1H, d, J=2.2 Hz), 4.11 (3H, s), 3.80-3.88 (1H, m), 3.63-3.78 (2H, m), 2.44 (2H, d, J=19.0 Hz), 1.78-1.87 (1H, m), 1.43-1.52 (1H, m), 1.13 (3H, d, J=6.2 Hz). HRMS calc M+H: 454.1601, found 454.1603.

Example 41

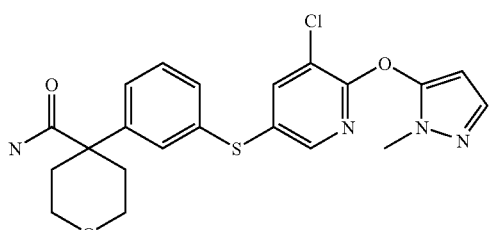

4-(3-(5-chloro-6-(1-methyl-1H-pyrazol-5-yloxy)pyridin-3-ylthio)phenyl)-tetrahydro-2H-pyran-4-carboxamide Step 1: Preparation of 1-methyl-1H-pyrazol-5-ol To a MeOH (6 mL) solution of methyl trans-3-methoxyacrylate (2.32 g, 20.0 mmol) was added methylhydrazine (0.92 g, 20.0 mmol). The reaction was stirred at 90° C. 18 h. The mixture was cooled and concentrated to a semi-solid that was used without further purification. 1H NMR (400 MHz, DMSO-d6) δ ppm 7.02 (d, J=1.76 Hz, 1H), 5.23 (d, J=1.95 Hz, 1H), 3.42 (s, 3H), 2.44 (dt, J=3.71, 1.86 Hz, 1H).

Step 2: Preparation of 4-(3-(5-chloro-6-(1-methyl-1H-pyrazol-5-yloxy)pyridin-3-ylthio)phenyl)-tetrahydro-2H-pyran-4-carboxamide A solution of 4-{3-[(5,6-dichloropyridin-3-yl)thio]phenyl}tetrahydro-2H-pyran-4-carboxamide (310 mg, 0.809 mmol) and 1-methyl-1H-pyrazol-5-ol (120 mg, 0.41 mmol) in 12 mL of NMP was treated with cesium carbonate (255 mg, 0.783 mmol) and stirred at 110° C. for 1 hour. The reaction was cooled and the product isolated by reverse phase chromatography to a light-yellow solid (21 mg, 18%). 1H NMR (400 MHz, DMSO-d6) δ ppm 8.14 (dd, J=8.42, 2.20 Hz, 1H), 7.29-7.41 (m, 3H), 7.25 (s, 1H), 7.16-7.21 (m, 1H), 7.06 (s, 1H), 6.09 (d, J=2.20 Hz, 1H), 3.70 (dt, J=11.81, 3.98 Hz, 2H), 3.60 (s, 3H), 3.40-3.48 (m, 2H), 2.31-2.43 (m, 2H), 1.70-1.81 (m, 2H). HRMS calc M+H: 445.1101, found 445.1106.

Example 42

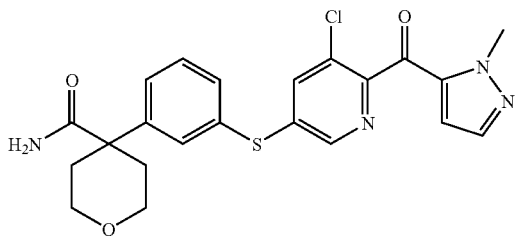

4-(3-(5-chloro-6-(1-methyl-1H-pyrazole-5-carbonyl)pyridin-3-ylthio)phenyl)-tetrahydro-2H-pyran-4-carboxamide Under a nitrogen atmosphere, sodium hydride (27.2 mg, 0.679 mmol) was added to a mixture of 4-{3-[(5,6-dichloropyridin-3-yl)thio]phenyl}tetrahydro-2H-pyran-4-carboxamide (200 mg, 0.522 mmol), 1-methyl-1H-pyrazole-5-carbaldehyde (57.5 mg, 0.522 mmol), and 1,3-dimethylimidazolium chloride (20.8 mg, 0.157 mmol) in anhydrous DMF (6 mL). The reaction was heated at 65° C. overnight. The reaction mixture was poured into ice water, and the pH was adjusted with acetic acid. The product was extracted with ethyl acetate, and the organic layer was washed with water and saturated sodium sulfate before drying over anhydrous sodium sulfate. Filtration and evaporation of the solvent under reduced a solid that was purified by reverse phase chromatography to provide the desired product (4.4 mg). $^1$H NMR (400 MHz, DMSO-d6) d ppm 1.63-1.93 (m, 2H) 2.29-2.47 (m, 2H) 3.42-3.58 (m, 2H) 3.72 (dt, J=11.44, 3.98 Hz, 2H) 4.17 (s, 3H) 6.71 (d, J=2.20 Hz, 1H) 7.10 (s, 1H) 7.29 (s, 1H) 7.41-7.51 (m, 3H) 7.54-7.65 (m, 2H) 7.84 (d, J=2.20 Hz, 1H) 8.36 (d, J=1.83 Hz, 1H).

Examples 43 and 44

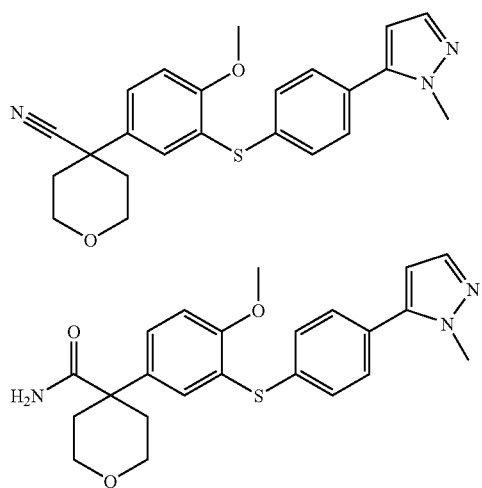

4-(4-methoxy-3-(4-(1-methyl-1H-pyrazol-5-yl)phenylthio)phenyl)-tetrahydro-2H-pyran-4-carbonitrile
and 4-(4-methoxy-3-(4-(1-methyl-1H-pyrazol-5-yl)phenylthio)phenyl)-tetrahydro-2H-pyran-4-carboxamide Step 1: Preparation of
2-bromo-4-(bromomethyl)-1-methoxybenzene To a solution of 2-bromo-1-methoxy-4-methylbenzene (2.5 g, 12 mmol) in carbon tetrachloride (40 mL) was added N-bromosuccinimide (2.77 g, 15.5 mmol) and benzoylperoxide (0.331 g, 1.37 mmol). After refluxing for 18 hours, the reaction was cooled to ambient temperature, poured into water (200 mL) and extracted with methylene chloride (3×75 mL), dried over magnesium sulfate, filtered and the solvent removed by evaporation under reduced pressure. The residue was purified by flash chromatography on silica gel eluting with a solvent gradient of ethyl acetate:heptane (5:95, by volume) changing to ethyl acetate:heptane (50:50, by volume), to provide the title compound (2.71 g) as an oil. $^1$H NMR (400 MHz, CHLOROFORM-d) δ ppm 3.91 (s, 3H) 4.45 (s, 2H) 6.86 (d, J=8.60 Hz, 1H) 7.31 (dd, J=8.40, 2.15 Hz, 1H) 7.60 (d, J=2.15 Hz, 1H).
LCMS: m/z [M-Br] 198.9, 200.9.

Step 2: Preparation of
2-(3-bromo-4-methoxyphenyl)acetonitrile

To a solution of 2-bromo-4-(bromomethyl)-1-methoxybenzene (2.71 g, 9.68 mmol) in anhydrous dimethylsulfoxide (30 mL), under nitrogen, was added sodium cyanide (549 mg, 10.6 mmol). After 2 hours the reaction was poured into 5% sodium chloride (200 mL), extracted with ethyl acetate (3×75 mL), washed with brine (100 mL), dried over magnesium sulfate, filtered and the solvent removed by evaporation under reduced pressure. The residue was purified by flash chromatography on silica gel eluting with a solvent gradient of ethyl acetate:heptane (5:95, by volume) changing to ethyl acetate:heptane (50:50, by volume), to provide the title compound (1.45 g) as an oil. $^1$H NMR (400 MHz, CHLOROFORM-d) δ ppm 3.69 (s, 2H) 3.91 (s, 3H) 6.90 (d, J=8.40 Hz, 1H) 7.23-7.27 (m, 1H) 7.51 (d, J=2.15 Hz, 1H).
LCMS: m/z [M–CN] 198.9, 200.9.

Step 3: Preparation of 4-(3-bromo-4-methoxyphenyl)-tetrahydro-2H-pyran-4-carbonitrile To a solution of 2-(3-bromo-4-methoxyphenyl)acetonitrile (500 mg, 2.21 mmol) in anhydrous N,N-dimethylformamide (5 mL), under argon, was added sodium hydride (186 mg, 4.64 mmo). After stirring for one hour 2-chloroethyl ether (0.556 mL, 4.64 mmol) was added and stirring was continued for 18 hours. After which time the reaction was poured into water (150 mL), extracted with ethyl acetate (3×75 mL), washed with brine (100 mL), dried over magnesium sulfate, filtered and the solvent removed by evaporation under reduced pressure, to provide the title compound (662 mg) as an oil. LCMS: m/z [MH+] 295.2, 297.2

Step 4: Preparation of 4-(4-methoxy-3-(4-(1-methyl-1H-pyrazol-5-yl)phenylthio)phenyl)-tetrahydro-2H-pyran-4-carbonitrile To a solution of -(3-bromo-4-methoxyphenyl)-tetrahydro-2H-pyran-4-carbonitrile (635 mg, 2.14 mmol), under argon, in degassed 1,4-dioxane (10 mL), was added S-4-(1-methyl-1H-pyrazol-5-yl)phenyl ethanethioate (498 mg, 2.14 mmol), palladium acetate (48 mg, 0.214 mmol), and bis(2-diphenylphosphinophenyl)ether (57.6 mg, 0.107 mmol) and sodium tert-butoxide (412 mg, 4.29 mmol). After heating to 100° C. for 20 min the reaction was cooled to room temperature and poured into water (200 mL), and filtered. The filtrate was extracted with ethyl acetate (3×75 mL), washed with brine (100 mL), dried over magnesium sulfate, filtered and the solvent removed by evaporation under reduced pressure. The residue was purified by flash chromatography on silica gel eluting with a solvent gradient of ethyl acetate:heptane (50:50, by volume) changing to ethyl acetate:heptane (100:0, by volume), to provide the title compound (610 mg) as a solid. $^1$H NMR (400 MHz, DMSO-d$_6$) δ ppm 1.91-2.08 (m, 4H) 3.34 (s, 3H) 3.54-3.65 (m, 2H) 3.84 (s, 3H) 3.92-3.96 (m, 1H) 3.96-4.00 (m, 1H) 6.41 (d, J=2.20 Hz, 1H) 7.21 (d, J=8.79 Hz, 1H) 7.30 (d, J=8.05 Hz, 2H) 7.36 (d, J=2.93 Hz, 1H) 7.46 (d, J=2.20 Hz, 1H) 7.51 (d, J=8.79 Hz, 2H) 7.55 (dd, J=8.79, 2.93 Hz, 1H). LCMS: m/z [MH+] 406.2.

Step 5: Preparation of 4-(4-methoxy-3-(4-(1-methyl-1H-pyrazol-5-yl)phenylthio)phenyl)tetrahydro-2H-pyran-4-carboxamide To a solution of 4-(4-methoxy-3-(4-(1-methyl-1H-pyrazol-5-yl)phenylthio)phenyl)tetrahydro-2H-pyran-4-carbonitrile (100 mg, 0.247 mmol) in tert-butanol (3 mL) was added potassium hydroxide. After heating to 70° C. for 18 hours, the reaction was cooled to ambient temperature, poured into water (200 mL), extracted with ethyl acetate (3×75 mL), washed with brine (100 mL), dried over magnesium sulfate, filtered and the solvent removed by evaporation under reduced pressure, to provide the title compound (100 mg) as a solid. $^1$H NMR (400 MHz, CHLOROFORM-d) δ ppm 1.94-2.07 (m, 2H) 2.27-2.31 (m, 1H) 2.31-2.37 (m, 1H) 3.70-3.79 (m, 4H) 3.88 (s, 3H) 3.89 (s, 3H) 5.26 (br. s., 2H) 6.31 (d, J=1.95 Hz, 1H) 6.98 (d, J=8.59 Hz, 1H) 7.28-7.39 (m, 6H) 7.51 (d, J=1.95 Hz, 1H). LCMS: m/z [MH+] 424.2

Example 45

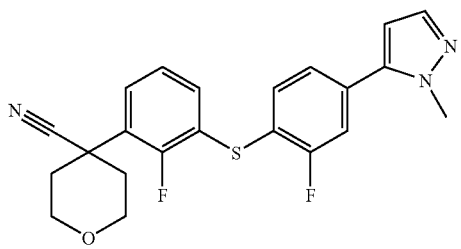

Step 1: Preparation of (4-bromo-3-fluorophenyl)(morpholino)methanone

To a solution of 4-bromo-3-fluorobenzoic acid (3.0 g, 14 mmol) in methylene chloride (50 mL) was added 1-ethyl-3-(3'-dimethylaminopropyl)carbodiimide hydrochloride (3.41 g, 1.3 mmol), dimethylaminopyridine (502 mg, 4.11 mmol), and morpholine (1.22 g, 14 mmol). After stirring for 3 hours at ambient temperature the reaction was poured into water (300 mL), washed with water (2×100 mL), and the organic dried over magnesium sulfate, filtered and the solvent removed by evaporation under reduced pressure, to provide the title compound (3.68 g) as an oil. $^1$H NMR (400 MHz, CHLOROFORM-d) δ ppm 3.31-3.92 (m, 8H) 7.05-7.13 (m, 1H) 7.20 (dd, J=8.40, 1.95 Hz, 1H) 7.62 (dd, J=8.20, 6.64 Hz, 1H).
LCMS: m/z [MH+] 288.0, 290.0.

Step 2: Preparation of 1-(4-bromo-3-fluorophenyl)ethanone

To an ice-bath cooled solution of (4-bromo-3-fluorophenyl)(morpholino)methanone (3.14 mg, 10.9 mmol) in anhydrous tetrahydrofuran (45 mL), under argon, was added methylmagnesium chloride (1.22 g, 16.4 mmol). The reaction was stirred at ice bath temperature for 1 hour then allowed to warm to ambient temperature. The reaction was poured into water (350 mL), extracted with ethyl acetate (3×75 mL), washed with brine (100 mL), dried over magnesium sulfate, filtered and the solvent removed by evaporation under reduced pressure, to provide the title compound (2.8 g) as a liquid. $^1$H NMR (400 MHz, CHLOROFORM-d) δ ppm 2.60 (s, 3H) 7.52-7.77 (m, 3H).

Step 3: Preparation of 5-(4-bromo-3-fluorophenyl)-1-methyl-1H-pyrazole

To a solution of 1-(4-bromo-3-fluorophenyl)ethanone (2.8 g, 12 mmol) in N,N-dimethylformamide (10 mL) was added N,N-dimethylformamide dimethyl acetal (3.45 mL, 26 mmol). The reaction was heated to reflux for three hours, cooled to room temperature, treated with methyl hydrazine (2.5 mL, 46 mmol), and heated to 75° C. for 18 hours. The reaction was cooled to room temperature, extracted with ethyl acetate (3×75 mL), washed with brine (100 mL), dried over magnesium sulfate, filtered and the solvent removed by evaporation under reduced pressure. The residue was purified by flash chromatography on silica gel eluting with a solvent gradient of ethyl acetate:heptane (20:80, by volume) changing to ethyl acetate:heptane (60:40 by volume), to provide the title compound (1.66 g) as a solid. $^1$H NMR (400 MHz, CHLOROFORM-d) δ ppm 3.91 (s, 3H) 6.34 (d, J=1.95 Hz, 1H) 7.11 (dd, J=8.01, 1.76 Hz, 1H) 7.20 (dd, J=8.99, 1.95 Hz, 1H) 7.53 (d, J=1.95 Hz, 1H) 7.65 (dd, J=8.20, 7.03 Hz, 1H). LCMS: m/z [MH+] 255.0, 257.0.

Step 4: Preparation of S-2-fluoro-4-(1-methyl-1H-pyrazol-5-yl)phenyl ethanethioate To a solution of 5-(4-bromo-3-fluorophenyl)-1-methyl-1H-pyrazole (120 mg, 0.470 mmol) in degassed, anhydrous 1,4-dioxane (13 mL), under argon, was added palladium acetate (8.1 mg, 0.036 mmol), bis(2-diphenylphosphinophenyl)ether (9.7 mg, 0.018 mmol), cesium carbonate (234 mg, 0.719 mmol), and triisopropylsilane thiol (205 mg, 0.231 mL, 1.08 mmol). The reaction was heated to 95° C. for 45 minutes, cooled to room temperature, and treated with acetic anhydride (1.5 mL) and stirred for 18 hours. The reaction was filtered, and the filtrate was extracted with ethyl acetate (3×75 mL), washed with brine (100 mL), dried over magnesium sulfate, filtered and the solvent removed by evaporation under reduced pressure. The residue was purified by flash chromatography on silica gel eluting with a solvent gradient of ethyl acetate:heptane (5:95, by volume) changing to ethyl acetate:heptane (40:60 by volume), to provide the title compound (50 mg) as a solid. $^1$H NMR (400 MHz, CHLOROFORM-d) δ ppm 2.50 (s, 3H) 3.96 (s, 3H) 6.38 (d, J=1.95 Hz, 1H) 7.23-7.29 (m, 2H) 7.51 (dd, J=8.30, 6.93 Hz, 1H) 7.55 (d, J=2.15 Hz, 1H). LCMS: m/z [MH+] 251.1

Step 5: Preparation of 4-(2-fluoro-3-(2-fluoro-4-(1-methyl-1H-pyrazol-5-yl)phenylthio)phenyl)tetrahydro-2H-pyran-4-carbonitrile To a solution of S-2-fluoro-4-(1-methyl-1H-pyrazol-5-yl)phenyl ethanethioate (100 mg, 0.400 mmol) in degassed, anhydrous 1,4-dioxane (3 mL), under argon, was added, ((2S, 4R)-4-(3-bromo-2-fluorophenyl)-2-methyl-tetrahydro-2H-pyran-4-carbonitrile) (119 mg, 0.0400 mmol), palladium acetate (13.7 mg, 0.060 mmol), and bis(2-diphenylphosphinophenyl)ether (21.5 mg, 0.040 mmol, and cesium carbonate (391 mg, 1.20 mmol). After heating to 85° C. for 18 hours the reaction was cooled to room temperature, filtered and purified by reverse phase HPLC, to provide the title compound (44 mg) as a glassy solid. $^1$H NMR (400 MHz, DMSO-d$_6$) δ ppm 1.19 (d, J=6.22 Hz, 3H) 1.72 (dd, J=13.18, 10.98 Hz, 1H) 1.96-2.05 (m, 1H) 2.19 (dt, J=13.36, 1.19 Hz, 1H) 2.28 (dt, J=13.45, 2.24 Hz, 1H) 3.69-3.81 (m, 2H) 3.89 (s, 3H) 4.00-4.06 (m, 1H) 6.52 (d, J=1.83 Hz, 1H) 7.28-7.35 (m, 2H) 7.38-7.51 (m, 4H) 7.58-7.63 (m, 1H). LCMS: m/z [MH+] 425.1.

Example 46

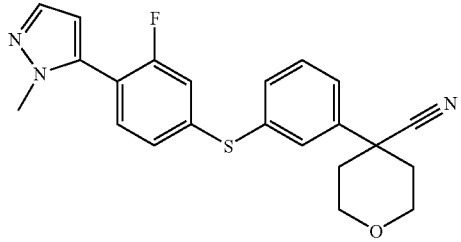

4-(3-{[3-fluoro-4-(1-methyl-1H-pyrazol-5-yl)phenyl]thio}phenyl)tetrahydro-2H-pyran-4-carbonitrile To a solution of 4-(3-{[3-fluoro-4-(1-methyl-1H-pyrazol-5-yl)phenyl]thio}phenyl)tetrahydro-2H-pyran-4-carboxamide (50 mg, 0.12 mmol) in 3 mL dichloromethane was added pyridine (0.099 mL, 1.22 mmol) followed by trifluoroacetic anhydride (0.119 mL, 0.854 mmol). The reaction was stirred for 30 minutes at room temperature and evaporated to a residue. Purification by reverse phase chromatography provided the title compound. 1H NMR (400 MHz, DMSO-$d_6$) δ ppm 7.42-7.75 (6H, m), 7.27 (1H, dd, J=10.6, 1.6 Hz), 7.16 (1H, dd, J=8.1, 1.6 Hz), 6.39 (1H, d, J=1.5 Hz), 3.95-4.09 (2H, m), 3.58-3.78 (5H, m), 2.01-2.20 (4H, m)

Example 47

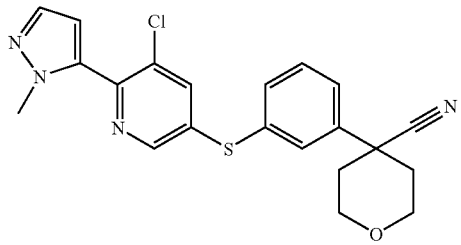

4-(3-{[5-chloro-6-(1-methyl-1H-pyrazol-5-yl)pyridin-3-yl]thio}phenyl)tetrahydro-2H-pyran-4-carbonitrile To a solution of 4-(3-{[5-chloro-6-(1-methyl-1H-pyrazol-5-yl)pyridin-3-yl]thio}phenyl)tetrahydro-2H-pyran-4-carboxamide (35 mg, 0.082 mmol) in 3 mL dichloromethane was added pyridine (0.066 mL, 0.82 mmol) followed by trifluoroacetic anhydride (0.08 mL, 0.574 mmol). The reaction was stirred for 30 minutes at room temperature and evaporated to a residue. Purification by reverse phase chromatography provided the title compound. 1H NMR (400 MHz, DMSO-$d_6$) δ ppm 8.53 (1H, d, J=1.8 Hz), 8.01 (1H, d, J=2.0 Hz), 7.73 (1H, br. s.), 7.47-7.68 (4H, m), 6.66 (1H, d, J=2.0 Hz), 3.95-4.08 (2H, m), 3.84 (3H, s), 3.57-3.73 (2H, m), 2.00-2.21 (4H, m)

Example 48

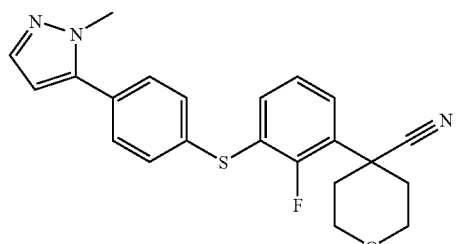

4-(2-fluoro-3-{[4-(1-methyl-1H-pyrazol-6-yl)phenyl]thio}phenyl)tetrahydro-2H-pyran-4-carbonitrile To a solution of 4-(2-fluoro-3-{[4-(1-methyl-1H-pyrazol-5-yl)phenyl]thio}phenyl)tetrahydro-2H-pyran-4-carboxamide (30 mg, 0.073 mmol) in 3 mL dichloromethane was added pyridine (0.059 mL, 0.73 mmol) followed by trifluoroacetic anhydride (0.071 mL, 0.511 mmol). The reaction was stirred for 30 minutes at room temperature and evaporated to a residue. Purification by reverse phase chromatography provided the title compound. 1H NMR (400 MHz, DMSO-$d_6$) δ ppm 7.27-7.64 (8H, m), 6.44 (1H, d, J=1.8 Hz), 4.01 (2H, dd, J=12.1, 2.6 Hz), 3.86 (3H, s), 3.69 (2H, t, J=11.4 Hz), 2.03-2.29 (4H, m)

Example 49

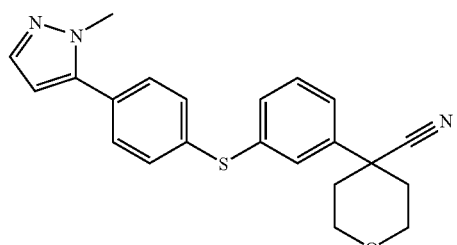

4-(3-{[4-(1-methyl-1H-pyrazol-5-yl)phenyl]thio}phenyl)tetrahydro-2H-pyran-4-carbonitrile To a solution of 4-(3-{[4-(1-methyl-1H-pyrazol-5-yl)phenyl]thio}phenyl)tetrahydro-2H-pyran-4-carboxamide (50 mg, 0.13 mmol) in 3 mL dichloromethane was added pyridine (0.103 mL, 1.27 mmol) followed by trifluoroacetic anhydride (0.124 mL, 0.889 mmol). The reaction was stirred for 30 minutes at room temperature and evaporated to a residue. Purification by reverse phase chromatography provided the title compound. 1H NMR (400 MHz, DMSO-$d_6$) δ ppm 7.28-7.65 (9H, m), 6.43 (1H, d, J=1.8 Hz), 3.93-4.10 (2H, m), 3.85 (3H, s), 3.53-3.74 (2H, m), 1.96-2.19 (4H, m)

Example 50

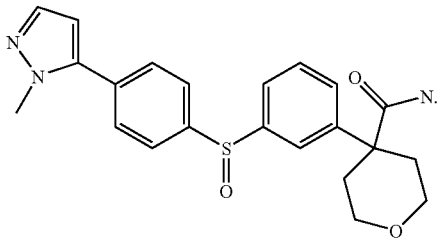

4-(3-{[4-(1-methyl-1H-pyrazol-5-yl)phenyl]
sulfinyl}phenyl)tetrahydro-2H-pyran-4-carboxamide 187.2 mg of 4-(3-{[4-(1-methyl-1H-pyrazol-5-yl)phenyl]thio}phenyl)tetrahydro-2H-pyran-4-carboxamide and 2 mls of 1,1,1,3,3,3-hexafluoro-2-propanol were placed in an oven dried vial. 40 ul of hydrogen peroxide was added and the mixture stirred at room temperature for 2 hours. The reaction was quenched with the addition of 8 mls methylene chloride and 2 mls of 5% aqueous sodium thiosulfate. The reaction mixture was stirred for 10 minutes then washed with water, dried with magnesium sulfate, filtered, concentrated and purified by reverse phase chromatography. The product fractions were diluted into ethyl acetate, extracted with 5% aqueous sodium bicarbonate, dried with magnesium sulfate, filtered, concentrated and vacuum dried to give 175 mg of product. HRMS (M+H) calc 410.1538, found 410.1511. 1H NMR (400 MHz, DMSO-$d_6$) δ ppm 1.74-1.85 (m, 2H) 2.45 (d, J=12.89 Hz, 2H) 3.47 (t, J=11.01 Hz, 2H) 3.73 (dt, J=11.55, 3.49 Hz, 2H) 3.85 (s, 3H) 6.47 (d, J=2.15 Hz, 1H) 7.10 (s, 1H) 7.32 (s, 1H) 7.48 (d, J=1.88 Hz, 1H) 7.52 (d, J=5.10 Hz, 2H) 7.61 (td, J=4.43, 1.61 Hz, 1H) 7.70 (ddd, J=8.46, 2.15, 2.01 Hz, 2H) 7.83 (dt, J=8.39, 1.98 Hz, 3H).

Example 51

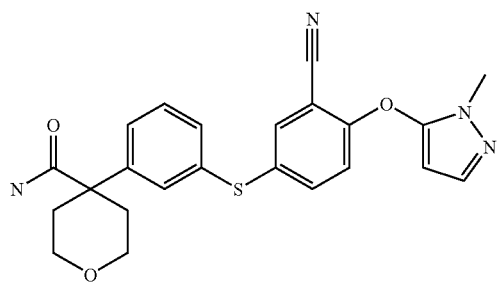

4-[3-({3-cyano-4-[(1-methyl-1H-pyrazol-5-yl)oxy]phenyl}thio)phenyl]tetrahydro-2H-pyran-4-carboxamide Step 1: Preparation of
5-iodo-2-(1-methyl-1H-pyrazol-5-yloxy)benzonitrile A solution of 2-fluoro-5-iodobenzonitrile (100 mg, 0.405 mmol) and 2-methyl-2,4-dihydro-3H-pyrazol-3-one (63.6 mg, 0.648 mmol) in 5 mL of 1-methyl-2-pyrrolidinone was treated with cesium carbonate (396 mg, 1.22 mmol) and stirred at 110° C. for 2 hour. The reaction was diluted with 50 mL water and extracted with 2×50 mL ethyl acetate. The combined organic layers were washed with 50 mL water, 50 mL brine, dried over magnesium sulfate, filtered, and evaporated to afford crude material. Purification by normal phase chromatography provided the title compound as a white solid (93 mg). LC/MS 5-100% acetonitrile/tfa-water/tfa (6 min gradient) 4.74 min [(M+H)$^+$=326]. 1H NMR (400 MHz, DMSO-de) δ ppm 8.33 (1H, d, J=2.2 Hz), 8.04 (1H, dd, J=8.9, 2.2 Hz), 7.45 (1H, d, J=2.0 Hz), 6.95 (1H, d, J=8.9 Hz), 5.99 (1H, d, J=2.0 Hz), 3.67 (3H, s)

Step 2: Preparation of 4-[3-({3-cyano-4-[(1-methyl-1H-pyrazol-5-yl)oxy]phenyl}thio)phenyl]tetrahydro-2H-pyran-4-carboxamide 4-{3-[(triisopropylsilyl)thio]phenyl}tetrahydro-2H-pyran-4-carboxamide (131 mg, 0.332 mmol), 5-iodo-2-(1-methyl-1H-pyrazol-5-yloxy)benzonitrile (90 mg, 0.28 mmol), bis[(2-diphenylphosphino)phenyl]ether (7.5 mg, 0.014 mmol), and palladium tetrakis(triphenylphosphine) (19.6 mg, 0.017 mmol) were placed in a flask and evacuted/argon filled three times. Anhydrous 1,4-dioxane (2 mL) was then added, followed by the addition of 0.554 mL of 2 M aqueous cesium carbonate (argon saturated). The reaction was heated at 80° C. for four hours and cooled to room temperature. The reaction mix was diluted with 50 mL water and washed with 2×50 mL ethyl acetate. The combined organic layers were washed with 50 mL water, 50 mL brine, dried over magnesium sulfate, filtered, and evaporated to afford crude material. Purification by normal phase chromatography provided the title compound as a white solid (41 mg). LC/MS 5-100% acetonitrile/tfa-water/tfa (6 min gradient) 4.46 min [(M+H)$^+$=435]. 1H NMR (400 MHz, DMSO-$d_6$) □ ppm 7.92 (1H, d, J=2.4 Hz), 7.60 (1H, dd, J=8.9, 2.2 Hz), 7.31-7.51 (4H, m), 7.12-7.31 (3H, m), 7.07 (1H, br. s.), 5.98 (1H, d, J=2.0 Hz), 3.61-3.82 (5H, m), 3.45 (2H, t, J=10.5 Hz), 2.39 (2H, d, J=13.7 Hz), 1.68-1.87 (2H, m).

Example 52

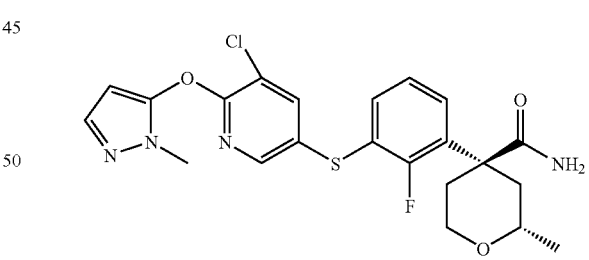

(2S,4R)-4-(3-(5-chloro-6-(1-methyl-1H-pyrazol-5-yloxy)pyridin-3-ylthio)-2-fluorophenyl)-2-methyltetrahydro-2H-pyran-4-carboxamide Step 1: Preparation of 1-methyl-1H-pyrazol-5-ol To a solution of 3-methocyacriylic acid methyl ester (2.44 g, 20 mmol) in methanol (6 ml) was added methylhydrazine (921 mg, 20 mmol). The reaction was stirred at 90° C. for 12 hours then cooled to room temperature and concentrated to give the crude product as an off-white semi-sold (2.97 g, 96.8%). 1H NMR (400 MHz, DMSO-$d_6$) δ ppm 7.21 (s, 1H), 7.09 (d, J=2.05 Hz, 1H), 5.31 (d, J=2.05 Hz, 1H), 3.49 (s, 3H).

Step 2: Preparation of 5-bromo-3-chloro-2-(1-methyl-1H-pyrazol-5-yloxy)pyridine

To a solution of 5-bromo-2,3-dichloropyridine (3.22 g, 14 mmol) and 1-methyl-1H-pyrazol-5-ol (1.4 g, 14 mmol in DMF (4 ml) was added cesium carbonate (13.9 g, 42 mmol). The reaction was stirred 3 hours at 100° C., then diluted with ethyl acetate (50 ml) and washed with water (1×50 ml) and brine (1×50 ml). The organic phase was dried over magnesium sulfate and filtered. The filtrate was evaporated to give the crude product as an oil that solidified upon standing (3.2 g, 79%). LC/MS (5%-95% $CH_3CN$:$H_2O$) gradient over 5 minutes: 2.89 min. 289 M+H.

Step 3: Preparation of S-5-chloro-6-(1-methyl-1H-pyrazol-5-yloxy)pyridin-3-yl ethanethioate Placed 1,1'-bis(diphenylphosphino)ferrocene palladium dichloride (202 mg, 0.276 mmol), and 1,1'-bis(diphenylphosphino)ferrocene (77.1 mg, 0.139 mmol) in flask under nitrogen followed by addition of 5-bromo-3-chloro-2-(1-methyl-1H-pyrazol-5-yloxy)pyridine (1.60 g, 5.5 mmol) in 20 mL 1,4-dioxane. The reaction was degassed for 15 min. followed by the addition of triisopropylsilanethiol (1.17 mg, 6.16 mmol) and 1.0 M potassium t-butoxide in THF (6.10 mL, 684 mg, 6.10 mmol). The mixture was heated at 92° C. for 3 h. Added 1.0 M potassium-t-butoxide (6.0 mL, 6.0 mmol), 1,1'-bis(diphenylphosphino)ferrocene palladium dichloride (202 mg, 0.276 mmol), and 1,1'-bis(diphenylphosphino)ferrocene (77.1 mg, 0.139 mmol). Heated reaction to reflux for 4 h. The mixture was cooled to room temperature. Sat. $NH_4Cl$ (30 mL) was added and the mixture was extracted with ethyl acetate (30 mL). The organic layer was collected. A solution of TBAF (1.0M in THF) (7.65 mL, 2.00 g, 7.65 mmol) was added and stirred for 10 min. Acetic anhydride was added and the reaction was stirred at room temperature for 10 min. The mixture was poured into water and extracted with diethyl ether (2×30 mL). The organic layer was dried over magnesium sulfate, filtered and concentrated. Purification over silica afforded the title compound as a light yellow solid (210 mg, 13%). 1H NMR (400 MHz, DMSO-$d_6$) δ ppm 8.27 (d, J=2.05 Hz, 1H), 8.16 (d, J=2.05 Hz, 2H), 7.44 (d, J=2.39 Hz), 6.14 (d, J=2.05 Hz, 1H), 3.64 (s, 5H).

Step 4: Preparation of (2S,4R)-4-(3-(5-chloro-6-(1-methyl-1H-pyrazol-5-yloxy)pyridin-3-ylthio)-2-fluorophenyl)-2-methyl-tetrahydro-2H-pyran-4-carbonitrile To a degassed dioxane (3 mL) solution of (2S,4R)-4-(3-bromo-2-fluorophenyl)-2-methyl-tetrahydro-2H-pyran-4-carbonitrile (231 mg, 0.775 mmol) and S-5-chloro-6-(1-methyl-1H-pyrazol-5-yloxy)pyridin-3-yl ethanethioate (220 mg, 0.775 mmol) was added DPEphos (42 mg, 0.078 mmol) and palladium (II) acetate (27 mg, 0.116 mmol). To this was added degassed 2N $Cs_2CO_3$. The vial was sealed under N2 and heated to 90° C. for 18 hours. The reaction was cooled to room temperature, quenched with 25 mL water, extracted with ethyl acetate (2×25 mL), combined extracts, dried over magnesium sulfate, filtered and concentrated to a tan oil. The product was isolated by reverse phase chromatography. 1H NMR (400 MHz, DMSO-d6) δ ppm 8.31 (d, J=2.20 Hz, 1H), 8.23 (d, J=1.83 Hz, 1H), 7.37-7.45 (m, 2H), 7.22-7.29 (m, 2H), 6.11 (d, J=2.20 Hz, 1H), 4.02 (dd, J=12.08, 2.93 Hz, 1H), 3.68-3.80 (m, 2H), 3.61 (s, 3H), 2.26 (d, J=13.54 Hz, 1H), 2.16 (br. s., 1H), 1.99 (td, J=12.90, 4.58 Hz, 1H), 1.70 (dd, J=13.18, 10.98 Hz, 1H), 1.18 (d, J=6.22 Hz, 3H)

Step 5: Preparation of (2S,4R)-4-(3-(5-chloro-6-(1-methyl-1H-pyrazol-5-yloxy)pyridin-3-ylthio)-2-fluorophenyl)-2-methyl-tetrahydro-2H-pyran-4-carboxamide (2S,4R)-4-(3-(5-chloro-6-(1-methyl-1H-pyrazol-5-yloxy)pyridin-3-ylthio)-2-fluorophenyl)-2-methyl-tetrahydro-2H-pyran-4-carbonitrile (77 mg, 0.17 mmol) was dissolved in a 5 mL solution of 4:1 TFA:$T_2SO_4$. The mixture was heated to 90° C. for 2 h. The reaction was cooled, neutralized with 2.5N NaOH, extracted into ethyl acetate (5 mL), dried over magnesium sulfate, filtered and concentrated to 100 mg oil. The product was isolated by reverse phase chiral chromatography. 1H NMR (400 MHz, DMSO-d6) δ ppm 8.17-8.22 (m, 1H), 8.11-8.15 (m, 1H), 7.36-7.43 (m, 2H), 7.06-7.23 (m, 3H), 6.08-6.12 (m, 1H), 3.75-3.84 (m, 1H), 3.61 (s, 4H), 2.31-2.41 (m, 1H), 1.69-1.80 (m, 1H), 1.34-1.45 (m, 1H), 1.19-1.25 (m, 1H), 1.03-1.10 (m, 3H).

Example 53

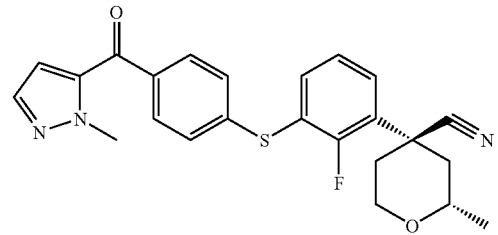

(2S,4R)+(2-fluoro-3-(4-(1-methyl-1H-pyrazole-5-carbonyl)phenylthio)phenyl)-2-methyl-tetrahydro-2H-pyran-4-carbonitrile To a degassed dioxane (3 mL) solution of (2S,4R)-4-(3-bromo-2-fluorophenyl)-2-methyl-tetrahydro-2H-pyran-4-carbonitrile (286 mg, 0.959 mmol) and S-4-(1-methyl-1H-pyrazole-5-carbonyl)phenyl ethanethioate (250 mg, 0.959 mmol) was added DPEphos (51.7 mg, 0.096 mmol) and Pd(I-I)(OAc)$_2$ (33 mg, 0.144 mmol). To this was added degassed 2N $Cs_2CO_3$ (2 mL). The vial was capped under $N_2$ and heated to 90° C. for 18 hours. The reaction was cooled to room temperature, quenched with 25 mL water, extracted with ethyl acetate (2×25 mL), combined extracts, dried over magnesium sulfate, filtered and concentrated to a tan oil (620 mg). The product was isolated by reverse phase chiral chromatography and obtained as a light-yellow oil. 1H NMR (400 MHz, DMSO-$d_6$) δ ppm 7.81 (d, J=8.42 Hz, 3H), 7.54-7.64 (m, 2H), 7.39 (t, J=7.87 Hz, 1H), 7.34 (d, J=8.42 Hz, 2H), 6.75 (d, J=2.20 Hz, 1H), 4.06 (s, 3H), 3.99-4.05 (m, 1H), 3.68-3.81 (m, 2H), 2.28 (dt, J=13.18, 2.20 Hz, 1H), 2.19 (dt, J=13.54, 1.10 Hz, 1H), 1.97-2.06 (m, 1H), 1.73 (dd, J=13.18, 10.98 Hz, 1H), 1.14-1.22 (m, 3H). HRMS calc M+H: 436.1495, found 436.1494.

Example 54

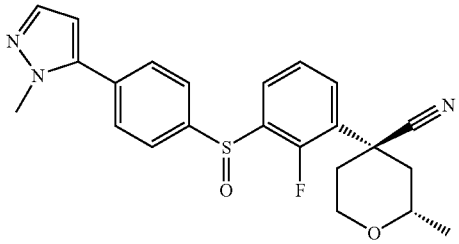

(2S,4R)-4-(2-fluoro-3-(4-(1-methyl-1H-pyrazol-5-yl)phenylsulfinyl)phenyl)-2-methyl-tetrahydro-2H-pyran-4-carbonitrile (2S,4R)-4-(2-fluoro-3-(4-(1-methyl-1H-pyrazol-5-yl)phenylthio)phenyl)-2-methyl-tetrahydro-2H-pyran-4-carbonitrile (70 mg, 0.17 mmol, 1 eq) was dissolved in hexafluoroisopropanol (10.0 mL). Hydrogen peroxide 30% (4.0 mL, 40 mmol) was added to the solution and stirred for 24 hrs. The reaction mixture was diluted with brine (10 ml) and ethyl acetate (15 ml) and the layers separated. The organic phase was concentrated under vacuum to an oil. The oil was purified by reverse phase chromatography to obtain the desired product (70.0 mg, 96%). 1H NMR (400 MHz, DMSO-d6) d ppm 1.16 (dd, J=6.22, 3.29 Hz, 3H) 1.60-1.77 (m, 2H) 1.92-2.03 (m, 2H) 2.07-2.23 (m, 2H) 3.84 (s, 3H) 4.00 (d, J=11.71 Hz, 1H) 6.49 (s, 1H) 7.48 (s, 1H) 7.56 (t, J=8.05 Hz, 1H) 7.64-7.71 (m, 1H) 7.73-7.84 (m, 4H) 7.89 (t, J=6.22 Hz, 1H) ES-HRMS m/z 424.1504 (M+H calcd: 424.1495).

Using the procedures and the general schemes disclosed above, the following compounds were also prepared:

| Ex # | IUPAC NAME | NMR data |
|---|---|---|
| 55 | 4-(2-chloro-3-{[4-(1-methyl-1H-pyrazol-5-yl)phenyl]thio}phenyl)-N-methyltetrahydro-2H-pyran-4-carboxamide | 1H NMR (400 MHz, DMSO-d6) δ ppm 1.96-2.07 (m, 2H) 2.33 (ddd, J = 13.29, 5.64, 2.55 Hz, 2H) 2.53 (d, J = 4.57 Hz, 3H) 3.54-3.63 (m, 2H) 3.81 (ddd, J = 11.28, 8.19, 2.82 Hz, 2H) 3.88 (s, 3H) 6.48 (d, J = 1.88 Hz, 1H) 6.99 (dd, J = 7.79, 1.34 Hz, 1H) 7.04 (q, J = 4.39 Hz, 1H) 7.35 (t, J = 7.92 Hz, 1H) 7.47-7.53 (m, 4H) 7.61 (ddd, J = 8.46, 2.15, 2.01 Hz, 2H). |
| 56 | 4-(3-{[4-(4-chloro-1-methyl-1H-pyrazol-5-yl)-3-fluorophenyl]thio}phenyl)tetrahydro-2H-pyran-4-carboxamide | 1H NMR (400 MHz, CHLOROFORM-d) d ppm 2.04-2.13 (m, 2H) 2.34-2.41 (m, 2H) 3.75 (d, J = 1.37 Hz, 3H) 3.76-3.87 (m, 4H) 5.28 (br. s., 2H) 6.97 (dd, J = 10.16, 1.76 Hz, 1H) 7.08 (dd, J = 8.01, 1.76 Hz, 1H)7.23-7.29 (m, 1H) 7.45 (d, J = 1.17 Hz, 3H) 7.51 (s, 1H) 7.56 (s, 1H); ES-HRMS m/z 446.1202 (M + H calc.: 446.1105). |
| 57 | 4-(3-{[4-(4-chloro-1-methyl-1H-pyrazol-5-yl)phenyl]thio}phenyl)tetrahydro-2H-pyran-4-carboxamide | 1H NMR (400 MHz, CHLOROFORM-d) d ppm 2.03-2.12 (m, 2H) 2.32-2.39 (m, 2H) 3.75-3.85 (m, 7H)5.24 (br. s., 2H) 7.32-7.40 (m, 7H) 7.48-7.49 (m, 1H) 7.50 (s, 1H); ES-HRMS m/z 428.1299 (M + H calc.: 428.1199). |
| 58 | 4-[3-({3-fluoro-4-[(1-methyl-1H-pyrazol-5-yl)carbonyl]phenyl}thio)phenyl]tetrahydro-2H-pyran-4-carboxamide | 1H NMR (400 MHz, DMSO-d$_6$) d ppm 1.74-1.87 (m, 2H), 2.36-2.45 (m, 2H), 3.46 (br. s., 2H), 3.65-3.77 (m, 2H), 4.09 (s, 3H), 6.63-6.69 (m, 1H), 7.04 (d, J = 9.52 Hz, 3H), 7.21-7.27 (m, 1H), 7.51 (dd, J = 19.76, 5.12 Hz, 6H) |
| 59 | 4-(3-{[4-(4-ethyl-1H-pyrazol-5-yl)phenyl]thio}phenyl)tetrahydro-2H-pyran-4-carboxamide | 1H NMR (400 MHz, DMSO-d6) d ppm 1.14 (t, J = 7.32 Hz, 3H) 1.69-1.81 (m, 2H) 2.38 (d, J = 13.18 Hz, 2H)2.55-2.64 (m, 2H) 3.43 (t, J = 10.62 Hz, 2H) 3.71 (d, J = 11.71 Hz, 2H) 7.07 (s, 1H) 7.13-7.23 (m, 1H) 7.25-7.45 (m, 7H) 7.52 (br. s., 1H) 7.59-7.68 (m, 2H) |
| 60 | 4-(3-{[4-(4-bromo-1H-pyrazol-5-yl)phenyl]thio}phenyl)tetrahydro-2H-pyran-4-carboxamide | 1H NMR (400 MHz, DMSO-d6) d ppm 1.71-1.83 (m, 2H) 2.39 (d, J = 13.18 Hz, 2H) 3.44 (t, J = 11.71 Hz, 2H) 3.72 (d, J = 11.71 Hz, 2H) 7.08 (s, 1H) 7.18-7.30 (m, 2H) 7.33-7.48 (m, 4H) 7.65-7.73 (m, 1H) 7.78-7.85 (m, 1H) 8.09 (s, 1H) |
| 61 | 4-[3-({5-chloro-6-[(1-methyl-1H-pyrazol-5-yl)oxy]pyridin-3-yl}thio)-2-fluorophenyl]tetrahydro-2H-pyran-4-carboxamide | 1H NMR (400 MHz, DMSO-d6) d ppm 1.86-2.06 (m, 2H) 2.16 (s, 2H) 2.30 (d, J = 13.91 Hz, 2H) 3.60-3.74 (m, 5H) 3.96 (s, 3H) 6.91-7.03 (m, 1H) 7.17-7.24 (m, 1H) 7.50-7.66 (m, 7H) 8.08-8.19 (m, 1H). |
| 62 | 4-[3-({4-[(1-methyl-1H-pyrazol-5-yl)carbonyl]phenyl}thio)phenyl]tetrahydro-2H-pyran-4-carbonitrile | 1H NMR (400 MHz, DMSO-d) d ppm 8.24 (1H, d, J = 2.0 Hz), 8.18 (1H, d, J = 2.0 Hz), 7.38-7.60 (5H, m), 7.25 (1H, d, J = 7.5 Hz), 7.06-7.18 (1H, m), 3.93-4.06 (2H, m), 3.57-3.71 (2H, m), 1.97-2.16 (4H, m) |
| 63 | 4-[3-({2,5-difluoro-4-[(1-methyl-1H- | 1H NMR (400 MHz, DMSO-d$_6$) d ppm 1.76-1.86 (m, 2H), 2.40 (d, J = 13.91 Hz, 2H), 3.46 (t, J = 10.25 Hz, 2H), 3.67-3.75 (m, 2H), 4.10 (s, 3H), |

| Ex # | IUPAC NAME | NMR data |
|---|---|---|
|  | pyrazol-5-yl)carbonyl]phenyl}thio)phenyl]tetrahydro-2H-pyran-4-carboxamide | 6.75 (s, 1H), 6.77 (d, J = 4.39 Hz, 1H), 7.03 (br. s., 1H), 7.23 (br. s., 1H), 7.40-7.46 (m, 1H), 7.46-7.61 (m, 5H) |
| 64 | 4-[3-({3-methoxy-4-[(1-methyl-1H-pyrazol-5-yl)carbonyl]phenyl}thio)phenyl]-N-methyltetrahydro-2H-pyran-4-carboxamide | 1H NMR (400 MHz, DMSO-d6) d ppm 1.78-1.91 (m, 2H), 2.36-2.42 (m, 2H), 2.48 (s, 3H), 3.41 (t, J = 10.25 Hz, 2H), 3.62 (s, 3H), 3.63-3.78 (m, 2H), 4.09 (s, 3H), 6.48 (d, J = 2.20 Hz, 1H), 6.79 (d, J = 8.05 Hz, 1H), 6.98 (s, 1H), 7.33-7.57 (m, 6H) 7.63 (d, 1H) |
| 65 | 4-[3-({3-chloro-4-[(1-methyl-1H-pyrazol-5-yl)carbonyl]phenyl}thio)phenyl]-N-methyltetrahydro-2H-pyran-4-carboxamide | 1H NMR (400 MHz, DMSO-d) d ppm 7.37-7.73 (7H, m), 7.16-7.35 (2H, m), 6.55 (1H, d, J = 2.2 Hz), 4.15 (3H, s), 3.64-3.81 (2H, m), 3.45 (2H, t, J = 10.2 Hz), 2.52-2.60 (3H, m), 2.40 (2H, d, J = 13.5 Hz), 1.75-1.95 (2H, m) |
| 66 | 4-[3-({4-[(1-methyl-1H-pyrazol-5-yl)carbonyl]phenyl}sulfinyl)phenyl]tetrahydro-2H-pyran-4-carboxamide | 1H NMR (400 MHz, DMSO-d6) d ppm 1.76-1.86 (m, 1H), 1.81 (d, J = 2.93 Hz, 1H), 2.44 (d, J = 13.17 Hz, 2H), 3.26 (s, 1H), 3.48 (t, J = 10.61 Hz, 2H), 3.73 (d, J = 11.71 Hz, 2H), 4.09 (s, 3H), 6.76 (d, J = 1.83 Hz, 1H), 7.05 (br. s., 1H), 7.27 (br. s., 1H), 7.52-7.56 (m, 2H), 7.62 (d, J = 3.29 Hz, 1H), 7.58 (d, J = 1.83 Hz, 1H), 7.82 (s, 1H), 7.88-7.99 (m, 3H) |
| 67 | 4-[3-({2-fluoro-4-[(1-methyl-1H-pyrazol-5-yl)carbonyl]phenyl}thio)phenyl]tetrahydro-2H-pyran-4-carboxamide | 1H NMR (400 MHz, DMSO-d) d ppm 7.35-7.76 (7H, m), 7.25 (1H, br. s.), 6.99-7.18 (2H, m), 6.82 (1H, d, J = 2.0 Hz), 4.08 (3H, s), 3.73 (2H, d, J = 11.7 Hz), 3.47 (2H, t, J = 11.4 Hz), 2.41 (2H, d, J = 13.7 Hz), 1.74-1.92 (2H, m) |
| 68 | 4-[3-({2-chloro-4-[(1-methyl-1H-pyrazol-5-yl)carbonyl]phenyl}thio)phenyl]tetrahydro-2H-pyran-4-carboxamide | 1H NMR (400 MHz, DMSO-d6) d ppm 7.89 (1H, d, J = 1.6 Hz), 7.41-7.77 (6H, m), 7.26 (1H, br. s.), 7.05 (1H, br. s.), 6.73-6.93 (2H, m), 4.07 (3H, s), 3.74 (2H, d, J = 11.7 Hz), 3.40-3.59 (2H, m), 2.43 (2H, d, J = 12.8 Hz), 1.76-1.94 (2H, m) |
| 69 | 4-[3-({6-[(1-methyl-1H-pyrazol-5-yl)carbonyl]pyridin-3-yl}thio)phenyl]tetrahydro-2H-pyran-4-carboxamide | 1H NMR (400 MHz, DMSO-d6) d ppm 1.82-2.02 (m, 2H), 2.43-2.58 (m, 2H), 3.51-3.65 (m, 2H), 3.78-3.91 (m, 2H), 4.22 (s, 3H), 7.08-7.20 (m, 1H), 7.30-7.41 (m, 1H), 7.43 (s, 1H), 7.51-7.65 (m, 3H), 7.63-7.72 (m, 2H), 7.80-7.90 (m, 1H), 8.04-8.15 (m, 1H), 8.55-8.68 (m, 1H) |
| 70 | 4-[3-({2-methoxy-4-[(1-methyl-1H-pyrazol-5-yl)carbonyl]phenyl}thio)phenyl]tetrahydro-2H-pyran-4-carboxamide | 1H NMR (400 MHz, DMSO-d6) d ppm 1.70-1.92 (m, 2H), 2.24-2.47 (m, 2H), 3.48 (t, J = 10.25 Hz, 2H), 3.62-3.81 (m, 2H), 3.93 (s, 3H), 4.07 (s, 3H), 6.67-6.90 (m, 2H), 7.04 (br. s., 1H), 7.13-7.29 (m, 1H), 7.29-7.69 (m, 7H) |
| 71 | 4-[3-({3-methoxy-4-[(1-methyl-1H-pyrazol-5-yl)carbonyl]phenyl}thio)phenyl]tetrahydro-2H-pyran-4-carboxamide | 1H NMR (400 MHz, DMSO-d6) d ppm 1.62-1.91 (m, 2H), 2.26-2.47 (m, 2H), 3.48 (t, J = 10.25 Hz, 2H), 3.65 (s, 3H), 3.67-3.81 (m, 2H), 4.10 (s, 3H), 6.50 (d, J = 2.20 Hz, 1H), 6.80 (d, J = 8.05 Hz, 1H), 6.86-7.12 (m, 2H), 7.11-7.63 (m, 7H) |
| 72 | N-methyl-4-[3-({4-[(1-methyl-1H-pyrazol-5-yl)carbonyl]phenyl}thio)phenyl]tetrahydro-2H-pyran-4-carboxamide | 1H NMR (400 MHz, DMSO-$d_6$) d ppm 1.83 (br. s., 2H), 2.37 (d, J = 14.64 Hz, 2H), 2.52 (d, J = 5.12 Hz, 3H), 3.42 (s, 2H), 3.69 (d, J = 11.71 Hz, 2H), 4.05 (s, 3H), 6.73 (s, 1H), 7.27 (m, J = 8.78 Hz, 2H), 7.44 (dd, J = 10.61, 3.29 Hz, 4H), 7.56 (s, 2H), 7.77 (m, J = 8.78 Hz, 2H) |
| 73 | (2S,4R)-4-(3-{[4-(4-bromo-1-methyl-1H-pyrazol-5-yl)phenyl]thio}-2-fluorophenyl)-2-methyltetrahydro-2H-pyran-4-carboxamide | 1H NMR (400 MHz, DMSO-d6) d ppm 1.08 (d, J = 6.59 Hz, 3H) 1.42 (t, 1H) 1.77 (td, J = 13.00, 4.76 Hz, 1H) 2.34-2.45 (m, 1H) 3.57-3.72 (m, 3H) 3.76 (s, 3H) 3.79 (dd, J = 11.71, 3.66 Hz, 1H) 7.11 (d, J = 5.86 Hz, 2H) 7.25-7.33 (m, 3H) 7.38 (t, J = 6.22 Hz, 1H) 7.44-7.52 (m, 3H) 7.64 (s, 1H) |
| 74 | (2S,4S)-4-(4-fluoro-3-{[4-(1-methyl-1H- | 1H NMR (400 MHz, CHLOROFORM-d) d ppm 1.19 (d, J = 6.25 Hz, 3H) 2.05 (dd, J = 14.27, 10.55 Hz, 1H) 2.31-2.39 (m, 3H) 3.35-3.51 (m, 2H) |

| Ex # | IUPAC NAME | NMR data |
|---|---|---|
| | pyrazol-5-yl)phenyl]thio}phenyl)-2-methyltetrahydro-2H-pyran-4-carbonitrile | 3.81-3.97 (m, 4H) 6.33 (d, J = 2.15 Hz, 1H) 7.17-7.27 (m, 1H)7.35-7.44 (m, 6H) 7.56 (d, J = 1.95 Hz, 1H) |
| 75 | (2R,4S)-4-(4-fluoro-3-{[4-(1-methyl-1H-pyrazol-5-yl)phenyl]thio}phenyl)-2-methyltetrahydro-2H-pyran-4-carboxamide | 1H NMR (400 MHz, DMSO-d6) d ppm 1.09 (d, J = 5.86 Hz, 3H) 1.20-1.31 (m, 2H) 1.49-1.63 (m, 2H) 2.51-2.59 (m, 2H) 3.37-3.49 (m, 2H) 3.83 (s, 3H) 6.39 (s, 1H) 7.12 (br. s., 1H) 7.26 (d, J = 8.05 Hz, 2H) 7.31-7.39 (m, 2H) 7.43-7.54 (m, 4H) 7.64-7.74 (m, 1H) |
| 76 | 4-(3-{[4-(4-bromo-1-methyl-1H-pyrazol-5-yl)phenyl]thio}phenyl)tetrahydro-2H-pyran-4-carboxamide | 1H NMR (400 MHz, CHLOROFORM-d) d ppm 2.01-2.11 (m, 2H) 2.31-2.40 (m, 2H) 3.74-3.83 (m, 7H)5.25 (br. s., 2H) 7.29-7.42 (m, 7H) 7.46-7.49 (m, 1H) 7.53 (s, 1H); ES-HRMS m/z 472.0796 (M + H calc.: 472.0694). |
| 77 | (2S,4S)-4-(4-fluoro-3-{[4-(1-methyl-1H-pyrazol-5-yl)phenyl]thio}phenyl)-2-methyltetrahydro-2H-pyran-4-carboxamide | 1H NMR (400 MHz, CHLOROFORM-d) d ppm 1.13 (d, J = 6.06 Hz, 3H) 1.84-2.05 (m, 1H) 2.18-2.29 (m, 3H) 3.31-3.42 (m, 2H) 3.85 (dd, J = 4.30, 1.95 Hz, 1H) 3.88 (s, 3H) 5.08 (br. s., 1H) 5.25 (br. s., 1H) 6.31 (d, J = 1.95 Hz, 1H) 7.18 (t, J = 8.70 Hz, 1H) 7.31-7.40 (m, 6H) 7.53 (d, J = 1.95 Hz, 1H) |
| 78 | 4-(3-{[4-(4-bromo-1-methyl-1H-pyrazol-5-yl)-3-fluorophenyl]thio}phenyl)tetrahydro-2H-pyran-4-carboxamide | 1H NMR (400 MHz, DMSO-d6) d ppm 1.75-1.87 (m, 2H) 2.42 (d, J = 13.18 Hz, 2H) 3.46 (t, J = 10.98 Hz, 2H) 3.66-3.76 (m, 5H) 7.05-7.17 (m, 3H) 7.31 (br. s., 1H) 7.39-7.51 (m, 4H) 7.56 (s, 1H) 7.68 (s, 1H) |
| 79 | (2S,4S)-4-(2-fluoro-3-{[4-(1-methyl-1H-pyrazol-5-yl)phenyl]thio}phenyl)-2-methyltetrahydro-2H-pyran-4-carboxamide | 1H NMR (400 MHz, CHLOROFORM-d) d ppm 7.54 (1H, d, J = 1.9 Hz), 7.32 (5H, m), 7.22-7.28 (1, H, m), 7.17 (1H, t, J = 7.8 Hz), 6.32 (1H, d, J = 1.9 Hz), 5.50 (1H, br.s), 3.92-3.99 (1H, m), 3.90 (3H, s), 3.48-3.59 (2H, m), 2.28-2.43 (H, m), 1.99 (1H, dd, J = 14.1, 11.4 Hz), 1.20 (3H, d, J = 6.2 Hz) |
| 80 | 2,2-dimethyl-4-(3-{[4-(1-methyl-1H-pyrazol-5-yl)phenyl]thio}phenyl)tetrahydro-2H-pyran-4-carboxamide | 1H NMR (400 MHz, DMSO-d6) d ppm 1.06-1.29 (m, 6H) 1.43 (s, 1H) 2.74 (t, J = 6.95 Hz, 2H) 3.41 (t, J = 6.95 Hz, 2H) 3.84 (s, 3H) 5.18 (br. s., 1H) 5.40 (s, 1H) 6.27-6.50 (m, 2H) 6.87 (br. s., 1H) 6.98 (br. s., 2H) 7.31-7.53 (m, 6H) |
| 81 | (2S,4S)-2-methyl-4-(3-{[4-(1-methyl-1H-pyrazol-5-yl)phenyl]thio}phenyl)tetrahydro-2H-pyran-4-carboxamide | 1H NMR (400 MHz, CHLOROFORM-d) d ppm 1.16 (d, J = 6.14 Hz, 3H) 1.97 (dd, J = 14.00, 11.26 Hz, 2H) 2.24-2.34 (m, 1H) 2.24-2.34 (m, 2H) 3.42 (td, J = 10.41, 6.14 Hz, 2H) 3.87 (dd, J = 4.10, 2.05 Hz, 1H) 3.90 (s, 3H) 5.17 (br. s., 1H) 5.59 (br. s., 1H) 6.31 (d, J = 2.05 Hz, 1H) 7.31-7.36 (m, 2H) 7.38 (d, J = 3.07 Hz, 3H) 7.40 (s, 1H) 7.41-7.43 (m, 1H) 7.51 (d, J = 1.71 Hz, 1H) |
| 82 | (2R,4S)-2-methyl-4-(3-{[4-(1-methyl-1H-pyrazol-5-yl)phenyl]thio}phenyl)tetrahydro-2H-pyran-4-carbonitrile | 1H NMR (400 MHz, CHLOROFORM-d) d ppm 1.25-1.32 (m, 2H) 1.27 (d, J = 2.73 Hz, 3H) 1.71 (dd, J = 13.48, 11.09 Hz, 1H) 2.01-2.13 (m, 2H) 3.89-3.99 (m, 4H) 4.11 (dd, J = 3.93, 2.22 Hz, 1H) 6.33 (d, J = 2.05 Hz, 1H) 7.34-7.45 (m, 7H) 7.53 (d, J = 1.71 Hz, 1H) 7.54 (s, 1H) |
| 83 | (2R,4R)-2-methyl-4-(3-{[4-(1-methyl-1H-pyrazol-5-yl)phenyl]thio}phenyl)tetrahydro-2H-pyran-4-carbonitrile | 1H NMR (400 MHz, CHLOROFORM-d) d ppm 1.22 (d, J = 6.14 Hz, 3H) 1.26 (s, 1H) 2.08 (dd, J = 14.34, 10.58 Hz, 1H) 2.34-2.50 (m, 2H) 3.43-3.55 (m, 2H) 3.89 (d, J = 4.10 Hz, 1H) 3.92 (s, 3H) 6.33 (d, J = 1.71 Hz, 1H) 7.35-7.46 (m, 8H) 7.54 (d, J = 2.05 Hz, 1H) |
| 84 | (2S,4S)-2-methyl-4-(3-{[4-(1-methyl-1H-pyrazol-5- | 1H NMR (400 MHz, DMSO-d6) d ppm 1.09 (d, J = 6.59 Hz, 3H) 1.91 (dd, J = 13.91, 10.98 Hz, 1H) 2.13-2.25 (m, 1H) 3.34 (dd, J = 9.88, 5.49 Hz, 1H) 3.77 (d, J = 11.71 Hz, 1H) 3.85 (s, 3H) 6.42 (s, |

-continued

| Ex # | IUPAC NAME | NMR data |
|---|---|---|
| | yl)phenyl]thio}phenyl)tetrahydro-2H-pyran-4-carbonitrile | 1H) 7.36-7.48 (m, 2H) 7.36-7.48 (m, 2H) 7.48-7.60 (m, 5H) |
| 85 | 4-[3-({2-cyano-4-[(1-methyl-1H-pyrazol-5-yl)carbonyl]phenyl}thio)phenyl]tetrahydro-2H-pyran-4-carboxamide | 1H NMR (400 MHz, DMSO-d6) δ ppm 8.25 (1H, d, J = 1.9 Hz), 7.98 (1H, dd, J = 8.4, 2.0 Hz), 7.47-7.70 (5H, m), 7.30 (1H, s), 7.02-7.19 (2H, m), 6.88 (1H, d, J = 2.2 Hz), 4.08 (3H, s), 3.66-3.81 (2H, m), 3.47 (2H, t, J = 10.4 Hz), 2.43 (2H, d, J = 13.5 Hz), 1.76-1.92 (2H, m) |
| 86 | N-ethyl-4-(3-{[4-(1-methyl-1H-pyrazol-5-yl)phenyl]thio}phenyl)tetrahydro-2H-pyran-4-carboxamide | 1H NMR (DMSO-d6, 300 MHz) d ppm: 7.75 (t, J = 5.5 Hz, 1H), 7.55 (d, J = 8.5 Hz, 2H), 7.47 (d, J = 2 Hz, 1H), 7.45-7.37 (m, 3H), 7.35-7.28 (m, 3H), 6.43 (d, J = 1.92 Hz, 1H), 4.31 (s, 2H), 3.85 (s, 3H), 3.75 (d, J = 11.5 Hz, 2H), 3.46 (t, J = 10.5 Hz, 2H), 3.03 (m, 2H), 2.40 (d, J = 13.8, 2H), 1.90 (td, J = 12.1, 3.9 Hz, 2H, 0.90 (t, J = 7.2 Hz, 3H). APCI+ = 422. |
| 87 | 4-(2-chloro-3-{[4-(1-methyl-1H-pyrazol-5-yl)phenyl]thio}phenyl)tetrahydro-2H-pyran-4-carboxamide | 1H NMR (400 MHz, DMSO-d6) δ ppm 1.97-2.08 (m, 2H) 2.35 (d, J = 13.96 Hz, 2H) 3.55-3.63 (m, 2H) 3.82 (ddd, J = 11.21, 7.99, 2.82 Hz, 2H) 3.89 (s, 3H) 6.48 (d, J = 1.88 Hz, 1H) 6.62 (br. s., 1H) 6.95 (br. s., 1H) 6.97 (dd, J = 8.06, 1.34 Hz, 1H) 7.33 (t, J = 7.92 Hz, 1H) 7.46-7.50 (m, 2H) 7.51 (ddd, J = 8.46, 2.15, 2.01 Hz, 2H) 7.62 (ddd, J = 8.53, 2.28, 2.08 Hz, 2H). |
| 88 | 4-(3-{[2-cyano-4-(1-methyl-1H-pyrazol-5-yl)phenyl]thio}phenyl)tetrahydro-2H-pyran-4-carboxamide | 1H NMR (400 MHz, DMSO-d6) ppm 1.73-1.89 (m, 2H) 2.32-2.44 (m, 2H) 2.48 (s, 3H) 3.45 (t, 2H) 3.71 (d, J = 14.46 Hz, 2H) 6.49 (d, J = 1.46 Hz, 1H) 7.02 (br. s., 1H) 7.17 (d, J = 8.42 Hz, 1H) 7.24 (br. s., 1H) 7.35-7.42 (m, 1H) 7.44-7.57 (m, 4H) 7.71-7.79 (m, 1H) 8.07 (d, J = 1.46 Hz, 1H) |
| 89 | 4-(3-{[3-chloro-4-(1-methyl-1H-pyrazol-5-yl)phenyl]sulfinyl}phenyl)tetrahydro-2H-pyran-4-carboxamide | 1H NMR (400 MHz, DMSO-d6) d ppm 1.75-1.87 (m, 2H) 2.46 (d, J = 13.43 Hz, 2H) 3.47 (t, J = 10.34 Hz, 2H) 3.62 (s, 3H) 3.69-3.77 (m, 2H) 6.37 (d, J = 1.88 Hz, 1H) 7.11 (s, 1H) 7.32 (s, 1H) 7.51 (d, J = 2.15 Hz, 1H) 7.55 (d, J = 5.10 Hz, 2H) 7.64 (d, J = 8.06 Hz, 1H) 7.66-7.70 (m, 1H) 7.80 (dd, J = 8.06, 1.88 Hz, 1H) 7.86 (s, 1H) 7.99 (d, J = 1.88 Hz, 1H) |

Bio Data
Assays for Allergic and Non Allergic Airways Diseases
Fluorescence Intensity 5-LOX Enzyme Assay The enzyme assay is based on the oxidation of the non-fluorescent compound 2'7'-dichlorodihydrofluorescein diacetate (H2DCFDA) to the fluorescent 2',7'-dichlorofluorescein by 5-LOX in an arachidonic acid-dependent reaction. Ester cleavage of the acetate groups of the substrate H2DCFDA must occur prior to oxidation. This is achieved through use of a crude cell lysate preparation of recombinant human 5-LOX. The enzyme assay (40 L) contained 50 mM Tris (pH 7.5), 2 mM $CaCl_2$, 2 mM EDTA, 3 µM arachidonic acid (Nu-Chek Prep; #S-1133), 10 µM ATP, 10 µM H2DCFDA (Invitrogen; #D399), inhibitor (varying concentration) and recombinant human 5-LOX enzyme (1.25 µL crude lysate per well).

Inhibitors (dissolved in DMSO) were plated into a 384-well assay plate (Corning #3654) at 1 µL followed by a 20 µL addition of a solution containing 5-LO enzyme and H2DCFDA. Enzyme and H2DCFDA were pre-incubated for 5 min to allow time for acetate group cleavage of the dye prior to addition to the assay plate. After a 10 min pre-incubation of inhibitor and enzyme/dye mix, the assay was initiated by the addition of a substrate solution containing arachidonic acid and ATP. The enzymatic reaction was run for 20 min at room temperature and terminated by the addition of 40 µL of acetonitrile. Assay plates were read in a plate reader using standard wavelengths for fluorescein. $IC_{50}$s of inhibitors were calculated using a 4-parameter fit using 7 inhibitor concentrations in duplicate with 3-fold serial dilutions. Controls on each plate included no inhibitor (zero percent effect) and 25 µM C J-13610 (one hundred percent effect). The highest inhibitor concentration tested was typically 25 µM. The final DMSO concentration in the assay was 2.5%.

Human Whole Blood Assay

Human whole blood is collected in 10 ml heparin tubes (Vacutainer, Becton Dickenson). Collected blood is pooled and 80 µL is dispensed into each well of 384 well polypropylene plates. A PlateMate is used to add 2 µL of compound solution in DMSO to the 80 µL of blood in the polypropylene plates. The plate, with blood and compound added, is incubated at room temperature for 10 minutes. 2 µL of a calcimycin (800 ng/ml) (A23187 C-7522, Sigma) and arachidonic acid (30 µM) (NU-Chek PREP, INC. S-1133) solution in 60% ethanol is then added to the blood using a Micromultidrop. The plates are then incubated at 37° C. in a shallow water bath for 15 minutes. Plates are then spun at 800 g for 10 minutes at 4° C. Supernatant is removed and assayed by Elisa (Caymen Chemical).

Eicosanoid Production from Human Whole Blood:

Human whole blood was collected from healthy or asthmatic human donors in 10 ml heparinized tubes (Vacutainer tubes; Becton Dickenson, Franklin Lakes, N.J.). Collected blood was pooled and 80 µL was dispensed into each well of 384 well polypropylene plates using a Multi-prop™ 384-well dispenser (Titertek, Huntsville, Ala.). Varying concentrations of compounds were dissolved in DMSO then 2 µL/well was added to the blood using a PlateMate Plus™ automated pipetting station (Matrix Technologies, Hudson, N.H.). The compounds were preincubated with the blood at room temperature for 10 minutes followed by stimulation with 40 µM calcium ionophore (A23187, Sigma Chemical Co, St. Louis, Mo., Cat. # C-7522) and 30 μM arachidonic acid (S-1133, NU-Chek PREP, Inc., Elysian, MN, Cat. # S-1133) dissolved in 60% ethanol. After 15 min incubation at 37° C. in a shallow water bath, the blood was centrifuged at 8009 for 10 minutes at 4° C., the supernatants collected, and leukotriene and prostaglandin levels measured by ELISA according to the manufacturer's directions (Cayman Chemical Company, Ann Arbor, Mich.). The assay was performed at a final concentration of 2.5% DMSO.

Carrageenan-Induced Eicosanoid Production in the Rat Air Pouch:

Male Lewis rats (175-200 g), Charles River Laboratories, Wilmington, Mass.) were used in the study. Air pouches were produced by subcutaneous injection of 20 ml of sterile air into the intrascapular area of the back. Pouches were allowed to develop for 1 day. Animals (6 per group) were fasted with free access to water for 16 to 24 hours prior to drug administration. Drugs or vehicle were administered by gavage 1 hour prior to injection of 2 ml of a 1% suspension of carrageenan (FMC BioPolymer, Philadelphia, Pa., Cat. # GP209-NF) dissolved in saline into the pouch. At 3 hours post-carrageenan injection, 1 ml of 50 μg/ml calcium ionophore in saline (A23187, Sigma Chemical Co, St. Louis, M, Cat. #C-7522) was injected into the pouch and the pouch fluid collected 10 minutes later by lavage. The fluid was centrifuged at 3500 rpm for 10 minutes at 4° C., and the supernatants were collected for analysis. Leukotriene and prostaglandin levels were quantitated by ELISA according to the manufacturer's directions (Cayman Chemical Company, Ann Arbor, Mi).

Results obtained in the assays for allergic and non allergic airways diseases are reported in Table III, below.

| Example # | (a) | (b) | (c) |
|---|---|---|---|
| 1 | 89.7 | 76.5 | 50.5 |
| 2 | 660 | 196 | 0 |
| 3 | 102 | 179 | n.a. |
| 4 | 12.5 | 260 | n.a. |
| 5 | 15.9 | 410 | n.a. |
| 6 | 86.1 | 225 | n.a. |
| 7 | 38.6 | 78.5 | n.a. |
| 8 | 14 | 253 | n.a. |
| 9 | 14.8 | 208 | n.a. |
| 10 | 287 | 294 | 5 |
| 11 | 386 | 260 | 69 |
| 12 | 454 | 267 | n.a. |
| 13 | 54 | 119 | 1 |
| 14 | 110 | 447 | n.a. |
| 15 | 264 | 365 | 68.5 |
| 16 | 67.9 | 331 | 0 |
| 17 | 146 | 962 | 83 |
| 17(7) | 126 | 256 | n.a. |
| 18 | 369 | 596 | n.a. |
| 19 | 114 | 996 | 95.3 |
| 19(10) | 50.5 | 480 | n.a. |
| 20 | 225 | 448 | 91 |
| 21 | 567 | 859 | 96 |
| 22 | 16.4 | 185 | 99.5 |
| 23 | 39.8 | 314 | 76 |
| 24 | 692 | 150 | 32 |
| 25 | 32.9 | 83.6 | n.a. |
| 26 | 28.4 | 690 | n.a. |
| 27 | 19.8 | 138 | 100 |
| 27(2) | 331 | 123 | 100 |
| 28 | 21 | 227 | 100 |
| 28(2) | 38.9 | 42.2 | n.a. |
| 29 | 14.9 | 265 | 100 |
| 29(2) | 30 | 62.5 | 100 |
| 30 | 14 | 200 | n.a. |
| 30(2) | 113 | 55.7 | 95 |
| 31 | 15.5 | 337 | n.a. |
| 31(1) | 21.5 | 59.8 | 96 |
| 32 | 16.8 | 232 | n.a. |
| 32(1) | 151 | 107 | 93 |
| 33 | 110 | 492 | 76 |
| 34 | 40.2 | 549 | 99.5 |
| 35 | 313 | 769 | n.a. |
| 36 | 188 | 466 | n.a. |
| 37 | 60.7 | 394 | n.a. |
| 38 | 469 | 640 | n.a. |
| 39 | 23.8 | 407 | 66 |
| 40 | 21.9 | 407 | 96 |
| 41 | 277 | 405 | 98 |
| 42 | 737 | 851 | n.a. |
| 43 | 575 | 913 | n.a. |
| 44 | 138 | 866 | n.a. |
| 45 | 84 | 33 | n.a. |
| 46 | 4130 | 539 | 0 |
| 47 | 7770 | 676 | n.a. |
| 48 | 387 | 124 | 38 |
| 49 | 2710 | 999 | n.a. |
| 50 | 25000 | n.a. | 12 |
| 51 | 554 | 203 | 77 |
| 52 | 20.7 | 272 | 100 |
| 52(4) | 29.1 | 118 | 97 |
| 53 | 65.7 | 350 | 94 |
| 54 | 447 | 1160 | n.a. |
| 55 | 357 | 1240 | 64 |
| 56 | 43.2 | 472 | 62 |
| 57 | 85.1 | 514 | 62 |
| 58 | 156 | 1140 | 0 |
| 59 | 816 | 890 | n.a. |
| 60 | 608 | 1400 | n.a. |
| 61 | 327 | 2160 | n.a. |
| 62 | 2160 | 1490 | n.a. |
| 63 | 256 | 1260 | n.a. |
| 64 | 470 | 8270 | n.a. |
| 65 | 81.3 | 1060 | n.a. |
| 66 | 25000 | n.a. | n.a. |
| 67 | 209 | 1210 | n.a. |
| 68 | 803 | 2480 | n.a. |
| 69 | 1590 | 3350 | n.a. |
| 70 | 740 | 3130 | n.a. |
| 71 | 430 | 1980 | n.a. |
| 72 | 109 | 6360 | n.a. |
| 73 | 13.4 | 672 | n.a. |
| 74 | 25000 | n.a. | n.a. |
| 75 | 12200 | n.a. | n.a. |
| 76 | 108 | 727 | n.a. |
| 77 | 6380 | n.a. | n.a. |
| 78 | 153 | 1380 | n.a. |
| 79 | 3310 | n.a. | n.a. |
| 80 | 3540 | n.a. | n.a. |
| 81 | 7560 | n.a. | n.a. |
| 82 | 1200 | 530 | n.a. |
| 83 | 10300 | n.a. | n.a. |
| 84 | 2230 | n.a. | n.a. |
| 85 | 2750 | n.a. | n.a. |
| 86 | 324 | 565 | n.a. |
| 87 | 1100 | 1010 | n.a. |
| 88 | 3220 | 1170 | n.a. |
| 89 | 25000 | n.a. | n.a. |
| (d) | 877 | 275 | 73.1 |

TABLE III (a) Fluorescence Intensity 5-LOX Enzyme Assay IC50
(b) Eicosanoid production from human whole blood IC50
(c) Carrageenan-induced eicosanoid production in the rat air pouch % inhibition at 3 mpk
(d) 4-(3-(4-(2-methyl-1H-imidazol-1-yl)phenylthio)phenyl)-tetrahydro-2H-pyran-4-carboxamide disclosed in U.S. Pat. No. 5,883,106 and EP 0787127)

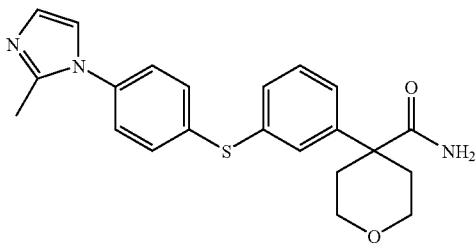

Numbers in parenthesis indicate the step of a specific example. For example, 29(2) refers to the compound prepared in step 2 of example 29.

Determination of PK Parameters

Male Sprague-Dawley rats are purchased from Charles River Laboratories (Wilmington, Del.) and acclimated to their surroundings for approximately one week with food and water provided ad libitum. On the day prior to study, animals are anesthetized with Isoflurane (to effect) and then implanted with vascular catheters in the carotid artery and jugular vein. Animals are acclimated in Culex (Bioanalytical Systems, Inc.) cages overnight prior to dosing. Patency of the carotid artery catheter is maintained using the "tend" function of Culex ABS. Animals are fasted overnight (~18 hours) prior to oral dosing, and fed at 4 hours post-dose. Dosing is performed using a single crossover design with oral dosing on Day 1 followed by intravenous dosing via the jugular vein catheter on Day 2. Both routes are dosed at 1 mg/kg. Body weights are determined on the morning of dosing. Blood collections are performed by the Culex at predetermined time points of 0.03, 0.08, 0.25, 0.5, 1, 1.5, 2, 4, 6, 8, 12, 18, and 24 hours. Samples are collected into chilled heparinized tubes, centrifuged for 10 minutes at 3000 rpm, and the resulting plasma aliquoted to 96-well plates for bioanalysis. Samples are frozen as soon as the plasma is harvested, and the plate frozen at −80° C. after the completion of the study until bioanalysis is performed. Urine samples are collected from 0 to 24 hours after intravenous dosing. A 200 μL sample is aliquoted to the sample plate and analyzed with the plasma samples. Approximately 1.8 mL of the remaining urine sample is transferred to a sample tube and reserved for additional analysis if necessary, and the remainder of the sample is discarded. Analysis is performed by LC-MS relative to a standard sample.

Assays for Pain Diseases

In Vivo

All procedures follow the guidelines of the Pfizer Animal Care and Use Committee and are in accordance with NIH guidelines on laboratory animal welfare. All reagents are obtainable from Sigma (St. Louis, Mo.) unless otherwise indicated.

Carrageenan Paw

Test compounds are stored as a dry powder at room temperature. Compounds are prepared in a vehicle containing 0.5% methylcellulose and 0.025% Tween-20 and are administered by oral gavage (volume=1 ml). Male Sprague-Dawley rats (Harlan, Indianapolis, Ind.) weighing 150-250 grams are used. Rats are fasted and have free access to water overnight prior to the day of the study. Each group consists of 6 rats. Carrageenan is prepared as a 1% suspension in normal saline and a volume of 0.1 ml is injected intradermally with a 27-gauge needle into the footpad of the right hind paw of rats anesthetized with $CO_2/O_2$. The non-injected left hindpaw serves as a normal control. Compounds are administered prior to carrageenan injection. Hyperalgesia is determined 3 hr following carrageenan injection by measurement of the withdrawal response to mechanical pressure (Randall L O, Selitto J J (1957) A method for measurement of analgesic activity on inflamed tissue. Arch Int Pharmacodyn Ther 111: 409-419) applied to the hindpaws.

Complete Freund's Adjuvant (CFA)

Adult male Sprague Dawley rats (Harlan, Indianapolis, Ind. or Charles River Laboratories, Portage, Mich.) (190-250 g) are used in these studies. Rats are not fasted prior to oral dosing and are allowed free access to food and water throughout the experiment. Each treatment group consists of 5 or 6 rats. In the CFA rat model of inflammatory pain, 150 μl of a 1 mg/ml suspension of CFA (heat killed *Mycobacterium tuberculosis* suspended in mineral oil) is injected into the plantar surface of the hind-paw of rats anesthetized with $CO_2/O_2$. This injection immediately induces local inflammation, paw swelling and pain measured as mechanical hyperalgesia (MH). The contra lateral, non-inflamed paws show thresholds comparable to those of control/normal animals. Baseline pain measurements are done for all rats one day after CFA injection using the Randall-Selitto Analgesy-Meter to measure MH of the rat hind paws. Drug studies are conducted with an acute oral gavage 48 h following CFA. Mechanical Hyperalgesia measurements are taken 2-3 hr following single dose.

Medial Meniscal Transection (MMT)

Male Sprague-Dawley rats (Harlan, Indianapolis, Ind.) weighing 275-375 grams are used in these studies. Each group consists of 6 or 8 rats. Rats undergo MMT of the right knee. Under gas anesthesia system the skin over the medial aspect of the right femorotibial joint are prepared for surgery by clipping the hair followed by cleansing using betadine. A blunt dissection allows exposure of the medial collateral ligament which is transected to expose the medial meniscus. The meniscus is cut in two pieces (distal end still attached). The proximal end of the meniscus is left in the knee joint. The skin is closed with sutures (Ethicon monofilament nylon size 5.0). Staples were removed 10-14 days following surgery. All behavioral tests begin a month following surgery. The compound is evaluated in rats that develop a consistent baseline pain response following MMT surgery. Compound is administered orally and pain responses are assessed 2-2.5 hr following compound administration. Baseline pain measurements are done for all rats 24 hr before dosing.

Spinal Nerve Ligation (SNL)

Male Sprague-Dawley rats (Harlan, Indianapolis, Ind.) weighing 275-375 grams are used. Rats have free access to food and water throughout the study. Each group consists of 5 rats. Rats undergo SNL on the left L5 and L6 (Kim S H, Chung J M.; An experimental model for peripheral neuropathy produced by segmental spinal nerve ligation in the rat. Pain, 1992; 50:355-363). Following surgical scrub/prep (betadine, alcohol), the pelvic girdle (innominate bone) is palpated and a 4 cm incision is made on the skin just to the left side of the dorsal midline using the level of the posterior iliac crests as the midpoint of the incision. At mid-sacral region, a stab is made with a scalpel blade, sliding it along the left side of the ventral column (in the sagital plane) until the blade is felt to hit the sacrum. Scissor tips are introduced through stab, and the muscle and ligaments are separated from the spine to expose 2-3 cm of the vertebral column, all the way down to the level of the sacrum/transverse processes. The bony structures of the muscle and fascia are cleared to identify the transverse process of the left L6. The lumbosacral fascia is divided to be able to gently slide the rongeur tip under the caudal edge of the L6 process. The transverse process is nipped and removed until the L4 and L5 nerves are accessible (they lie together encapsulated in fascia under the muscle just exposed). A small glass hook is placed medial to the L4, L5 nerves (downward, against the spine), the tip rotated lateral under the nerves to hook them. They are gently elevated from the surrounding muscle tissue. The L5 is dorsomedial, the hook was lowered slightly and moved toward midline to let go L4, the lateral/deep nerve. As L4 dropped of the hook, while avoiding stretching or pulling which will lead to paralysis in the left hind paw and rendering the animal unusable. Once L4 is free with L5 hook, a small length of 6-0 silk thread is tied twice around the ball at the tip of the hook and passed back under the nerve. A gentle but firm (finger tight) ligation of L5 nerve is made with a square knot, using a deep-tie hand/instrument position. The nerve bulges slightly on both sides of the ligature. Once L5 is ligated L6 was fished with the hook under the edge of the sacrum. The hook is slide under the bone at the sacroiliac rim at a 45 degree angle in the horizontal plane. L6 is gently lifted and ligated. The fascia over the muscle is suture with 4-0 vicryl and the skin closed with surgical staples. Staples are removed 10-14 days following surgery. All behavioral tests begin a month following surgery.

Compound is administered orally and pain responses are assessed 2-2.5 hr following compound administration. Baseline pain measurements are done for all rats 24 hr before dosing.

Behavioral Tests
Mechanical Hyperalciesia

Mechanical hyperalgesia of the hind paw is measured using the Randall-Selitto method with the Analgesy-Meter (Ugo-Basile). Each hind-paw, contra-lateral first and then the inflamed (ipsilateral), is sequentially placed on a blunt vice-like platform, and pressure is applied to the paw at a constantly increasing rate until the rat responds to the stimulus (moves, struggles, vocalizes). The amount of pressure needed for the rat to respond (measured in grams) is then recorded. The difference between the contralateral paw withdrawal threshold (PWT) and the injected paw withdrawal threshold is used to determine the hyperalgesic response.

Tactile Allodynia (TA)

Tactile allodynia (static) is determined by measuring paw withdrawal following probing of the plantar surface with a series of calibrated fine filaments (von Frey filaments, Stoelting Co., Wood Dale, Ill.). The strength of von Frey filaments ranges from 0.4 g to 8 g. These filaments are used as innocuous mechanical stimuli to quantify mechanical allodynia. Rats are placed in clear plastic cages on elevated wire mesh floor and a removable plastic cover to acclimate for 30 minutes. A series of filaments are applied (each 3 times) in sequence to the plantar surface of the right hind paw until the rats respond with a withdrawal. Lifting the paw is recorded as a positive response and the next lightest filament chosen for the next measurement. In the absence of a response, the next filament of increasing weight is used. This paradigm (the up-down method first described by Dixon WJ (1980) Efficient analysis of experimental observations. Annu Rev Pharmacol Toxicol 20:441-462) is continued until four measurements are made after an initial change in behavior or until consecutive negative responses occurred. The resulting sequence of positive and negative scores is used to interpolate the paw withdrawal threshold (g).

Weight Bearing Differential

Weight bearing differential (WBD) between hind-paws are measured using a force plate meter (Linton Instrumentation, Norfolk UK). Rats are placed on a flat sensor (two plates/one for each hind paw) to measure the weight bearing of each hind paw. Nine readings are taken and the median value reported.

Assays FOR Cardiovascular Diseases
Materials and Methods
LDLr Null Mouse Atherosclerosis Model.

Male LDL receptor −/− mice (6 weeks old), obtainable from Jackson Laboratories (Bar Harbor, Me.) are singly housed in a constant temperature environment with alternating 12-hour light and dark cycles. Water is available at all times. Following an acclimation period of two to four weeks on standard rodent chow, mice are switched to a modified Western Diet Mice (D06092202, Research Diets Inc.) with 0.075% added cholesterol for a period of 12 to 36 weeks. Mice are then assigned to treatment groups of 8-20 mice/group using a block randomization procedure so that all groups have similar serum cholesterol and body weight means and ranges and given free access to a dietary admixture utilizing the modified Western Diet (D060922, Research Diets Inc.)+/−varying concentrations of PF-4332150. The concentration of drug in the diet is adjusted such that mouse diet consumption per day would result in predictable plasma exposures. Blood for serum lipids, inflammatory mediators and other biomarkers, hepatic enzymes and drug pharmacokinetic analysis is collected in 1 ml heparinized tubes (Vacutainer tubes; Becton Dickenson, Franklin Lakes, N.J.). at selected times throughout the treatment period by orbital sinus or cardiac puncture, subjected to 900×g for 10 minutes at room temperature and the serum decanted. Following the treatment period, liver, heart, pancreas and vascular tissue is removed and placed into 10% buffered formalin (Sigma Aldrich, St. Louis) or flash frozen in liquid nitrogen for future analysis.

Determination of Tissue and Serum Lipids
Total Cholesterol Analysis

Tissue analysis of total cholesterol is conducted using Total Cholesterol E kit (Wako Chemicals USA, VA, USA) according to manufacturer's specification. Five microliters of sample, diluted within assay linearity in PBS pH 7.4 (Invitrogen, Wis., USA), is added to a 96-well clear-bottom plate (Costar, N.Y., USA). Each 96-well clear bottom plate also contained designated wells with 5 microliters of provided cholesterol standard having concentrations ranging from 18.75-200 milligrams per deciliter. 2× Color Reagent solution is prepared by addition of 75 milliliters provided buffer solution to the lyophilized color reagent. Ninety-five microliters of 2× Color Reagent solution is added to each well followed by 30 minute incubation at 37° C. Colorimetric changes are measured on a Tecan Safire 2 at 600 nm. Total cholesterol is quantified via linear curve-fit of the cholesterol standards.

Free Cholesterol Analysis

Tissue analysis of free cholesterol is conducted using Free Cholesterol E kit (Wako Chemicals USA, VA, USA) according to manufacturer's specification. Five microliters of sample, diluted within assay linearity in PBS pH 7.4 (Invitrogen, Wis., USA), is added to a 96-well clear-bottom plate (Costar, N.Y., USA). Each 96-well clear bottom plate also contained designated wells with 5 microliters of provided cholesterol standard having concentrations ranging from 10-100 milligrams per deciliter. 2× Color Reagent solution is prepared by addition of 75 milliliters provided buffer solution to the lyophilized color reagent. Ninety-five microliters of 2× Color Reagent solution is added to each well followed by 30 minute incubation at 37° C. Colorimetric changes are measured on a Tecan Safire 2 at 600 nm. Free cholesterol was quantified via linear curve-fit of the cholesterol standards.

Triglyceride Analysis

Tissue analysis of triglyceride is conducted using L-Type TG H kit (Wako Chemicals USA, VA, USA) according to manufacturer's specification. Five microliters of sample, diluted within assay linearity in PBS pH 7.4 (Invitrogen, Wis., USA), is added to a 96-well clear-bottom plate (Costar, N.Y., USA). Each 96-well clear bottom plate also contains designated wells with 5 microliters of provided triglyceride standard having concentrations ranging from 5.5-110 milligrams per deciliter. One-hundred-fifty microliters of L-Type TG H Enzyme Color Reagent A (R1) is added to each well followed by 5 minute shaking then 5 minute incubation at 37° C. Colorimetric changes are measured on a Tecan Safire 2 at 600 nm and values retained for background normalization of the data. Seventy-five microliters of L-Type TG H Enzyme Color Reagent B (R2) is added to each well followed by 5 minute shaking then 30 minute incubation at 37° C. Colorimetric changes are measured on a Tecan Safire 2 at 600 nm. Background values from first read are subtracted prior to determining concentrations via linear curve-fit of the triglyceride standards.

Non-Esterified Fatty Acid Analysis

Tissue analysis of non-esterified fatty acids (NEFA) is conducted using Wako NEFA C kit (Wako Chemicals USA, VA, USA) according to manufacturer's specification. Ten microliters of sample, diluted within assay linearity in PBS pH 7.4 (Invitrogen, Wis., USA), is added to a 96-well clear-bottom plate (Costar, N.Y., USA). Each 96-well clear bottom plate also contains designated wells with 10 microliters of provided NEFA standard having concentrations ranging from 0.05-1 millimole. Color Reagent A is prepared by addition of provided buffer solution A to the lyophilized color reagent. Seventy-five microliters of Color Reagent A is added to each well followed by 5 minute shaking then 5 minute incubation at 37° C. Colorimetric changes are measured on a Tecan Safire 2 at 550 nm and values retained for background normalization of the data. Color Reagent B is prepared by addition of provided buffer solution B to the lyophilized color reagent. One-hundred-fifty microliters of Color Reagent B is added to each well followed by 5 minute shaking then 30 minute incubation at 37° C. Colorimetric changes are measured on a Tecan Safire 2 at 550 nm. Background values from first read are subtracted prior to determining concentrations via linear curve-fit of the NEFA standards.

Lipoprotein-Associated Cholesterol Analysis

Lipoprotein-associated cholesterol analysis is conducted using fast-protein liquid chromatography (FPLC) utilizing a Superose 6HR column and in-line post-column analysis of cholesterol levels in lipoproteins. Plasma samples are pre-filtered through a 0.6µ 96-well filter plate before injection of 50 µL over a Superose 6-10/300GL column (Amersham Biosciences, Sweden) via a Varian 430 autosampler (Varian Inc., Ca, USA). Lipoproteins are separated by isocratic size-exclusion at 0.518 mL/min. with 0.9% saline as the mobile phase. The eluent combined with a solution of 50% Cholesterol R1 (Roche Diagnostics, 1N, USA) pumped at 0.182 mL/min. (26% of total flow rate) before entering a CRX 400 post column reactor set to 37° C. (Pickering Laboratories, Ca, USA). Following the cholesterol staining reaction, eluent lipoprotein-cholesterol is detected at 490 nm with a Varian Pro-Star UV-Vis detector. Cholesterol concentrations (mg/dL) in each lipoprotein are quantified by multiplication of the respective relative cholesterol distribution by the total plasma cholesterol determined enzymatically as described above.

Neutral Lipid Analysis via High Performance Liquid Chromatography Evaporative Light Scattering Detection (HPLC-ELSD)

Tissue samples are extracted with 3 mL of a 4:1 mixture of 2,2,4-trimethylpentane (TMP) and isopropyl alcohol (IPA). 10 µL of a 2 mg/mL solution of arachidonic alcohol (AA) is added to each sample to serve as the internal standard for analytical analysis. Samples are shaken for 24 hours at room temperature in the absence of light. Following the extraction, 1 mL of water is added to the sample and vortexed for 15 minutes. The sample is then centrifuged at 1,500 rpm for 15 minutes. Two milliliters of the organic phase (top layer) is transferred to a glass vial for analysis and dried down under $N_2$. Each sample is reconstituted with 50 uL of TMP, vortexed, and then transferred to a 2 mL HPLC vial with 100 uL glass insert.

Chromatography: A Waters Spherisorb S3W 4.6×100 mm analytical column is maintained at 30° C. by an Agilent column heater unit. The HPLC autosampler is programmed to maintain the sample temperature at 20° C. throughout the run. Ten microliters of each sample is injected. The mobile phase consists of a two solvents gradient. Solvent A is trimethylpentane (TMP; Mallincrodt 6051-08) and solvent B was ethylacetate (EA; Mallincrodt 3442-10). The gradient is described in the table below:

| Time (min) | Solvent A (%) | Solvent B (%) | Flow (mL/min) |
|---|---|---|---|
| 0 | 99 | 1 | 2 |
| 5 | 65 | 35 | 2 |
| 6 | 5 | 95 | 2 |
| 7 | 5 | 95 | 2 |
| 7.1 | 99 | 1 | 2 |

Detection: The ELSD is operated at 45° C. with a gain of 8, and $N_2$ pressure maintained at 3.1 bar. Analog signal obtained by the instrument is sent to the Agilent A/D interface module where it is converted to a digital output. The conversion is based on a 10,000 mAU/V set point, and the data rate is set at 10 Hz (0.03 min). The resulting digital output is then fed into the Agilent ChemStation® software for integration of the peak area. The concentration of cholesterol and cholesterol ester is converted to µg/mL using a calibration curve of cholesterol (Sigma-Aldrich 362794) and cholesteryl oleate (Sigma-Aldrich C9253). Both calibration curves are best fit to a second order polynomial equation $Y=A+B(X)+C(X2)$. Cholesterol response is linear from 20 to 800 µg/mL. The cholesterol ester response is linear from 20 to 700 µg/mL.

Dual-Label Cholesterol Absorption Model 6 week old male LDLr−/− mice acquirable from the Jackson Laboratory, are housed under a normal 12 hr light and dark cycle and given free access to food and water throughout the study period. Mice are acclimated to the laboratory environment for 7 days on Purina 5001 rodent chow followed by seven days of acclimation to a modified western diet and subsequently divided into treatment groups. Assessment of the impact of test articles on intestinal cholesterol absorption is determined using the dual-label fecal isotope ratio method as described previously. Following 4 days of study diet admixture exposure, non-fasted and non-anesthetized mice are given an intragastric gavage of $^3$H-sitostanol (2.78 uCi) and $^{14}$C-cholesterol (1.74 uCi) dissolved in 150 µl of 100% medium chain triglyceride (MCT) oil. Mice are immediately transferred into individual wire-bottom cages where they continue to ingest their respective study diet admixtures for an additional 72 hours during which time feces is collected daily and pooled.

Total pooled 3-day fecal samples are dried under N2 gas, pulverized and a sample from each animal on study oxidized for $^3$H and $^{14}$C isotope content (DPM) via standard dual-count methodology utilized by the WBAL-IMS COE for quantification of $^{14}$C and $^{3}$H concentrations. The corrected DPM value is refined by subtracting out background and dividing by the mean oxidation efficiency. This value is used to calculate the final unstable isotope activity in nCi which is subsequently divided by the mass of the dried fecal sample oxidized to provide unstable isotope content in nCi/mg feces. The ratio of $^{14}$C to $^{3}$H content is determined for each animal and % cholesterol Absorption determined in the following manner: % cholesterol Absorption=

$$\frac{\left[\begin{array}{c}(^{14}C\text{-}cholesterol^{administered}/^{3}H\text{-}sitostanol^{administered})-\\(^{14}C\text{-}cholesterol^{fecal}/^{3}H\text{-}sitostanol^{fecal})\end{array}\right]}{(^{14}C\text{-}cholesterol^{administered}/^{3}H\text{-}sitostanol^{administered})}\times 100$$

Mean and standard deviations of the mean for "% cholesterol absorption" are determined for all groups. Statistical significance for treatment groups, in comparison to untreated mice, is determined using a Dunnette Pairwise Comparison with a one-sided P-value (P<0.05).

14C-Acetate Incorporation into Non-Saponafiable and Saponafiable Lipids (5LOCS-001)

21 week old male LDLr–/– mice from the Jackson Laboratory are housed under a normal 12 hr light and dark cycle and given free access to water and study diets, with the exception when only water is provided during a 6 hr fast on the last day on study. Mice are acclimated for 7 days to a modified western diet (D06092202, Research Diets Inc.) and subsequently divided into treatment groups. Both acute and chronically treated mice are fasted 2.5 hours prior to their intragastric gavage of vehicle or test article. For both acute and chronic test article exposure groups a single intraperitoneal injection of 25 uCi of [1-$^{14}$C]-acetate in saline is delivered 1.5 hours after intragastric vehicle or test article delivery. Mice are euthanized with CO2 inhalation 2.5 hours after [1-$^{14}$C]-acetate exposure and blood collected and subsequently processed for serum separation. Incorporation of [1-$^{14}$C]-acetate into saponifiable (SAP) and non-saponafiable (NONSAP) serum lipids is determined as previously described from between 0.175 ml and 0.3 ml of serum. DPM per millilitre of serum for SAP and NONSAP lipids is determined for each animal and mean, and standard deviation of the mean, are determined for all groups. Statistical significance for treatment groups, in comparison to untreated mice, is assessed using an unpaired Student's T-test (P<0.05).

Soluble Biomarkers

Mouse serum or plasma samples are collected at various times from a variety of efficacy studies conducted for this project. Samples are tested in several different assay systems both internal and external to the company. The ADVIA® 1650 Chemistry System is used for the in vitro diagnostic quantitative determination of alkaline phosphatase (AL-PAMP), alanine aminotransferase (ALT), and aspartate aminotransferase (AST).

(ALPAMP) The alkaline phosphatase hydrolyzes the PNPP substrate to form p-nitrophenol that is colored (yellow) and provides its own chromogen. The reaction is followed by the colorimetric measurement of the rate of formation of p-nitrophenol at 410 nm, which is proportional to the alkaline phosphatase activity. A 2-amino-2-methyl-1 propanol (AMP) buffer is used to maintain the reaction pH at 10.3-10.4. Magnesium and zinc ions are added to the AMP buffer to activate and stabilize the enzyme.

(ALT) The reaction is initiated by the addition of α-ketoglutarate as a second reagent. The concentration of NADH is measured by its absorbance at 340 nm, and the rate of absorbance decrease is proportional to the ALT activity.

(AST) The concentration of NADH is measured by its absorbance at 340 nm, and the rate of absorbance decrease is proportional to the AST activity. The reaction is initiated by the addition of α-ketoglutarate as a second reagent.

The ADVIA® 1650 Chemistry System is controlled using Bayer Assayed Chemistry Control 1 (REF 05788372; Prod. No. T03-1220-62) and Control 2 (REF 00944686; Prod. No. T03-1221-62).

Glutamate dehydrogenase (GLDH) is measured using the optimized standard kit supplied by RANDOX. This procedure measures the non-specific creep.

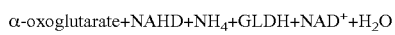

α-oxoglutarate+NAHD+NH$_4$+GLDH+NAD$^+$+H$_2$O

As NADH is oxidized, the decrease in the absorbance per minute is measured spectrophotometrically at 340 nm and is proportional to the GLDH activity. Serum and plasma samples are sent external to LinCo and Rules Based Medicine for profiling in specific panels of preferred analytes.

Methods for Histology and Image Analysis

Histology: Tissues, including the aortic sinus and root, heart, adipose, liver, muscle, etc., are removed immediately following euthanasia and either placed in 10% Neutral Buffered Formalin or frozen in Liquid N$_2$, and embedded for sectioning as described. Frozen samples of tissue are cryosectioned and stained with oil-red-o (ORO) for lipids (Bowles et al, 2004) and picrosirius red (PSR) for collagen (Rubio et al, 1988). Area percent ORO (Bowles et al, 2004) and PSR (Rubio et al, 1988) are calculated using computer assisted image analysis with ImageProPlus.

For fixed tissue analysis, tissues are fixed for 24 hrs in 10% NBF at room temperature. Tissues are dehydrated through graded alcohols and xylene into paraffin using a Tissue Tek VIP 5 tissue processor. Tissues are embedded into fresh paraffin, sections cut at 4 microns thickness using a Leica RM 2235 rotary microtome and mounted on glass slides.

To measure aortic root plaque area and composition, serial sections are cut from the aortic root as described by Nishina et al. beginning at the valve leaflets and collecting two sections per slide to generate one step. Steps 2, 8, 14, 20, 26, and 32 are stained with Masson's trichrome (Prophet) and used for plaque area measurement and composition. Plaque composition is measured on every complex plaque (Type 3 or 4). Smooth muscle cell (SMC) area within lesions is visualized using an antibody against A-SMC actin (mouse anti-human α-actin, Cat. No. M0851) adapted for mouse tissues with the Animal Research Kit (ARK), Cat. No. K3955) both from DAKO Corp., Carpenteria, Calif. Macrophages are stained with antibody against rat macrophage protein ED-1 (Serotec, Ltd., Oxford, UK) as described (Lutgens et al.)

Plaques are defined as Type 1, 2, 3 or 4 by the following criteria:

Type 1—1-2 layers of foam cells, no expansion of neointimal inflammatory cells

Type 1B—Smoother than Type 1. No inflammation. Matrix tissue-collagen. Stable

Type 2—Multiple layers of foam cells, protrusion into lumen, minimal infiltrates into plaque. Lamina/media intact. No inflammatory cells in adventitial region.

Type 2B—Type 2, plus contains more fibrous component and more matrix tissue

Type 2C— Type 2 & 2b, plus contains significant inflammatory component in adventitial region.

Type 3—Large plaque impinges on lumen and media. Cholesterol clefts, inflammatory infiltrates, irregular surface, no inflammation on adventitial side, degraded media.

Type 3B—Increased matrix component

Type 4—Similar to 3 except: adventitial inflammation, smooth plaque surface, endothelium intact, may/may not have inflammatory response in the plaque Procedure for Measuring Plaque Area and Composition Using CAST System CAST (Computer Assisted Stereological Toolbox) by Olympus Denmark, revision 0.9 is used for analysis of plaque area and composition. The areas of all plaques are measured by drawing along the perimeter of the plaque under 10× objectives. Composition of complex plaques (types 3 or 4) is measured under 10× objective using "meander sampling". For samples containing 2 or more complex plaques, a 7×7 point probe is applied to the image and random sampling is done across the entire region of interest. For samples containing only one complex plaque, an 8×8 point probe is applied. At each sampling point, the tissue at the upper right quadrant of the cross is identified as either: foam cell, collagen, and cholesterol cleft or other. The percent of tissue sampled is as close to 100% as possible without exceeding 100%.

REFERENCES

Alkaline Phosphatase Study Group. Committee on Standards of the AACC, Subcommittee on Enzymes, Tietz N W (chairman) et al. Progress in the development of a recommended method for alkaline phosphatase activity measurements. Clin Chem 26(7): 1-23 (1980)

Bowles D K, Heaps C L, Turk J R, Maddali K K, Price E M. Hypercholesterolemia inhibits L-type calcium current in coronary macro-, not microcirculation. J Appl Physiol. 96:2240-2248, 2004.

Chai S, Chai Q, Danielsen C C, Hjorth P, Nyengaard J R, Ledet T, Yamaguchi Y, Rasmussen L M, Wogensen L. Overexpression of hyaluronan in the tunica media promotes the development of atherosclerosis. *Circ Res.* 96:583-91, 2005

Cramer et al, J L R (2004) 45:1289-1301 duPont, N. C., K. Wang, et al. (2005). "Validation and comparison of luminex multiplex cytokine analysis kits with ELISA: Determinations of a panel of nine cytokines in clinical sample culture supernatants." Journal of Reproductive Immunology 66(2): 175-191.

Lutgens E, Daemen M, Kockx M, Doevendans P, Hofker M, Havekes L, Wellens H and de Muinck ED (1999) Atherosclerosis in ApoE3-Leiden transgenic mice: From proliferative to atheromatous stage. Circ 99: 276-283

Nachtigal, P., V. Semecky, A. Gojova, M. Kopecky, V. Benes, and R. Juzkova, The application of stereological methods for the quantitative analysis of the atherosclerotic lesions in rabbits. Image Analysis and Stereology, 21: 165-174, 2002

Nishina P M, Wang J, Toyofuku W, Kuypers F A, Ishida BY and Paigen B. (1993) Atherosclerosis and plasma and liver lipids in nine inbred strains of mice. *Lipids* 28: 599-605.

Prophet E B, Mills, B, Arrington J B, Sobin L H, eds. *Armed Forces Institute of Pathology Laboratory Methods in Histotechnology*. Washington, D.C.: American Registry of Pathology; 1992.

Rubio C A, Porwit A: Quantitation of fibrosis in liver biopsies. Anal Quant Cytol Histol. 10:107-109, 1988.

Temel et el. J L R (2005) 46:2423-2431

Tietz N W: *Clinical Guide to Laboratory Tests*, 3rd Edition. WB Sauders Company, Philadelphia, Pa. pp 20-21 (1995

Tietz N W: *Clinical Guide to Laboratory Tests*, 3rd Edition. WB Saunders Company, Philadelphia, Pa. pp 30-33 (1995)

EMESIS EVALUATION

Earlier compounds had been observed to produce nausea and emesis in humans after oral administration at exposures similar to those expected for therapeutic inhibition of the 5-lipoxygenase enzyme for diseases such as asthma or inflammatory disorders. The occurrence of these gastrointestinal symptoms after administration of these compounds limited their clinical utility. Experiments are undertaken to differentiate local gastrointestinal emetic stimuli during dissolution and absorption of an oral compound from emetic stimuli produced during systemic exposure through the bloodstream. Earlier, compounds are found to produce nausea and emesis through systemic exposure, rather than through local concentrations within the gastrointestinal tract at the sites of dissolution and absorption. This suggested that formulation modifications that alter the location of release or slow the dissolution of the compounds would not be effective in reducing gastrointestinal side effects. These findings are observed after 8-12 kg purpose-bred beagle dogs are administered 4-(3-{[4-(1-methyl-1H-pyrazol-5-yl)phenyl]thio}phenyl)tetrahydro-2H-pyran-4-carboxamide by IV infusion, using a loading dose followed by a slow infusion to attain a peak blood level over 30 minutes to 1 hour in duration. More specifically, compounds are diluted in phosphate buffered saline to a concentration where 10 ml/kg total volume was administered through an intravenous catheter using an infusion pump, with approximately 90% of the total dose being delivered in the first 5 minutes, and the remaining dose administered over the next 25 minutes. Similar delivery methods to produce an exposure that approximates the systemic pharmacokinetic profile seen with oral delivery are anticipated to give similar results. More rapid methods of administration and the resultant high plasma concentrations are not anticipated to discriminate useful compounds from non-useful compounds. For example, IV bolus administration may produce a higher peak plasma concentration and systemic gastrointestinal effects than those achieved for compounds that following absorption from the GI tract, would have acceptable peak plasma concentrations and therapeutic efficacy. During and after administration of the compounds, the dogs are observed for any undesirable clinical effects, most notably emesis or other signs of gastrointestinal distress. Periodic serum and plasma samples are obtained during the first 6 hours to document systemic inhibition of the 5-lipoxygenase enzyme as well as exposure levels of the compound. It is thus desirable to identify new compounds that do not have similar unwanted effects and that thus can have increased utility in the therapy of inflammatory diseases such as asthma. For compounds of the invention, emesis, can for example be evaluated by administering the named compound orally at doses of 10 mg per kg, 100 mg per kg fasted, and 100 mg per kg fed, and evaluating emesis in dogs. It is predicted that a reduction of emesis in dogs would translate to reduction or elimination of nausea or emesis in humans.

The invention claimed is:

1. The compound (2S,4R)-4-(2-fluoro-3-{[4-(1-methyl-1H-pyrazol-5-yl)phenyl]thio}phenyl)-2-methyltetrahydro-2H-pyran-4-carbonitrile, having the formula

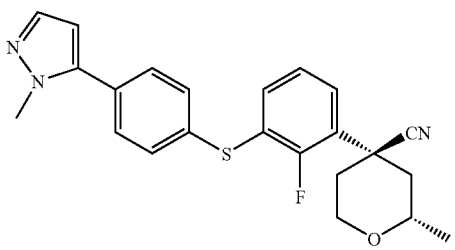

or a pharmaceutically acceptable salt thereof.

2. (2S,4R)-4-(2-fluoro-3-{[4-(1-methyl-1H-pyrazol-5-yl)phenyl]thio}phenyl)-2-methyltetrahydro-2H-pyran-4-carbonitrile, tosylate salt.

3. The compound according to claim 2, which is a 1:1 molar ratio salt of (2S,4R)-4-(2-fluoro-3-{[4-(1-methyl-1H-pyrazol-5-yl)phenyl]thio}phenyl)-2-methyltetrahydro-2H-pyran-4-carbonitrile and para-toluenesulfonic acid, which is crystalline and which has an X-ray diffraction pattern with the following principal x-ray diffraction pattern peaks expressed in terms of 2-theta angle (±0.1 degrees) when measured using Cu K$\alpha_1$ radiation (Wavelength=1.5406 Å):

| Angle 2-Theta ° |
|---|
| 13.5 |
| 14.2 |
| 18.9 |
| 23.3 |
| 24.5. |

4. A pharmaceutical composition comprising a compound of claim 1, or a pharmaceutically acceptable salt thereof, and one or more pharmaceutically acceptable excipients.

5. A pharmaceutical composition comprising a compound of claim 4, or a pharmaceutically acceptable salt thereof, and one or more pharmaceutically acceptable excipients.

* * * * *